United States Patent
Glunz et al.

(10) Patent No.: US 10,696,674 B2
(45) Date of Patent: Jun. 30, 2020

(54) SPIROLACTAMS AS INHIBITORS OF ROCK

(71) Applicant: BRISTOL-MYERS SQUIBB COMPANY, Princeton, NJ (US)

(72) Inventors: Peter W. Glunz, Yardley, PA (US); Indawati DeLucca, Pennington, NJ (US); Andrew K. Dilger, Ewing, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/315,678

(22) PCT Filed: Jul. 6, 2017

(86) PCT No.: PCT/US2017/040850
§ 371 (c)(1),
(2) Date: Jan. 7, 2019

(87) PCT Pub. No.: WO2018/009625
PCT Pub. Date: Jan. 11, 2018

(65) Prior Publication Data
US 2019/0322664 A1  Oct. 24, 2019

Related U.S. Application Data

(60) Provisional application No. 62/359,354, filed on Jul. 7, 2016.

(51) Int. Cl.
| | |
|---|---|
| *C07D 471/10* | (2006.01) |
| *C07D 401/14* | (2006.01) |
| *C07D 403/10* | (2006.01) |
| *C07D 487/10* | (2006.01) |
| *C07D 491/10* | (2006.01) |

(52) U.S. Cl.
CPC ......... *C07D 471/10* (2013.01); *C07D 401/14* (2013.01); *C07D 403/10* (2013.01); *C07D 487/10* (2013.01); *C07D 491/10* (2013.01)

(58) Field of Classification Search
CPC .. C07D 401/14; C07D 403/10; C07D 471/10; C07D 487/10; C07D 491/10; A61K 31/407
See application file for complete search history.

(56) References Cited

FOREIGN PATENT DOCUMENTS

| WO | WO199723212 A1 | 7/1997 |
|---|---|---|
| WO | WO2005014000 A1 | 2/2005 |
| WO | WO2005014589 A1 | 2/2005 |
| WO | WO2008096746 A1 | 8/2008 |
| WO | WO2009133861 | 11/2009 |
| WO | WO2014113620 A2 | 7/2014 |
| WO | WO2014134388 A1 | 9/2014 |
| WO | WO2014134391 A1 | 9/2014 |
| WO | WO2015002915 A1 | 1/2015 |
| WO | WO2015002926 A1 | 1/2015 |
| WO | WO2016010950 A1 | 1/2016 |
| WO | WO2016028971 A1 | 2/2016 |
| WO | WO2016112236 A1 | 7/2016 |
| WO | WO2016144936 A1 | 9/2016 |
| WO | WO2017123860 A1 | 7/2017 |
| WO | WO2017205709 A1 | 11/2017 |
| WO | WO2018009622 A1 | 1/2018 |
| WO | WO2018009627 A1 | 1/2018 |
| WO | WO2018102325 A1 | 6/2018 |
| WO | WO2019014300 A1 | 1/2019 |
| WO | WO2019014303 A1 | 1/2019 |
| WO | WO2019014304 A1 | 1/2019 |
| WO | WO2019014308 A1 | 1/2019 |
| WO | WO2019089868 A1 | 5/2019 |

OTHER PUBLICATIONS

Lee et al., Selective ROCK2 inhibition in focal cerebral ischemia, Annals of Clinical and Translational Neurology, 1(1), pp. 2-14, (2014).*
Simone, Oncology: Introduction, Cecil Textbook of Medicine, 20th Edition, vol. 1, pp. 1004-1101 O, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Deng, et al "Novel complex crystal structure of prolyl hydroxylase domain-containing protein 2 (PHD2): 2,8-Diazaspiro [4.5]decan-1-ones as potent, orally bioavailable PHD2 inhibitors", Bioorganic & Medicinal Chemistry, 21(21), 6349-6358 (2013).

(Continued)

*Primary Examiner* — Deepak R Rao
(74) *Attorney, Agent, or Firm* — Hong Liu

(57) ABSTRACT

The present invention provides compounds of Formula (I): or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

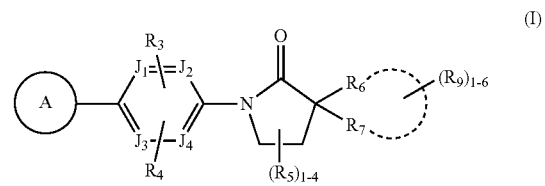

13 Claims, No Drawings
Specification includes a Sequence Listing.

(56) References Cited

OTHER PUBLICATIONS

Shah et al., "A review on ROCK-II inhibitors: From molecular modelling to synthesis", Bioorganic & Medicinal Chemistry Letters, vol. 26, pp. 2383-2391 (2016).

* cited by examiner

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<223> OTHER INFORMATION: FITC-AHA at N Terminus attached at A1 - A11
<220> FEATURE:
<221> NAME/KEY: MISC_FEATURE
<223> OTHER INFORMATION: OH at C Terminus attached at A1 - A11

<400> SEQUENCE: 1

Ala Lys Arg Arg Arg Leu Ser Ser Leu Arg Ala
1               5                   10
```

SPIROLACTAMS AS INHIBITORS OF ROCK

CROSS REFERENCE TO RELATED APPLICATIONS

This application is a 371 application of PCT/US2017/040850 filed Jul. 6, 2017 which is entitled to priority pursuant to 35 U.S.C. § 119(e) to U.S. provisional patent application No. 62/359,354, filed Jul. 7, 2016, which is incorporated herein in its entirety.

FIELD OF THE INVENTION

The present invention relates to novel spirolactams, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as ACTIN organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example, angiotensin II (Yamakawa, T. et al., *Hypertension*, 35:313-318 (2000)), urotensin II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata. M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada. N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovasc. Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovasc. Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid. N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol. Ther.*, 18:67-74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., *Int. J. Mol. Sci.*, 13:8293-8307 (2012); Zhou, L. et al., *Am. J Nephrol.*

34:468-475 (2011)), as well as neurological disorders, such as spinal-cord injury, Alzheimer disease, multiple sclerosis, stroke and neuropathic pain (Mueller, B. K. et al., *Nat. Rev. Drug Disc.*, 4:387-398 (2005); Sun, X. et al., *J Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, US 2008/0275062 A1), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel spirolactams including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

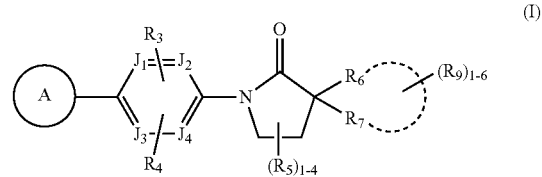

or stereoisomers, enantiomers, diastereoisomers, tautomers, pharmaceutically acceptable salts, solvates, or prodrugs thereof, wherein
Ring A is independently selected from

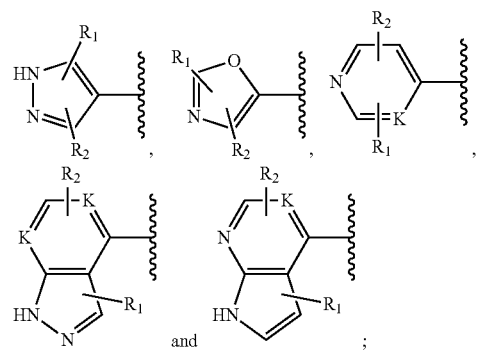

$J_1$, $J_2$, $J_3$, and $J_4$ are independently selected from N, $CR_3$, and $CR_4$; provided no more than two of $J_1$, $J_2$, $J_3$ and $J_4$ are N;
K, at each occurrence, is independently selected from N, $CR_1$, and $CR_2$;
$R_1$, at each occurrence, is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$:

$R_2$, at each occurrence, is independently selected from H, $-(CH_2)_rOR_b$, $(CH_2)_rS(O)_pR_c$, $-(CH_2)_rC(=O)R_b$, $-(CH_2)_rNR_aR_a$, $-(CH_2)_rCN$, $-(CH_2)_rC(=O)NR_aR_a$, $-(CH_2)_rNR_aC(=O)R_b$, $-(CH_2)_rNR_aC(=O)NR_aR_a$, $-(CH_2)_rNR_aC(=O)OR_b$, $-(CH_2)_rOC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;

$R_3$ is independently selected from H, F, Cl, Br, CN, $C_{1-4}$ alkyl substituted with 0-3 $R_e$, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rCN$, $-(CH_2)_rNR_aC(=O)R_b$, $-(CH_2)_rNR_aC(O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;

$R_4$ is independently selected from H, F, Cl, Br, OH, CN, $OC_{1-4}$ alkyl substituted with 0-3 $R_e$, $NR_aR_a$, and $C_{1-4}$ alkyl substituted with 0-3 $R_e$;

$R_5$ is independently selected from H, $C_{1-4}$ alkyl substituted with 0-4 $R_e$, $-(CH_2)_rOR_b$, $(CH_2)_rS(O)_pR_c$, $-(CH_2)_rC(=O)R_b$, $-(CH_2)_rNR_aR_a$, $-(CH_2)_rCN$, $-(CH_2)_rC(=O)NR_aR_a$, $-(CH_2)_rNR_aC(=O)R_b$, $-(CH_2)_rNR_aC(=O)NR_aR_a$, $-(CH_2)_rNR_aC(=O)OR_b$, $-(CH_2)_rOC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, $-C(=O)$-heterocyclyl substituted with 0-3 $R_e$, and $-(CH_2)_r$-heterocyclyl substituted with 0-3 $R_e$;

$R_6$ and $R_7$ together with the carbon atom to which they are both attached form a bicyclic carbocyclyl or a bicyclic heterocyclyl comprising carbon atoms and 1-5 heteroatoms selected from $NR_8$, O, and S:

$R_8$ is independently selected from H and $C_{1-4}$ alkyl substituted with 0-4 $R_e$;

$R_9$, at each occurrence, is independently selected from H, F, Cl, Br, $C_{1-4}$alkyl, $C_{2-4}$alkenyl, $C_{2-4}$alkynyl, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)NR_aC(=O)NR_aR_a$, $-(CHR_d)_rC(=O)OR_b$, $-(CHR_d)_rC(=O)R_b$, $-(CHR_d)_rC(=O)NR_aR_a$, $-(CHR_d)_rOC(=O)R_b$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$ alkenyl substituted with 0-5 $R_e$, $C_{2-6}$alkynyl substituted with 0-5 $R_e$, $C_{3-6}$carbocyclyl, and heterocyclyl:

$R_d$, at each occurrence, is selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r$-heterocyclyl, $-(CH_2)_r$-aryl, $-(CH_2)_r$-heteroaryl, F, Cl, Br, CN, $NO_2$, =O, $-(CH_2)_rOR_f$, $S(O)_pR_f$, $C(=O)NR_fR_f$, $NR_fC(=O)R_d$, $S(O)_pNR_fR_f$, $NR_fS(O)_pR_d$, $NR_fC(=O)OR_d$, $OC(=O)NR_fR_f$ and $-(CH_2)_rNR_fR_f$;

$R_f$ at each occurrence, is independently selected from H, F, Cl, Br, CN, OH, $C_{1-5}$alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2:

r, at each occurrence, is independently selected from zero, 1, 2, 3, and 4.

In another aspect, the present invention provides compounds of Formula (II):

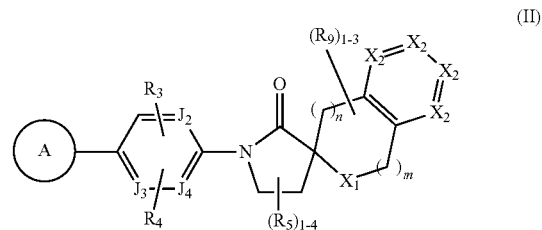

(II)

or stereoisomers, enantiomers, diastereoisomers, tautomers, pharmaceutically acceptable salts, solvates, or prodrugs thereof, wherein Ring A is independently selected from

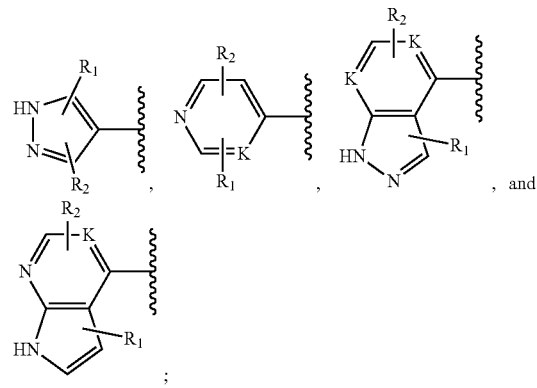

;

$J_2$, $J_3$, and $J_4$ are independently selected from N, $CR_3$, and $CR_4$;

K, at each occurrence, is independently selected from N, $CR_1$, and $CR_2$;

$X_1$ is independently selected from $CR_9R_9$ O, and $NR_8$;

$X_2$ is independently selected from $CR_9$ and N; provided no more than three of $X_2$ are N;

$R_1$, at each occurrence, is independently selected from H, F, Cl, Br, CN, $NR_aR_a$, and $C_{1-4}$alkyl substituted with 0-4 $R_e$;

$R_2$, at each occurrence, is independently selected from H, F, Cl, Br, OH, CN, $NR_aR_a$, and $C_{1-4}$alkyl substituted with 0-4 $R_e$;

$R_3$ is independently selected from H, F, Cl, Br, CN, $C_{1-4}$ alkyl substituted with 0-3 $R_e$, $-(CH_2)_rOR_b$, and $-C_{3-6}$ cycloalkyl;

R$_4$ is independently selected from H, F, Cl, Br, OH, CN, OC$_{1-4}$ alkyl substituted with 0-3 R$_e$, and C$_{1-4}$ alkyl substituted with 0-3 R$_e$;

R$_5$ is independently selected from H, =O, C$_{1-4}$alkyl substituted with 0-4 R$_e$, —(CH$_2$)$_r$OR$_b$, C(=O)R$_b$, and —C(=O)OR$_b$;

R$_8$ is independently selected from H and C$_{1-4}$ alkyl substituted with 0-4 R$_e$;

R$_9$ is independently selected from H, F, Cl, Br, C$_{1-4}$ alkyl, nitro, —(CH$_2$)$_r$S(O)$_p$R$_c$, —(CH$_2$)$_r$S(O)$_p$NR$_a$R$_a$, —(CH$_2$)$_r$NR$_a$S(O)$_p$R$_c$, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —C(=O)NR$_a$R$_a$, —(CH$_2$)$_r$OC(=O)R$_b$, —(CH$_2$)$_r$-cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-4}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-4}$carbocyclyl, and heterocyclyl;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$-heterocyclyl, —(CH$_2$)$_r$-aryl, F, Cl, Br, CN, NO$_2$, =O, CO$_2$H, —(CH$_2$)$_r$OR$_f$, S(O)$_p$R$_f$, S(O)$_p$NR$_f$R$_f$, and —(CH$_2$)$_r$NR$_f$R$_f$;

R$_f$, at each occurrence, is independently selected from H, F, Cl, Br, CN, OH, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl:

m is independently selected from 0 and 1;

n is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (III):

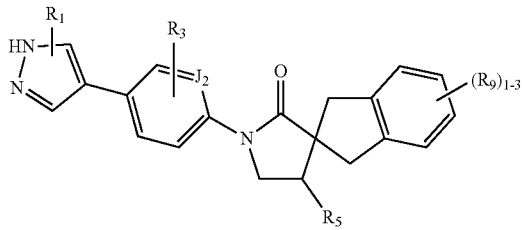

(III)

or stereoisomers, tautomers, pharmaceutically acceptable salts, solvates, or prodrugs thereof, wherein J$_2$ is independently selected from N and CR$_3$;

R$_1$ is independently selected from H and CF;

R$_3$ is independently selected from H, CN, C$_{1-4}$ alkyl, —OC$_{1-3}$ alkyl, and —C$_{3-6}$ cycloalkyl;

R$_5$ is independently selected from H, C$_{1-4}$alkyl substituted with 0-4 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, and —(CH$_2$)$_r$CN;

R$_9$, at each occurrence, is independently selected from H, F, Cl, C$_{1-4}$ alkyl substituted with 0-3 R$_e$, —OR$_b$, CN, C(=O)NR$_a$R$_a$, and heterocyclyl substituted with 0-3 R$_e$;

R$_a$, at each occurrence, is independently selected from H, C$_{1-6}$ alkyl substituted with 0-5 R$_e$, —(CH$_2$)$_r$—C$_{3-6}$ cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_e$, at each occurrence, is independently selected from C$_{1-6}$ alkyl substituted with 0-5 R$_f$, F, Cl, Br, CN, NO$_2$, =O, CO$_2$H, OH, OC$_{1-4}$alkyl, and NR$_f$R$_f$;

R$_f$, at each occurrence, is independently selected from H, F, Cl, Br, CN, OH, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl:

r, at each occurrence, is independently selected from zero, 1, 2, and 3.

In another aspect, the present invention provides compounds of Formula (IV):

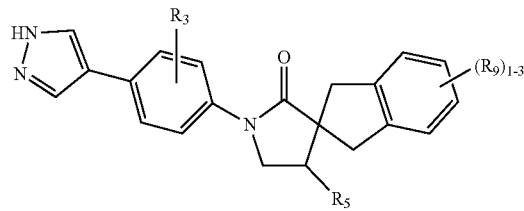

(IV)

or stereoisomers, tautomers, pharmaceutically acceptable salts, solvates, or prodrugs thereof, wherein R$_3$ is independently selected from H, CN, C$_{1-4}$ alkyl, and —OC$_{1-3}$ alkyl;

R$_5$ is independently selected from H, C$_{1-4}$alkyl substituted with 0-4 R$_e$, —(CH$_2$)$_r$OR$_b$, —(CH$_2$)$_r$NR$_a$R$_a$, and —(CH$_2$)$_r$CN;

R$_9$, at each occurrence, is independently selected from H, F, Cl, C$_{1-4}$ alkyl substituted with 0-3 R$_e$, —OR$_b$, CN, C(=O)NR$_a$R$_a$, and heterocyclyl substituted with 0-3 R$_e$:

R$_a$, at each occurrence, is independently selected from H, C$_{1-4}$ alkyl substituted with 0-5 R$_e$, —(CH$_2$)$_r$—C$_{3-6}$ cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$;

R$_b$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$, $R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl; and r, at each occurrence, is independently selected from zero, 1, 2, and 3.

In another aspect, the present invention provides compounds of Formula (V):

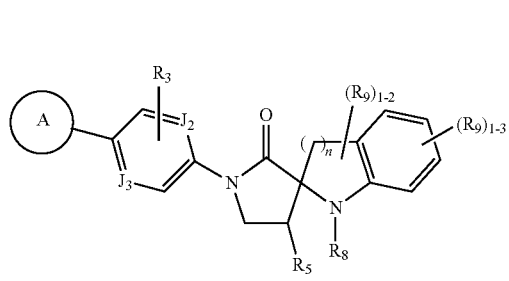

(V)

or stereoisomers, tautomers, pharmaceutically acceptable salts, solvates, or prodrugs thereof, wherein Ring A is independently selected from

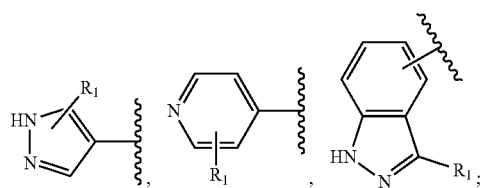

$J_2$ and $J_3$ are independently selected from N and $CR_3$;

$R_1$ is independently selected from H and $CF_3$;

$R_3$ is independently selected from H, CN, $C_{1-4}$ alkyl, $-OC_{1-3}$ alkyl, and $-C_{3-6}$ cycloalkyl;

$R_5$ is independently selected from H, $C_{1-4}$alkyl substituted with 0-4 $R_e$, $-(CH_2)_rOR_b$, $(CH_2)_rS(O)_pR_c$, $-(CH_2)_rC(=O)R_b$, $-(CH_2)_rNR_aR_a$, and $-(CH_2)_rCN$:

$R_8$ is independently selected from H and $C_{1-4}$ alkyl substituted with 0-4 $R_e$;

$R_9$, at each occurrence, is independently selected from H, F, Cl, $C_{1-4}$ alkyl substituted with 0-3 $R_e$, $-OR_b$, CN, $C(=O)NR_aR_a$, and heterocyclyl substituted with 0-3 $R_e$;

$R_a$, at each occurrence, is independently selected from H, $C_{1-4}$ alkyl substituted with 0-5 $R_e$, $-(CH_2)_r-C_{3-6}$ cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_e$, at each occurrence, is independently selected from $C_{1-4}$ alkyl substituted with 0-5 $R_f$, F, Cl, Br, CN, $NO_2$, =O, $CO_2H$, OH, $OC_{1-4}$alkyl, and $NR_fR_f$;

$R_f$, at each occurrence, is independently selected from H, F, Cl, Br, CN. OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl:

n is independently selected from 1 and 2;

r, at each occurrence, is independently selected from zero, 1, 2, and 3.

In another aspect, the present invention provides compounds of Formula (VI):

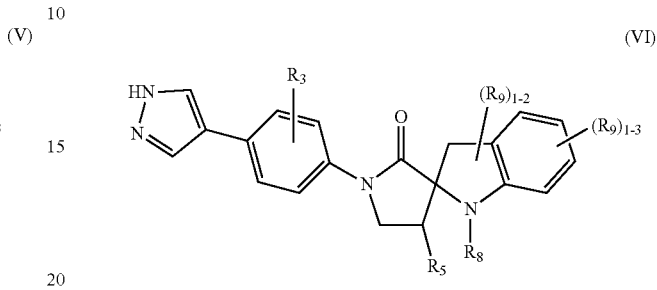

(VI)

or stereoisomers, tautomers, pharmaceutically acceptable salts, solvates, or prodrugs thereof, wherein $R_3$ is independently selected from H, CN, $C_{1-4}$ alkyl, and $-OC_{1-3}$ alkyl;

$R_5$ is independently selected from H, $C_{1-4}$alkyl substituted with 0-4 $R_e$, $-(CH_2)_rOR_b$, $-(CH_2)_rNR_aR_a$, and $-(CH_2)_rCN$;

$R_8$ is independently selected from H and $C_{1-5}$ alkyl substituted with 0-4 $R_e$:

$R_9$, at each occurrence, is independently selected from H, F, Cl, $C_{1-4}$ alkyl substituted with 0-3 $R_e$, $-OR_b$, CN, $C(=O)NR_aR_a$, and heterocyclyl substituted with 0-3 $R_e$;

$R_a$, at each occurrence, is independently selected from H, $C_{1-4}$ alkyl substituted with 0-5 $R_e$, $-(CH_2)_r-C_{3-6}$ cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$:

$R_b$, at each occurrence, is independently selected from H, $C_{1-6}$ alkyl substituted with 0-5 $R_e$, $-(CH_2)_rC_{3-10}$carbocyclyl substituted with 0-5 $R_e$, and $-(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;

r, at each occurrence, is independently selected from zero, 1, 2, and 3.

In another aspect, the present invention provides compounds of Formula (VII):

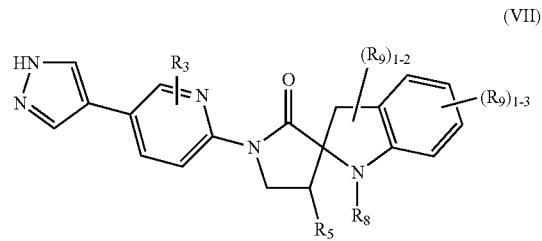

(VII)

or stereoisomers, enantiomers, diastereoisomers, tautomers, pharmaceutically acceptable salts, solvates, or prodrugs thereof, wherein $R_3$ is independently selected from H, CN, $C_{1-4}$ alkyl, and $-OC_{1-3}$ alkyl;

$R_5$ is independently selected from H, $C_{1-4}$alkyl substituted with 0-4 $R_e$, $-(CH_2)_rOR_b$, $-(CH_2)_rNR_aR_a$, and $-(CH_2)_rCN$;

$R_8$ is independently selected from H and $C_{1-4}$ alkyl substituted with 0-4 $R_e$;

$R_9$, at each occurrence, is independently selected from H, F, Cl, $C_4$ alkyl substituted with 0-3 $R_e$, $-OR_b$, CN, C(=O)$NR_aR_a$, and heterocyclyl substituted with 0-3 $R_e$:

$R_a$, at each occurrence, is independently selected from H, $C_{1-6}$ alkyl substituted with 0-5 $R_e$, $-(CH_2)_r-C_{3-6}$ cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;

r, at each occurrence, is independently selected from zero, 1, 2, and 3.

In another aspect, the present invention provides compounds of Formula (VIII):

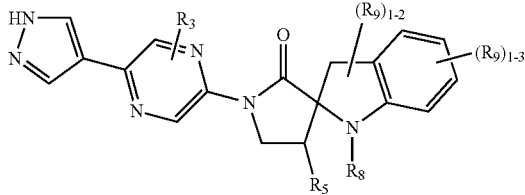

(VIII)

or stereoisomers, enantiomers, diastereoisomers, tautomers, pharmaceutically acceptable salts, solvates, or prodrugs thereof, wherein $R_3$ is independently selected from H, CN, $C_{1-4}$ alkyl, and $-OC_{1-3}$ alkyl;

$R_5$ is independently selected from H, $C_{1-4}$alkyl substituted with 0-4 $R_e$, $-(CH_2)_rOR_b$, $-(CH_2)_rNR_aR_a$, and $-(CH_2)_rCN$;

$R_8$ is independently selected from H and $C_{1-4}$ alkyl substituted with 0-4 $R_e$:

$R_9$, at each occurrence, is independently selected from H, F, Cl, $C_{1-4}$ alkyl substituted with 0-3 $R_e$, $-OR_b$, CN, C(=O)$NR_aR_a$, and heterocyclyl substituted with 0-3 $R_e$;

$R_a$, at each occurrence, is independently selected from H, $C_{1-4}$ alkyl substituted with 0-5 $R_e$, $-(CH_2)_r-C_{3-6}$ cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$:

$R_b$, at each occurrence, is independently selected from H, $C_{1-6}$ alkyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;

r, at each occurrence, is independently selected from zero, 1, 2, and 3.

In another aspect, the present invention provides compounds of Formula (IX):

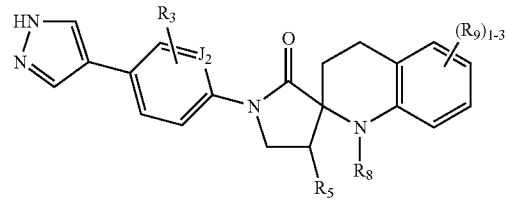

(IX)

or stereoisomers, enantiomers, diastereoisomers, tautomers, pharmaceutically acceptable salts, solvates, or prodrugs thereof, wherein $J_2$ is independently selected from N and $CR_3$:

$R_3$ is independently selected from H, CN, $C_{1-4}$ alkyl, and $-OC_{1-3}$ alkyl;

$R_5$ is independently selected from H, $C_{1-4}$alkyl substituted with 0-4 $R_e$, $-(CH_2)_rOR_b$, $-(CH_2)_rNR_aR_a$, and $-(CH_2)_rCN$;

$R_8$ is independently selected from H and $C_{1-4}$ alkyl substituted with 0-4 $R_e$;

$R_9$, at each occurrence, is independently selected from H, F, Cl, $C_4$ alkyl substituted with 0-3 $R_e$, $-OR_b$, CN, C(=O)$NR_aR_a$, and heterocyclyl substituted with 0-3 $R_e$;

$R_a$, at each occurrence, is independently selected from H, $C_{1-4}$ alkyl substituted with 0-5 $R_e$, $-(CH_2)_r-C_{3-6}$ cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_e$ and $R_e$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;

r, at each occurrence, is independently selected from zero, 1, 2, and 3.

In another aspect, the present invention provides compounds of Formula (X):

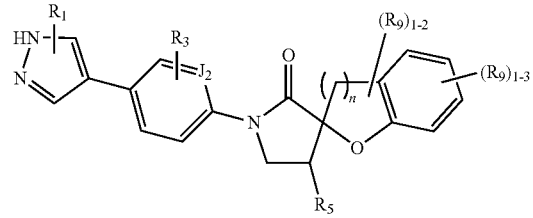

(X)

or stereoisomers, enantiomers, diastereoisomers, tautomers, pharmaceutically acceptable salts, solvates, or prodrugs thereof, wherein $J_2$ is independently selected from N and $CR_3$;
$R_1$ is independently selected from H and $CF_3$;
$R_3$ is independently selected from H, CN, $C_{1-4}$ alkyl, $-OC_{1-3}$ alkyl, and $-C_{3-6}$ cycloalkyl;
$R_5$ is independently selected from H, $C_{1-4}$alkyl substituted with 0-4 $R_e$, $-(CH_2)_rOR_b$, $(CH_2)_rS(O)_pR_c$, $-(CH_2)_rC(=O)R_b$, $-(CH_2)_rNR_aR_a$, and $-(CH_2)_rCN$;
$R_9$, at each occurrence, is independently selected from H, F, Cl, $C_{1-4}$ alkyl substituted with 0-3 $R_e$, $-OR_b$, CN. $C(=O)NR_aR_a$, and heterocyclyl substituted with 0-3 $R_e$;
$R_a$, at each occurrence, is independently selected from H, $C_{1-6}$ alkyl substituted with 0-5 $R_e$, $-(CH_2)_r-C_{3-6}$ cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, Cl, alkyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, $=O$, $CO_2H$, OH, $OC_{1-4}$alkyl, and $NR_fR_f$;
$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl:
n is independently selected from 1 and 2;
r, at each occurrence, is independently selected from zero, 1, 2, and 3.

In another aspect, the present invention provides compounds of Formula (XI):

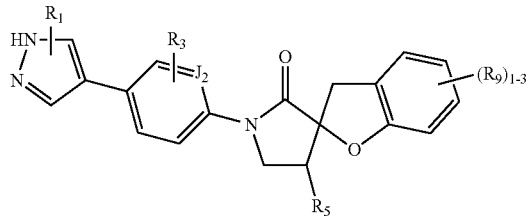

(XI)

or stereoisomers, enantiomers, diastereoisomers, tautomers, pharmaceutically acceptable salts, solvates, or prodrugs thereof, wherein $J_2$ is independently selected from N and $CR_3$;
$R_1$ is independently selected from H and $CF_3$;
$R_3$ is independently selected from H, CN, $C_{1-4}$ alkyl. $-OC_{1-3}$ alkyl, and $-C_{3-6}$ cycloalkyl;
$R_5$ is independently selected from H, $C_{1-4}$alkyl substituted with 0-4 $R_e$, $-(CH_2)_rOR_b$, $(CH_2)_rS(O)_pR_c$, $-(CH_2)_rC(=O)R_b$, $-(CH_2)_rNR_aR_a$, and $-(CH_2)CN$;
$R_9$, at each occurrence, is independently selected from H, F, Cl, $C_{1-4}$ alkyl substituted with 0-3 $R_e$, $-OR_b$, CN, $C(=O)NR_aR_a$, and heterocyclyl substituted with 0-3 $R_e$;
$R_a$, at each occurrence, is independently selected from H, $C_{1-6}$ alkyl substituted with 0-5 $R_e$, $-(CH_2)_r-C_{3-6}$ cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, $=O$, $CO_2H$, OH, $OC_{1-4}$alkyl, and $NR_fR_f$;
$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl:
r, at each occurrence, is independently selected from zero, 1, 2, and 3.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments.

In another aspect, the present invention provides a compound selected from any subset list of compounds exemplified in the present application.

In another embodiment, the compounds of the present invention have ROCK $IC_{50}$ values $\leq 10$ μM.

In another embodiment the compounds of the present invention have ROCK $IC_{50}$ values $\leq 1$ μM.

In another embodiment the compounds of the present invention have ROCK $IC_{50}$ values $\leq 0.5$ μM.

In another embodiment the compounds of the present invention have ROCK $IC_{50}$ values $\leq 0.1$ μM.

In another embodiment the compounds of the present invention have ROCK $IC_{50}$ values $\leq 0.05$ μM.

In another embodiment the compounds of the present invention have ROCK $IC_{50}$ values $\leq 0.01$ μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state. i.e., causing regression of the disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minim/zing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt: a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example, methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example, trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin).

As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc. New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle". "heterocyclyl", or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocyclyl" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", *A Textbook of Drug Design and Development*, pp. 113-191. Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes.

Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl). $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994). Testa, B. et al., *Hydrolysis in Drug and Prodrug Metabolism. Chemistry. Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal. "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight. "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet. "m" for multiplet, "br" for broad, "Hz" for hertz, and "α", "β", "R", "S", "E", and "Z" are stereochemical designations familiar to one skilled in the art.

| | |
|---|---|
| Me | Methyl |
| Et | Ethyl |
| Pr | Propyl |
| i-Pr | Isopropyl |
| Bu | Butyl |
| i-Bu | Isobutyl |
| t-Bu | tert-butyl |
| Ph | Phenyl |
| Bn | Benzyl |
| Boc | tert-butyloxycarbonyl |
| AcOH or HOAc | acetic acid |
| $AlCl_3$ | aluminum chloride |
| AIBN | Azobisisobutyronitrile |
| $BBr_3$ | boron tribromide |
| $BCl_3$ | boron trichloride |
| BEMP | 2-tert-butylimino-2-diethylamino-1,3-dimethylperhydro-1,3,2-diazaphosphorine |
| BOP reagent | benzotriazol-1-yloxytris(dimethylamino)phosphonium hexafluorophosphate |
| Burgess reagent | 1-methoxy-N-triethylammoniosulfonyl-methanimidate |
| CBz | Carbobenzyloxy |
| $CH_2Cl_2$ | Dichloromethane |
| $CH_3CN$ or ACN | Acetonitrile |
| $CDCl_3$ | deutero-chloroform |
| $CHCl_3$ | Chloroform |
| mCPBA or m-CPBA | meta-chloroperbenzoic acid |
| $Cs_2CO_3$ | cesium carbonate |
| $Cu(OAc)_2$ | copper (II) acetate |
| $Cy_2NMe$ | N-cyclohexyl-N-methylcyclohexanamine |
| DBU | 1,8-diazabicyclo[5.4.0]undec-7-ene |
| DCE | 1,2 dichloroethane |
| DCM | dichloromethane |
| DEA | diethylamine |
| Dess-Martin | 1,1,1-tris(acetyloxy)-1,1-dihydro-1,2-beniziodoxol-3-(1H)-one |
| DIC or DIPCDI | diisopropylcarbodiimide |
| DIEA, DIPEA or Hunig's base | diisopropylethylamine |
| DMAP | 4-dimethylaminopyridine |
| DME | 1,2-dimethoxyethane |
| DMF | dimethyl formamide |
| DMSO | dimethyl sulfoxide |
| cDNA | complimentary DNA |
| Dppp | (R)-(+)-1,2-bis(diphenylphosphino)propane |
| DuPhos | (+)-1,2-bis((2S,5S)-2,5-diethylphospholano)benzene |
| EDC | N-(3-dimthylaminopropyl)-N'-ethylcarbodiimide |
| EDCI | N-(3-dimthylaminopropyl)-N'-ethylcarbodiimide hydrochloride |
| EDTA | ethylenediaminetetraacetic acid |
| (S,S)-EtDuPhosRh(I) | (+)-1,2-bis((2S,5S)-2,5-diethylphospholano)benzene(1,5-cyclooctadiene)rhodium(I) trifluoromethanesulfonate |
| $Et_3N$ or TEA | triethylamine |
| EtOAc | ethyl acetate |
| $Et_2O$ | diethyl ether |
| EtOH | Ethanol |
| GMF | glass microfiber filter |
| Grubbs (II) | (1,3-bis(2,4,6-trimethylphenyl)-2-imidazolidinylidene)dichloro(phenylmethylene)(triycyclohexylphosphine)ruthenium |
| HCl | hydrochloric acid |
| HATU | O-(7-azabenzotriazol-1-yl)-N,N,N',N'-tetramethyluronium hexafluorophosphate |
| HEPES | 4-(2-hydroxyethyl)piperaxine-1-ethanesulfonic acid |
| Hex | Hexane |
| HOBt or HOBT | 1-hydroxybenzotriazole |
| $H_2SO_4$ | sulfuric acid |
| $K_2CO_3$ | potassium carbonate |
| KOAc | potassium acetate |
| $K_3PO_4$ | potassium phosphate |
| LAH | lithium aluminum hydride |
| LG | leaving group |
| LiOH | lithium hydroxide |
| MeOH | Methanol |
| $MgSO_4$ | magnesium sulfate |
| MsOH or MSA | methylsulfonic acid |
| NaCl | sodium chloride |
| NaH | sodium hydride |
| $NaHCO_3$ | sodium bicarbonate |
| $Na_2CO_3$ | sodium carbonate |
| NaOH | sodium hydroxide |
| $Na_2SO_3$ | sodium sulfite |

-continued

| | |
|---|---|
| NH₂SO₄ | sodium sulfate |
| NBS | N-bromosuccinimide |
| NCS | N-chlorosuccinimide |
| NH₃ | Ammonia |
| NH₄Cl | ammonium chloride |
| NH₄OH | ammonium hydroxide |
| OTf | triflate or trifluoromethanesulfonate |
| Pd₂(dba)₃ | tris(dibenzylideneacetone)dipalladium(0) |
| Pd(OAc)₂ | palladium(II) acetate |
| Pd/C | palladium on carbon |
| Pd(dppf)Cl₂ | [1,1'-bis(diphenylphosphino)-ferrocene]dichloropalladium(II) |
| Ph₃PCl₂ | triphenylphosphine dichloride |
| PG | protecting group |
| POCl₃ | phosphorus oxychloride |
| i-PrOH or IPA | isopropanol |
| PS | polystyrene |
| PyBOP | benzotriazol-1-yl-oxytripyrrolidinophosphonium hexafluorophosphate |
| SEM-Cl | 2-(trimethysilyl)ethoxymethyl chloride |
| 2nd generation XPhos precatalyst | Chloro(2-dicyclohexylphosphino-2',4',6'-triisopropyl-1,1' biphenyl)[2-(2'-amino-1,1'-biphenyl)]palladium(II), THF adduct |
| SiO₂ | silica oxide |
| SnCl₂ | tin(II) chloride |
| TBAI | tetra-n-butylammonium iodide |
| TEA | triethylamine |
| TFA | trifluoroacetic acid |
| THF | tetrahydrofuran |
| TMSCHN₂ | trimethylsilyldiazomethane |
| T3P ® | propane phosphonic acid anhydride |
| TRIS | tris (hydroxymethyl) aminomethane |

The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL assay containing 20 mM HEPES, pH 7.5, 20 mM MgCl₂, 0.015% Brij-35, 4 mM DTT, 5 μM ATP and 1.5 μM peptide substrate (FITC-AHA-AKRRRLSSLRA-OH) (SEQ ID NO.1). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LAB-CHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the $IC_{50}$; i.e., the concentration of compound required to inhibit 50% of kinase activity.

Representative Examples were tested in the ROCK2 assay described above and found having ROCK2 inhibitory activity. Their ROCK2 inhibitory activity ($IC_{50}$ values) of ≤2 μM (2000 nM) was observed and shown in Table A below. The ranges of the ROCK2 $IC_{50}$ values are as follows: ROCK2 $IC_{50}$: ++++ (<3 nM) +++ (3-30 nM) ++ (30-300 nM) + (300-2000 nM)

TABLE A

| Example No. | ROCK2 $IC_{50}$ |
|---|---|
| 1 | + |
| 1 | ++++ |
| 2 | ++++ |
| 3 | ++ |
| 4 | ++++ |
| 5 | ++++ |
| 6 | +++ |
| 7 | +++ |
| 8 | +++ |
| 9 | ++ |
| 10 | ++++ |
| 11 | +++ |
| 12 | ++ |
| 13 | +++ |
| 14 | ++ |
| 15 | +++ |
| 16 | +++ |
| 17 | ++++ |
| 18 | +++ |
| 19 | + |
| 20 | ++++ |
| 22 | ++++ |
| 23 | ++++ |
| 24 | ++++ |
| 25 | ++ |
| 26 | ++++ |
| 27 | +++ |
| 28 | ++ |
| 29 | ++++ |
| 30 | ++ |
| 31 | ++++ |
| 32 | ++++ |
| 33 | ++ |
| 34 | ++++ |
| 35 | +++ |
| 36 | ++ |
| 37 | ++++ |
| 38 | ++++ |
| 39 | + |
| 40 | ++++ |
| 41 | +++ |
| 42 | ++++ |
| 43 | ++ |
| 44 | +++ |
| 45 | +++ |
| 46 | +++ |
| 47 | ++++ |
| 48 | ++ |
| 49 | +++ |
| 50 | ++ |
| 51 | ++++ |
| 52 | ++++ |
| 53 | ++++ |
| 54 | ++++ |
| 55 | ++ |
| 56 | ++++ |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated, the patient to which the agent-containing composition is to be administered: the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration: the species, age, sex, health, medical condition, and weight of the recipient; the nature and extent of the symptoms; the kind of concurrent treatment: the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example, as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container: (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand. J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below.

The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*. 4th Edition, Wiley-Interscience (2006)).

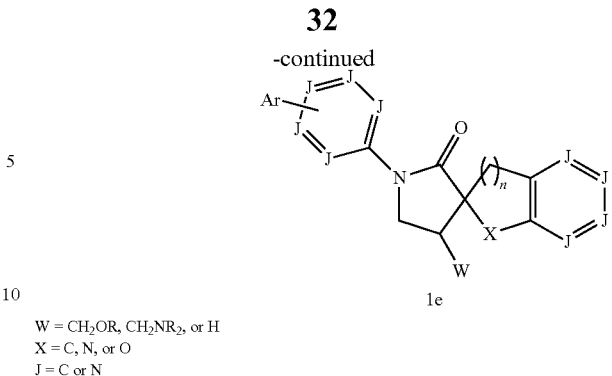

W = $CH_2OR$, $CH_2NR_2$, or H
X = C, N, or O
J = C or N

Scheme 1 describes the method used to synthesize spirolactam analogs bearing a substituent in the β-position of the lactam. An appropriately substituted allyl ester, 1a, is subjected to base and elevated temperature to affect a Claisen rearrangement. The subsequent carboxylic acid is then esterified to 1b under standard conditions (e.g. TMS-diazomethane). The olefin in 1b then undergoes oxidative cleavage and reductive amination with a bromoaniline to yield 1c. Under basic conditions, 1c is the converted to lactam 1d. The final analogs of the structure 1e are formed by Suzuki coupling of the aryl bromide and removal of any protective groups.

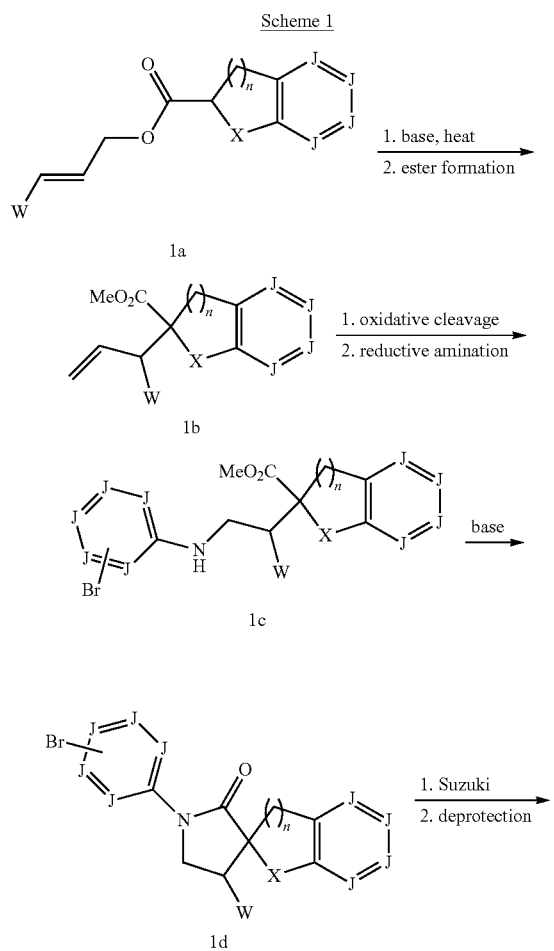

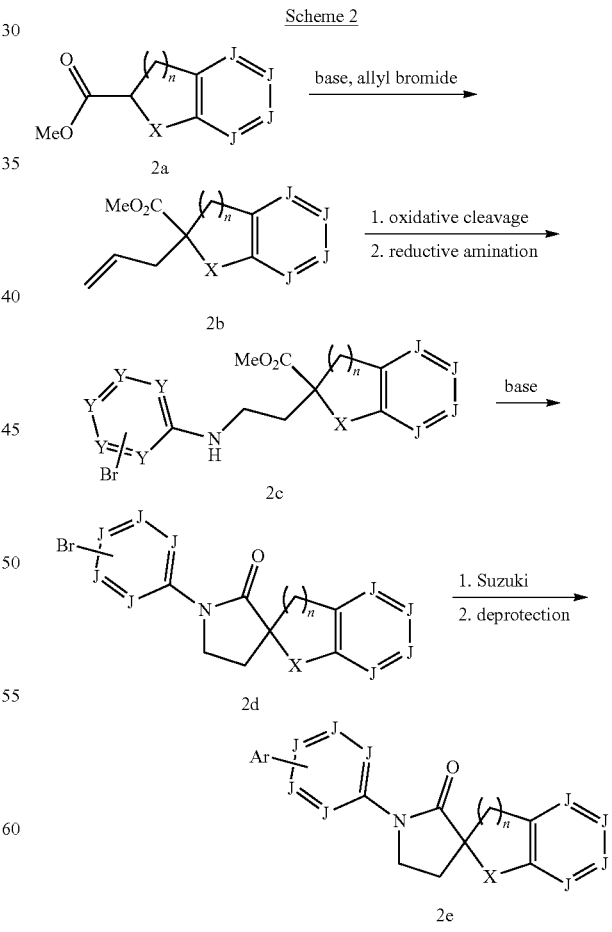

X = C, N, or O
J = C or N

Scheme 2 describes a synthesis of analogs with no substitution on the lactam ring. Ester 2a is treated with base then allyl bromide to yield allylated ester 2b. The remainder of the synthesis from 2b to 2e is analogous to the synthesis of 1e from 1b.

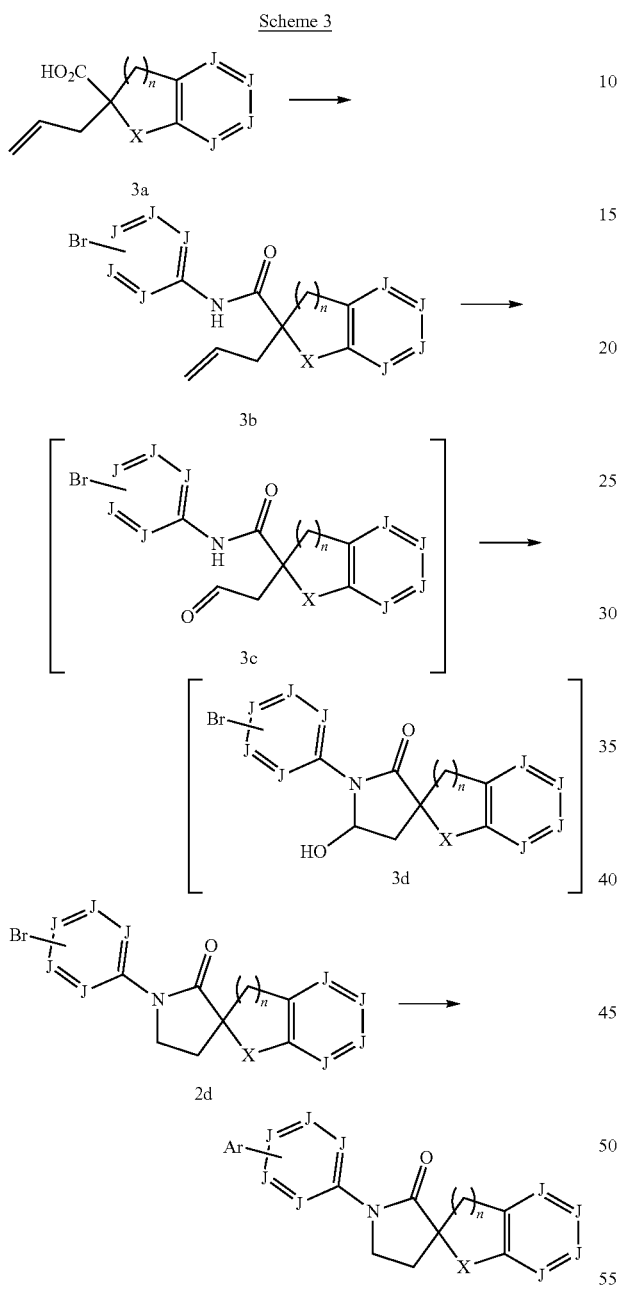

X = C, N, or O
J = C or N

Scheme 3 describes an alternative synthetic route to analogs 2e. Allylated acid 3a undergoes amide formation with a bromoaniline to form allylated amide 3b. Oxidative cleavage of 3b yields intermediate aldehyde 3c which is trapped by the pendant amide to generate hemiaminal 3d. Reduction of this transient species affords lactam 2d. The final products 2e are synthesized in a manner analogous to that described for Scheme 1.

Purification of intermediates and final products was carried out via either normal or reverse phase chromatography. Normal phase chromatography was carried out using pre-packed $SiO_2$ cartridges eluting with either gradients of hexanes and EtOAc or DCM and MeOH unless otherwise indicated. Reverse phase preparative HPLC was carried out using C18 columns eluting with gradients of Solvent A (90% $H_2O$, 10% MeOH, 0.1% TFA) and Solvent B (10% $H_2O$, 90% MeOH, 0.1% TFA, UV 220 nm) or with gradients of Solvent A (90% $H_2O$, 10% ACN, 0.1% TFA) and Solvent B (10% $H_2O$, 90% ACN, 0.1% TFA, UV 220 nm) or with gradients of Solvent A (98% $H_2O$, 2% ACN, 0.05% TFA) and Solvent B (98% ACN, 2% $H_2O$, 0.05% TFA, UV 220 nm) (or) Sunfire Prep C18 OBD 5u 30×100 mm, 25 min gradient from 0-100% B. A=$H_2O$/ACN/TFA 90:10:0.1. B=ACN/$H_2O$/TFA 90:10:0.1 (or) Waters XBridge C18, 19×200 mm, 5-µm particles; Guard Column: Waters XBridge C18, 19×10 mm, 5-µm particles; Solvent A: water with 20-mM ammonium acetate; Solvent B: 95:5 acetonitrile:water with 20-mM ammonium acetate; Gradient: 25-65% B over 20 minutes, then a 5-minute hold at 100% B; Flow: 20 mL/min.

Unless otherwise stated, analysis of final products was carried out by reverse phase analytical HPLC.

Method A:
Sunfire C18 column (3.5 µm C18, 3.0×150 mm). Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method B:
XBridge Phenyl column (3.5 µm C18, 3.0×150 mm). Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method C:
Waters BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes; Flow: 1.11 mL/min.

Method D:
Waters BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.11 mL/min.

Example 1

1'-(4-(1H-Pyrazol-4-yl)phenyl)spiro[indoline-2,3'-pyrrolidin]-2'-one, Racemic

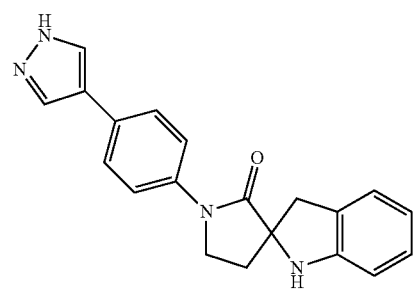 [SMILES: O=C1N(c2ccc(-c3cn[nH]c3)cc2)CCC12Cc1ccccc1N2]

Example 1A. Methyl indoline-2-carboxylate

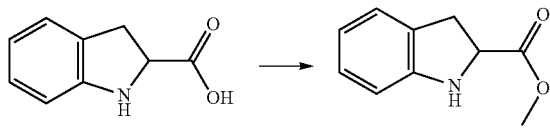

To a solution of indoline-2-carboxylic acid (5 g, 12.26 mmol) in MeOH (40 mL) was added sulfuric acid (2.45 mL, 46.0 mmol) dropwise. The reaction was heated at 80° C. for 18 h then cooled in ice bath, neutralized with 1.5M $K_2HPO_4$, extract with EtOAc (3×). The combined organic layers were washed with sat. $NaHCO_3$, brine, dried with $MgSO_4$ and concentrated to give methyl indoline-2-carboxylate (5.17 g, 95% yield) as brown oil which was used in the next step without further purification. MS(ESI) nm/z: 178.0 (M+H)$^+$. $^1$H NMR (400 MHz, CDCl$_3$) δ 7.11-7.00 (m, 2H), 6.77-6.68 (m, 2H), 4.39 (dd, J=10.1, 5.5 Hz, 1H), 3.75 (s, 3H), 3.44-3.25 (m, 2H).

Example 1B. 1-Tert-butyl 2-methyl indoline-1,2-dicarboxylate

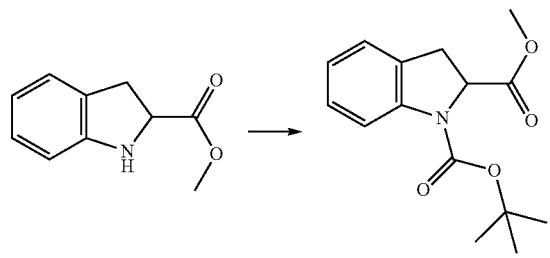 [SMILES: COC(=O)C1Cc2ccccc2N1 ; COC(=O)C1Cc2ccccc2N1C(=O)OC(C)(C)C]

To a solution of methyl indoline-2-carboxylate (5.17 g, 29.2 mmol) in $CH_2Cl_2$ (50 mL) was added BOC-anhydride (10.84 mL, 46.7 mmol) in portions. The reaction was stirred at rt o.n, concentrated and purified by normal phase chromatography to give 1-tert-butyl 2-methyl indoline-1,2-dicarboxylate (7.2 g, 89% yield) as a white solid. MS(ESI) m/z: 178.0 (M+H-Boc)$^+$. $^1$H NMR (400 MHz, CDCl$_3$) δ 7.89 (br. s., 0.6H), 7.64-7.40 (m, 0.4H), 7.19 (t, J=7.7 Hz, 1H), 7.11 (d, J=7.3 Hz, 1H), 6.97-6.90 (m, 1H), 4.87 (br. s., 1H), 3.75 (s, 3H), 3.51 (dd, J=16.4, 11.6 Hz, 1H), 3.11 (dd, J=16.6, 4.5 Hz, 1H), 1.67-1.43 (m, 9H) diasteromers.

Example 1C. 1-Tert-butyl 2-methyl 2-allylindoline-1,2-dicarboxylate

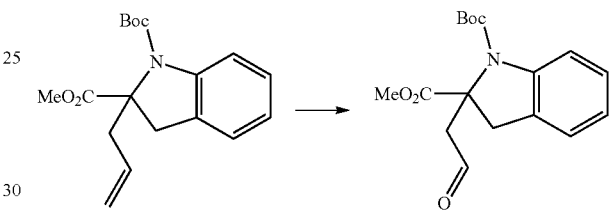

To a solution of 1-tert-butyl 2-methyl indoline-1,2-dicarboxylate (2 g, 7.21 mmol) in THF (30 mL) was added NaHMDS 1M in THF (14.42 mL, 14.42 mmol) dropwise via a syringe (10 min). The mixture was stirred at −30° C. for 30 min., recooled to −78° C. and allyl bromide (1.997 mL, 23.08 mmol) was added slowly. The ice bath was removed and the reaction was stirred at rt for 2 h, quenched with sat $NH_4Cl$, and extracted with EtOAc (2×). The combined organic layers were concentrated then purified by normal phase chromatography to give 1-tert-butyl 2-methyl 2-allylindoline-1,2-dicarboxylate (1.36 g, 59% yield) as a yellow oil. MS(ESI) m/z: 318.1 (M+H)$^+$. $^1$H NMR (400 MHz, CDCl$_3$) δ 7.89 (br. s., 0.57H), 7.59-7.36 (m, 0.27H), 7.18 (t, J=7.7 Hz, 1H), 7.10-7.02 (m, 1H), 6.98-6.90 (m, 1H), 5.63 (ddt, J=17.1, 9.8, 7.3 Hz, 1H), 5.13 (dd, J=17.1, 1.9 Hz, 1H), 5.01 (d, J=9.9 Hz, 1H), 3.74 (s, 3H), 3.42-3.15 (m, 2H), 3.10 (br. s., 1H), 2.79-2.61 (m, 1H), 1.70-1.41 (m, 9H) rotamers.

Example 1D. 1-Tert-butyl 2-methyl 2-(2-oxoethyl)indoline-1,2-dicarboxylate

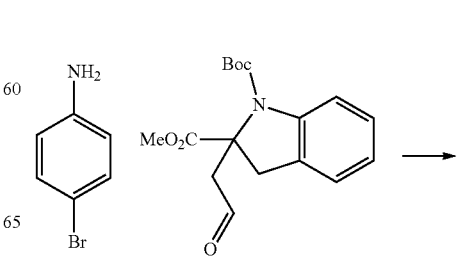

To a solution of 1-tert-butyl 2-methyl 2-allylindoline-1,2-dicarboxylate (1.36 g, 4.29 mmol) in MeOH (60 mL) and water (30 mL) was added osmium tetroxide (2.5% in tBuOH) (3.77 mL, 0.300 mmol). After 5 min, sodium periodate (2.75 g, 12.86 mmol) was added in 3 batches over 5 min. After 2 h. water was added and the reaction was extracted with EtOAc (2×). The combined organic layers were washed with water, brine, concentrated and purified by normal phase chromatography to give 1-tert-butyl 2-methyl 2-(2-oxoethyl)indoline-1,2-dicarboxylate (1.02 g, 75% yield) as a grey oil. MS(ESI) m/z: 220.0 (M+H-Boc)$^+$. $^1$H NMR (400 MHz, CDCl$_3$) δ 9.82 (br. s., 1H), 8.03-7.35 (m, 1H), 7.22 (t, J=7.7 Hz, 1H), 7.13 (d, J=7.3 Hz, 1H), 7.05-6.91 (m, 1H), 3.81-3.72 (m, 3H), 3.59-3.45 (m, 1H), 3.36 (d, J=15.2 Hz, 1H), 3.22 (dd, J=15.4, 3.3 Hz, 1H), 3.00 (br. s., 1H), 1.55 (d, J=7.5 Hz, 9H) rotamers

Example 1E. 1-Tert-butyl 2-methyl 2-(2-((4-bromophenyl)amino)ethyl)indoline-1,2-dicarboxylate -continued

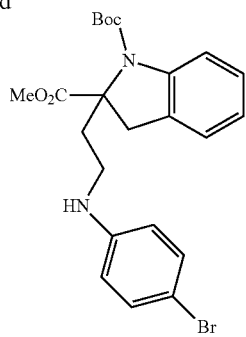

A solution of 1-tert-butyl 2-methyl 2-(2-oxoethyl)indoline-1,2-dicarboxylate (0.8 g, 2.505 mmol) and 4-bromoaniline (0.431 g, 2.505 mmol) in MeOH (6 mL) was stirred at rt for 30 min. NaBH$_3$CN (1M in THF) (5.0 mL, 5.0 mmol) was added. The reaction was stirred at rt o.n, quenched with 1 N NaOH, and extracted EtOAc (2×). The combined organic layers were concentrated and purified on reverse phase chromatography.

The desired product fractions were concentrated then free based using sat NaHCO$_3$, and extracted with EtOAc (3×). The combined organic layers were washed with brine, dried with MgSO$_4$ and concentrated to give 1-tert-butyl 2-methyl 2-(2-((4-bromophenyl)amino)ethyl)indoline-1,2-dicarboxylate (617 mg, 52% yield) as a pink foam. MS(ESI) m/z: 476.9 (M+H)$^+$. $^1$H NMR (400 MHz. CDCl$_3$) 7.94 (br. s., 1H), 7.25-7.16 (m, 3H), 7.10 (d, J=7.0 Hz, 1H), 7.03-6.89 (m, 1H), 6.40-6.32 (m, 2H), 3.74 (s, 3H), 3.45 (d, J=16.7 Hz, 1H), 3.22-3.07 (m, 4H), 2.66 (br. s., 1H), 2.22 (dt, J=14.1, 6.8 Hz, 1H), 1.68-1.34 (m, 9H) rotamers.

Example 1F. Tert-butyl 1'-(4-bromophenyl)-2'-oxospiro[indoline-2,3'-pyrrolidine]-1-carboxylate, Racemic

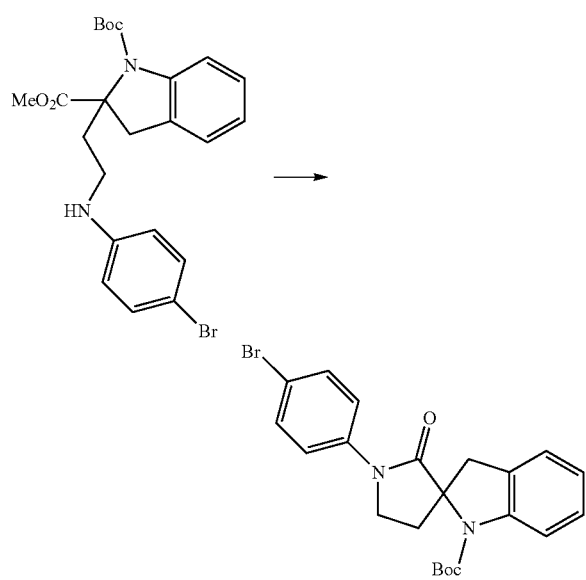

A pressure vial was charged with a solution of 1-tert-butyl 2-methyl 2-(2-((4-bromophenyl)amino)ethyl)indoline-1,2-dicarboxylate (57 mg, 0.120 mmol) in THF (1 mL) and sodium hydride (10 mg, 0.25 mmol) under N$_2$. The vial was capped and the reaction was heated at 65° C. o.n. The mixture was diluted with EtOAc, quenched with water and extracted with EtOAc (2×). The combined organic layers were concentrated and purified by normal phase chromatography to give tert-butyl 1'-(4-bromophenyl)-2'-oxospiro[indoline-2,3'-pyrrolidine]-1-carboxylate (30 mg, 56% yield) as a red film. MS(ESI) m/z: 389.1 (M+H-tBu)$^+$.

Example 1G. Tert-butyl 1'-(4-bromophenyl)-2'-oxospiro[indoline-2,3-pyrrolidine]-1-carboxylate, peak 1 and tert-butyl 1'-(4-bromophenyl)-2'-oxospiro[indoline-2,3'-pyrrolidine]-1-carboxylate, Peak 2

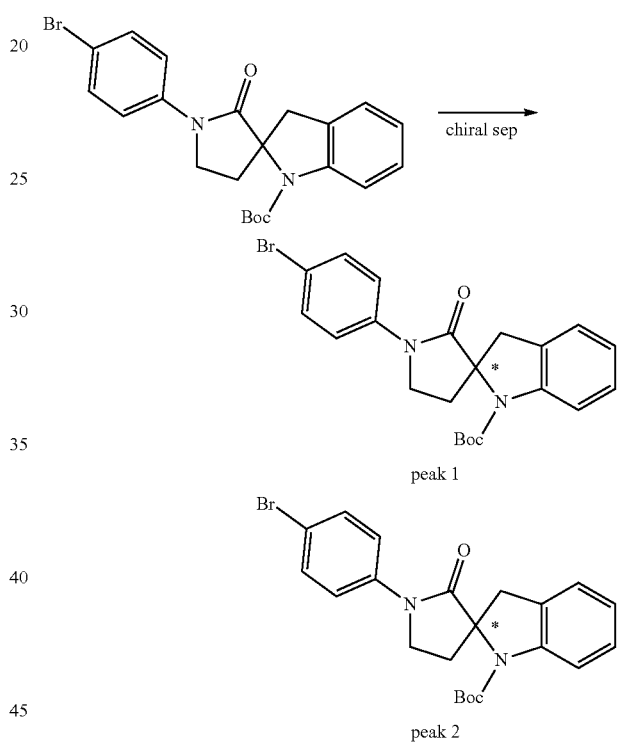

Chiral separation of tert-butyl 1'-(4-bromophenyl)-2'-oxospiro[indoline-2,3'-pyrrolidine]-1-carboxylate, racemic on 400 mg gave peak 1 (191 mg) as a white solid (analytical RT 6.039 min) and peak 2 (192 mg) as a white solid (analytical RT 9.26 min).

Analytical chiral chromatographic condition:

Chiralpak IC, 4.6×250 mm, 5 micron. Mobile phase: 20% MeOH/80% CO$_2$.

Flow:

2.0 mL/min, 150 Bar, 40° C.

Preparative chiral chromatographic condition:

Chiralpak IC, 21×250 mm, 5 micron. Mobile phase: 20% MeOH/80% CO$_2$.

Flow:

45 mL/min, 100 Bar, 40° C.

Example 1

1'-(4-(1H-Pyrazol-4-yl)phenyl)spiro[indoline-2,3'-pyrrolidin]-2'-one, Racemic

Example 2

1'-(4-(1H-Pyrazol-4-yl)phenyl)spiro[indoline-2,3'-pyrrolidin]-2'-one, "Enantiomer 1"

and

Example 3

1'-(4-(H-Pyrazol-4-yl)phenyl)spiro[indoline-2,3'-pyrrolidin]-2'-one ("Enantiomer 2")

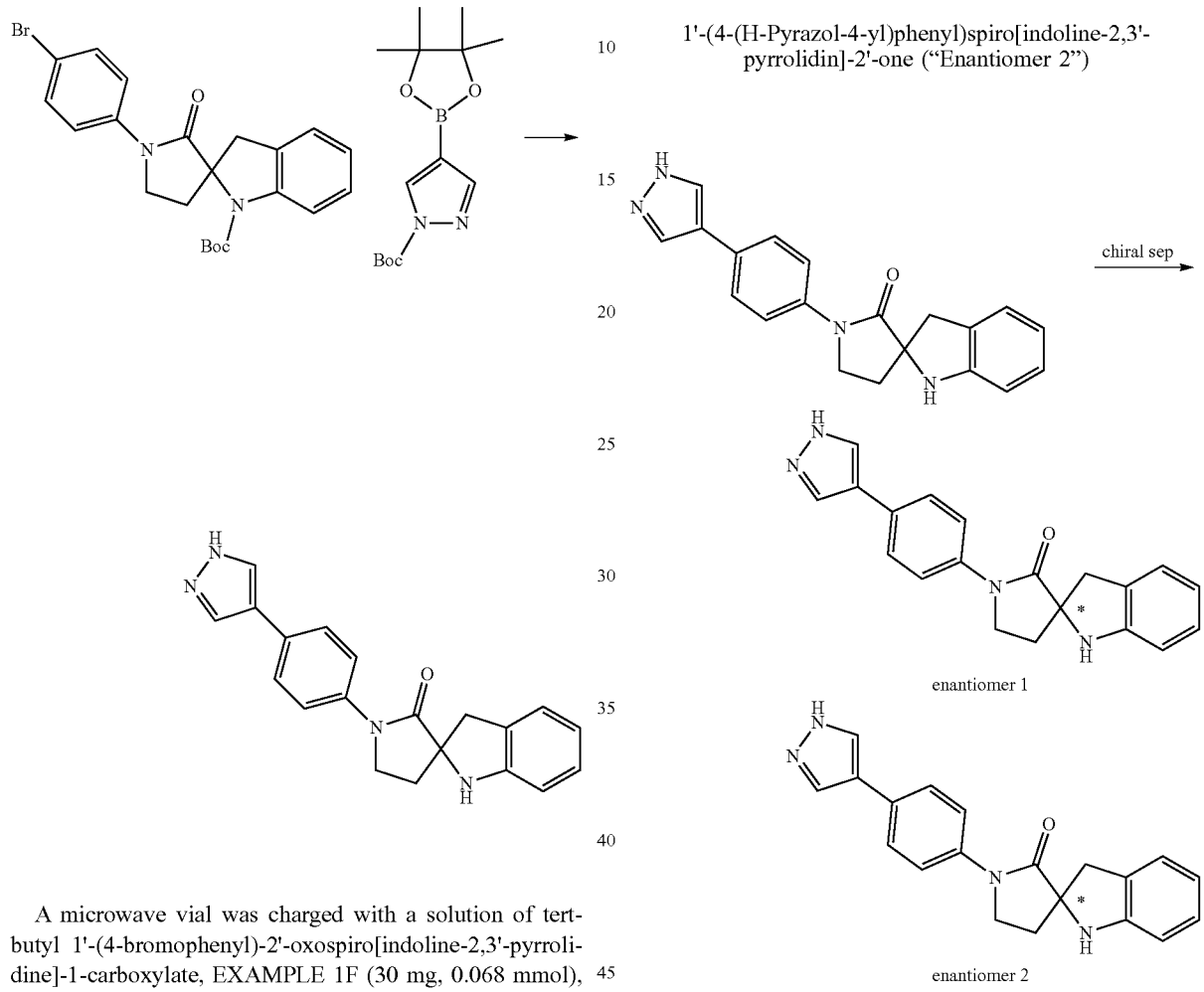

A microwave vial was charged with a solution of tert-butyl 1'-(4-bromophenyl)-2'-oxospiro[indoline-2,3'-pyrrolidine]-1-carboxylate, EXAMPLE 1F (30 mg, 0.068 mmol), tert-butyl 4-(4,4,5,5-tetramethyl-1,3,2-dioxaborolan-2-yl)-1H-pyrazole-1-carboxylate (30 mg, 0.102 mmol) in THF (2.0 mL) and phosphoric acid, potassium salt (3 M aq.) (0.11 mL, 0.34 mmol) was purged with $N_2$. Pd-XPhos G3 (1 mg, 1.181 μmol) was added. The vial was capped, and heated at 90° C. for 1 h then microwaved at 120° C. for 45 min. The reaction was cooled to rt, extracted with EtOAc. The organic layer was concentrated then the residue was dissolved and stirred in $CH_2Cl_2$ (2 mL) and TFA (1 mL) for 0.5 h at rt. The mixture was concentrated to dryness and purified by reverse phase chromatography to give 1'-(4-(1H-pyrazol-4-yl)phenyl)spiro[indoline-2,3'-pyrrolidin]-2'-one (5.9 mg, 16% yield). HPLC: METHOD C, RT 1.59 min. Purity 100%. MS(ESI) m/z: 331.0 (M+H)$^+$. $^1$H NMR (500 MHz, DMSO-$d_6$) δ 8.14 (br. s., 1H), 7.94 (br. s., 1H), 7.76-7.68 (m, 2H), 7.65 (d, J=8.5 Hz, 2H), 7.01 (d, J=7.0 Hz, 1H), 6.95 (t, J=7.6 Hz, 1H), 6.56 (t, J=7.3 Hz, 1H), 6.49 (d, J=7.6 Hz, 1H), 3.93-3.75 (m, 2H), 3.47-3.37 (m, 1H), 3.29-3.17 (m, 1H), 3.08 (d, J=16.2 Hz, 1H), 2.34-2.14 (m, 2H)

Prepared by chiral separation of racemic 1'-(4-(1H-pyrazol-4-yl)phenyl)spiro[indoline-2,3'-pyrrolidin]-2'-one, EXAMPLE 1, using Chiralpak IB, 21×250 mm, 5 micron; eluting with 40% MeOH/60% $CO_2$. Flow 45 mL/min, 150 Bar, 40° C. gave 2 peaks. The first peak, 1'-(4-(H-pyrazol-4-yl)phenyl)spiro[indoline-2,3'-pyrrolidin]-2'-one ("enantiomer 1"), EXAMPLE 2 (17.9 mg) as a tan solid. MS(ESI) m/z: 331.2 (M+H)$^+$
$^1$H NMR (500 MHz, DMSO-$d_6$) δ 12.91 (br. s., 1H), 8.17 (br. s., 1H), 7.91 (br. s., 1H), 7.85-7.52 (m, 4H), 7.13-6.81 (m, 2H), 6.65-6.39 (m, 2H), 6.31 (br. s., 1H), 4.07-3.66 (m, 2H), 3.22 (d. J=16.0 Hz, 1H), 3.07 (d, J=16.0 Hz, 1H), 2.35-2.04 (m, 2H)

HPLC: Method A, RT 6.01 min, 98.5% purity; Method B, RT 7.65 min, 99% purity Enantiomeric excess >99.0%, RT 6.77 min. Analytical chiral chromatographic condition: Chiralpak IB, 4.6×250 mm, 5 micron. Mobile phase: 40% MeOH/60% $CO_2$. Flow: 2.0 mL/min, 150 Bar, 40° C.

The second peak 1'-(4-(1H-pyrazol-4-yl)phenyl)spiro[indoline-2,3'-pyrrolidin]-2'-one ("enantiomer 2"), EXAMPLE 3 (19.6 mg) as a tan solid. MS(ESI) m/z: 331.2 (M+H)$^+$ $^1$H NMR (500 MHz, DMSO-d$_6$) δ 12.91 (br. s., 1H), 8.17 (br. s., 1H), 7.91 (br. s., 1H), 7.86-7.44 (m, 4H), 7.22-6.78 (m, 2H), 6.66-6.40 (m, 2H), 6.31 (br. s., 1H), 4.02-3.65 (m, 2H), 3.08 (br. s., 1H), 2.36-2.05 (m, 2H). HPLC: Method A, RT 5.95 min, 99.5% purity; Method B, RT 7.59 min, 99.3% purity. Enantiomeric excess >99.0%, RT 9.15 min.

Analytical chiral chromatographic condition: Chiralpak IB, 4.6×250 mm, 5 micron. Mobile phase: 40% MeOH/60% CO$_2$. Flow: 2.0 mL/min, 150 Bar, 40° C. Alternatively, EXAMPLE 2. 1'-(4-(1H-Pyrazol-4-yl)phenyl)spiro[indoline-2,3'-pyrrolidin]-2'-one, "enantiomer 1" and EXAMPLE 3. 1'-(4-(1H-Pyrazol-4-yl)phenyl)spiro[indoline-2,3'-pyrrolidin]-2'-one ("enantiomer 2") can be synthesized as follow, Example 2

1'-(4-(1H-Pyrazol-4-yl)phenyl)spiro[indoline-2,3'-pyrrolidin]-2'-one, "Enantiomer 1"

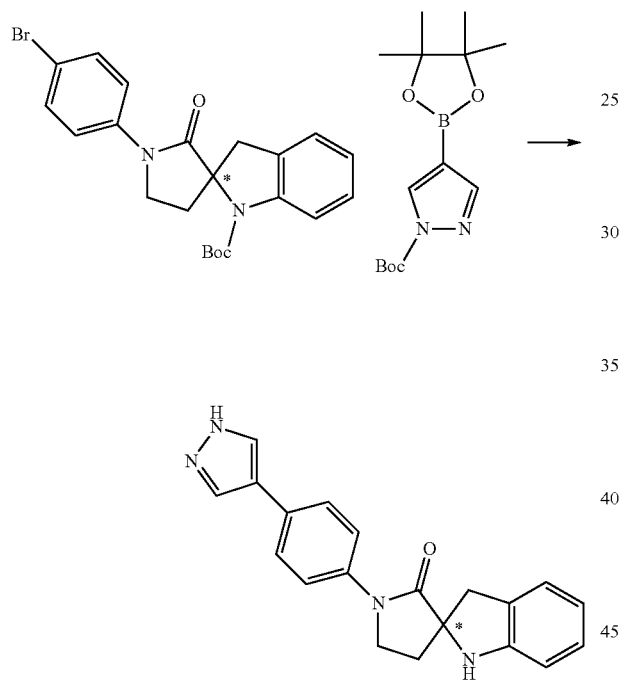

A microwave vial was charged with a solution of tert-butyl 1'-(4-bromophenyl)-2'-oxospiro[indoline-2,3'-pyrrolidine]-1-carboxylate (80 mg, 0.180 mmol), EXAMPLE 1G Peak 2, tert-butyl 4-(4,4,5,5-tetramethyl-1,3,2-dioxaborolan-2-yl)-1H-pyrazole-1-carboxylate (80 mg, 0.271 mmol) in dioxane (5.0 mL) and phosphoric acid, potassium salt (3 M aq.) (0.30 mL, 0.90 mmol) was purged with argon. Pd-XPhos G3 (5 mg, 5.91 μmol) was added. The vial was capped, and the reaction mixture was microwaved at 120° C. for 45 min. The reaction was cooled to rt, extracted with EtOAc. The organic layer was concentrated then purified by normal phase chromatography to give a mixture of the bis and mono Boc products as a white solid (93 mg).

The solid was dissolved and stirred in CH$_2$C$_2$ (1 mL) and TFA (1 mL, 12.98 mmol) for 0.5 h at rt. The mixture was concentrated to dryness and MeOH was added to precipitate the desired product. The solid was filtered and washed with methanol to give 1'-(4-(1H-Pyrazol-4-yl)phenyl)spiro[indoline-2,3'-pyrrolidin]-2'-one, EXAMPLE 2 (48 mg, 79% yield) as a beige solid. MS(ESI) m/z: 331.1 (M+H)$^+$. $^1$H NMR (400 MHz, DMSO-d$_6$) δ 8.19 (br. s., 1H), 7.93 (br. s., 1H), 7.79-7.70 (m, 2H), 7.70-7.58 (m, 2H), 7.01 (d, J=7.3 Hz, 1H), 6.95 (t, J=7.6 Hz, 1H), 6.56 (t, J=7.4 Hz, 1H), 6.49 (d, J=7.7 Hz, 1H), 6.33 (s, 1H), 3.96-3.74 (m, 2H), 3.27-3.04 (m, 2H), 2.32-2.14 (m, 2H). HPLC: Method A, RT=6.39 min, 98.3% purity; Method B, RT=8.14 min, 99.5% purity. Enantiomeric excess >99.0%, RT 6.80 min. Analytical chiral chromatographic condition: Chiralpak IB, 4.6×250 mm, 5 micron. Mobile phase: 35% MeOH/65% CO$_2$. Flow: 2.0 mL/min. 150 Bar, 40° C.

Example 3

1'-(4-(1H-Pyrazol-4-yl)phenyl)spiro[indoline-2,3'-pyrrolidin]-2'-one ("Enantiomer 2")

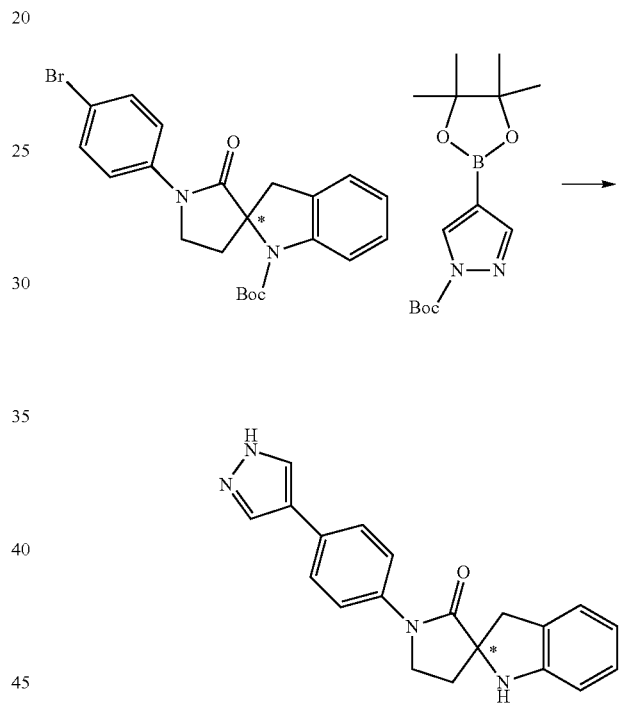

Prepared using a procedure analogous to EXAMPLE 2 (alternative) except that tert-butyl 1'-(4-bromophenyl)-2'-oxospiro[indoline-2,3'-pyrrolidine]-1-carboxylate, EXAMPLE 1G Peak 2 was replaced with tert-butyl 1'-(4-bromophenyl)-2'-oxospiro[indoline-2,3'-pyrrolidine]-1-carboxylate, EXAMPLE 1G Peak 1 to give 1'-(4-(1H-pyrazol-4-yl)phenyl)spiro[indoline-2,3'-pyrrolidin]-2'-one, EXAMPLE 3 (48 mg, 79% yield) as an off white solid. MS(ESI) m/z: 331.1 (M+H)$^+$.

HPLC: Method A, RT=6.41 min, 98.2% purity; Method B, RT=8.18 min, 98.3% purity. $^1$H NMR (400 MHz, DMSO-d$_6$) δ 8.06 (br. s., 2H), 7.77-7.69 (m, 2H), 7.68-7.60 (m, 2H), 7.01 (d, J=7.3 Hz, 1H), 6.95 (t, J=7.6 Hz, 1H), 6.57 (t, J=7.3 Hz, 1H), 6.49 (d, J=7.7 Hz, 1H), 3.97-3.75 (m, 2H), 3.27-3.02 (m, 2H), 2.36-2.13 (m, 2H). Enantiomeric excess >99.0%, RT 9.83 min. Analytical chiral chromatographic condition: Chiralpak IB, 4.6×250 mm, 5 micron. Mobile phase: 35% MeOH/65% CO$_2$. Flow: 2.0 mL/min, 150 Bar, 40° C.

Example 4

1'-(4-(1H-Pyrazol-4-yl)phenyl)-6-methoxyspiro[indoline-2,3'-pyrrolidin]-2'-one

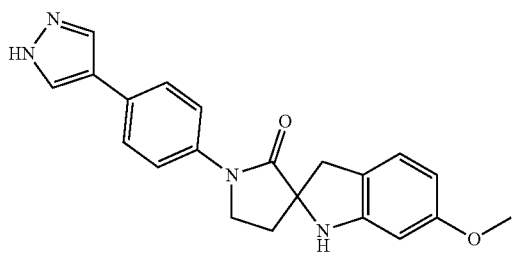 [SMILES: COc1ccc2c(c1)NC1(CCN(c3ccc(-c4cn[nH]c4)cc3)C1=O)C2]

Example 4A. 1-Tert-butyl 2-methyl 6-methoxyindoline-1,2-dicarboxylate

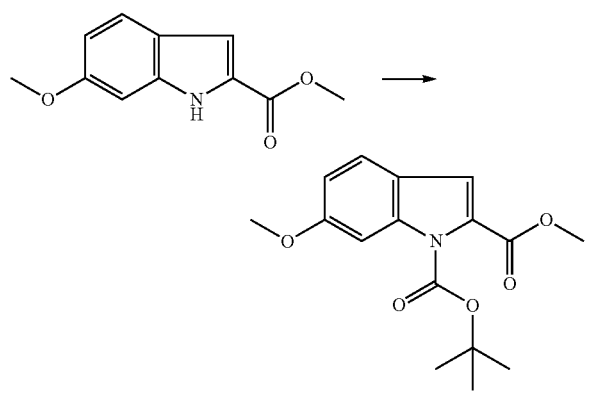

To a solution of methyl 6-methoxy-1H-indole-2-carboxylate (1 g, 4.87 mmol) in EtOAc (10 mL) at 0° C. was added Et$_3$N (1.019 mL, 7.31 mmol), DMAP (0.060 g, 0.487 mmol) and Boc-anhydride (1.36 mL, 5.85 mmol methyl 6-methoxy-1H-indole-2-carboxylate). The mixture was stirred at rt o.n. Water was added to the reaction mixture and extracted with AcOEt. The organic layer was washed with 1 M HCl, sat. NaHCO$_3$, brine, dried over MgSO$_4$ and evaporated to give 1-tert-butyl 2-methyl 6-methoxy-1H-indole-1,2-dicarboxylate as a yellow oil. MS(ESI) m/z: 250.1 (M+H-tBu)$^+$.

Example 4B. 1-Tert-butyl 2-methyl 6-methoxyindoline-1,2-dicarboxylate

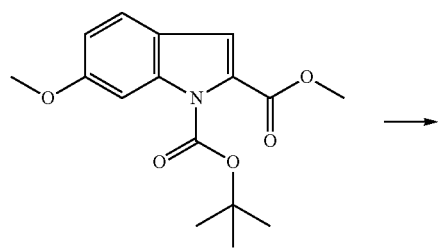

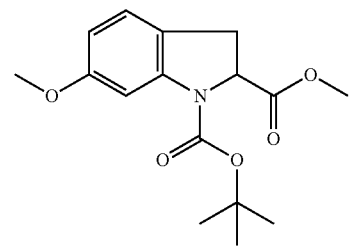

1-tert-butyl 2-methyl 6-methoxy-1H-indole-1,2-dicarboxylate was dissolved in EtOH (20 mL) and 10% Pd/C (0.2 g) was added under N$_2$. The mixture was stirred under a hydrogen atmosphere (balloon, 1 atm) for 6 hours at 50° C. The catalyst was filtered off and the filtrate was evaporated to give 1-tert-butyl 2-methyl 6-methoxyindoline-1,2-dicarboxylate (1.45 g, 97% yield) as a colorless oil. MS(ESI) m/z: 252.1 (M+H-tBu)+. $^1$H NMR (400 MHz, CDCl$_3$) δ 7.58 (br. s., 0.6H), 7.15 (br. s., 0.25H), 6.97 (d, J=8.1 Hz, 1H), 6.50 (dd, J=8.1, 2.2 Hz, 1H), 4.88 (br. s., 1H), 3.81 (s, 3H), 3.75 (s, 3H), 3.43 (dd, J=16.0, 11.6 Hz, 1H), 3.03 (dd, J=16.1, 4.4 Hz 1H), 1.69-1.43 (m, 9H).

Example 4C. 1-Tert-butyl 2-methyl 2-allyl-6-methoxyindoline-1,2-dicarboxylate

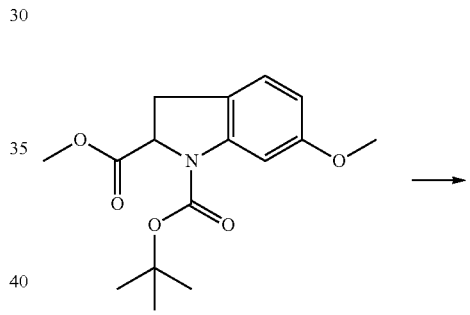

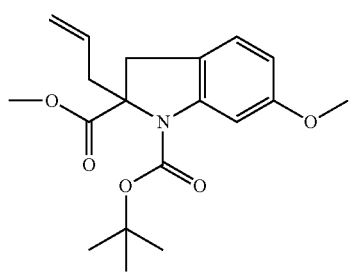

Was prepared using a procedure analogous to EXAMPLE 1C except that 1-tert-butyl 2-methyl indoline-1,2-dicarboxylate, EXAMPLE 1B was replaced by 1-tert-butyl 2-methyl 6-methoxyindoline-1,2-dicarboxylate and NaHMDS was replaced with LiHMDS to give 1-tert-butyl 2-methyl 2-allyl-6-methoxyindoline-1,2-dicarboxylate (1.06 g, 65% yield). $^1$H NMR (400 MHz, CDCl$_3$) δ 7.63-7.45 (m, 1H), 6.93 (d, J=8.1 Hz, 1H), 6.51 (dd, J=8.1, 2.2 Hz, 1H), 5.64 (ddt, J=17.1, 9.9, 7.4 Hz, 1H), 5.23-4.91 (m, 2H), 3.80 (s, 3H), 3.74 (s, 3H), 3.34-3.00 (m, 3H), 2.70 (dd, J=14.4, 7.6 Hz, 1H), 1.66-1.43 (m, 9H). MS(ESI) m % z: 248.1 (M+H-Boc)$^+$.

Example 4D. 1-Tert-butyl 2-methyl 6-methoxy-2-(2-oxoethyl)indoline-1,2-dicarboxylate

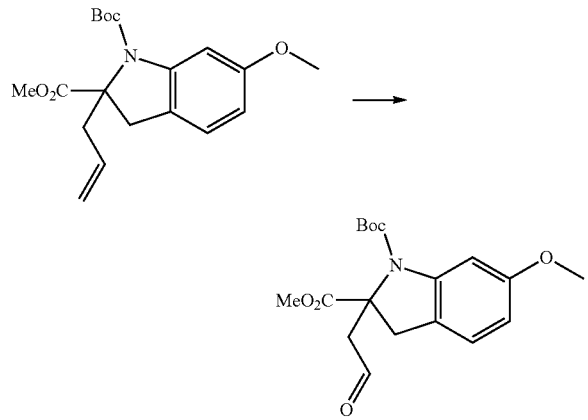

Prepared using a procedure analogous to EXAMPLE 1D except that 1-tert-butyl 2-methyl 2-allylindoline-1,2-dicarboxylate, EXAMPLE 1C was replaced by 1-tert-butyl 2-methyl 2-allyl-6-methoxyindoline-1,2-dicarboxylate to give 1-tert-butyl 2-methyl 6-methoxy-2-(2-oxoethyl)indoline-1,2-dicarboxylate (0.72 g, 68% yield) as a clear oil. MS(ESI) m/z: 250.1 (M+H-Boc)$^+$. $^1$H NMR (400 MHz, CDCl$_3$) δ 9.80 (br. s., 1H), 7.66-7.43 (m, 0.52H), 7.21-7.05 (m, 0.29H), 6.99 (d, J=8.1 Hz, 1H), 6.55 (dd, J=8.3, 2.3 Hz, 1H), 3.80 (s, 3H), 3.78 (s, 3H), 3.51-3.23 (m, 2H), 3.19 (dd. J=15.3, 3.2 Hz, 1H), 3.01 (br. s., 1H), 1.69-1.36 (m, 9H)

Example 4E. 1-Tert-butyl 2-methyl 2-(2-((4-bromophenyl)amino)ethyl)-6-methoxyindoline-1,2-dicarboxylate

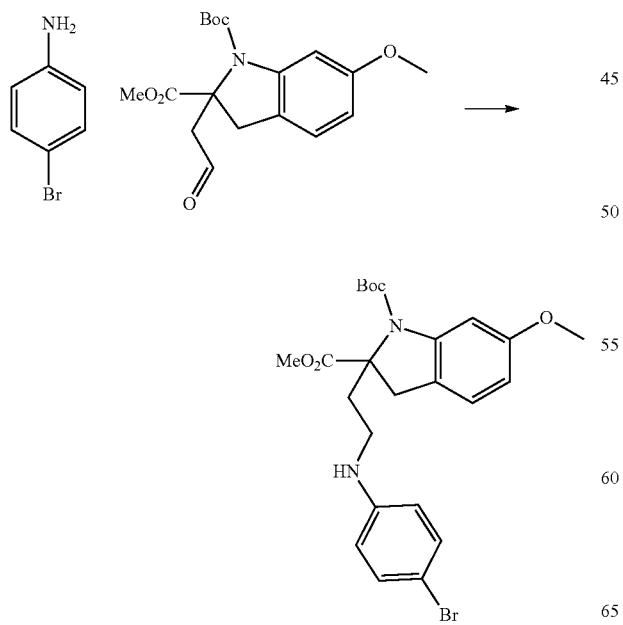

A mixture of 1-tert-butyl 2-methyl 6-methoxy-2-(2-oxoethyl)indoline-1,2-dicarboxylate (0.54 g, 1.546 mmol) and 4-bromoaniline (0.319 g, 1.855 mmol) in DCM (10 mL) was stirred at rt for 20 min. Sodium triacetoxyborohydride (0.557 g, 2.63 mmol) followed by acetic acid (0.088 mL, 1.546 mmol) were added. After 5 h at rt, the reaction was put in a freezer for 4 days, then rt for 6 hr. The reaction was quenched with 1 N NaOH, extracted with EtOAc (2×). The combined organic layers were concentrated, and purified by normal phase chromatography followed by reverse phase chromatography. The desired product fractions were combined and made slightly basic with sat NaHCO$_3$ and concentrated to remove most of methanol. The remaining aqueous layer was extracted with EtOAc (3×). The combined organic layers was washed with brine, dried over MgSO$_4$ and concentrated to give 1-tert-butyl 2-methyl 2-(2-((4-bromophenyl)amino)ethyl)-6-methoxyindoline-1,2-dicarboxylate (186 mg, 24% yield) as a brownish oil. MS(ESI) m/z: 505.3 (M+H)$^+$.

Example 4F. Tert-butyl 1'-(4-bromophenyl)-6-methoxy-2'-oxospiro[indoline-2,3'-pyrrolidine]-1-carboxylate

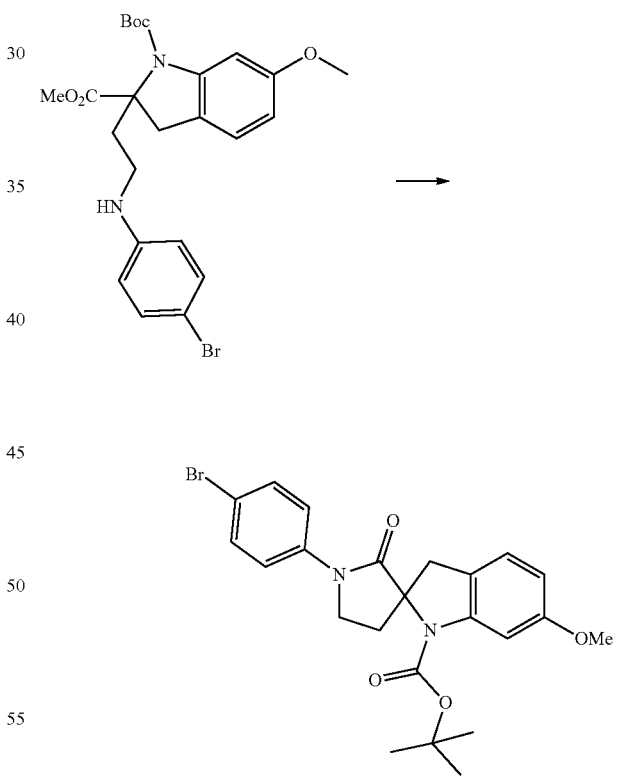

Prepared using a procedure analogous to EXAMPLE 1F except that 1-tert-butyl 2-methyl 2-(2-((4-bromophenyl)amino)ethyl)indoline-1,2-dicarboxylate. EXAMPLE 1E was replaced by 1-tert-butyl 2-methyl 2-(2-((4-bromophenyl)amino)ethyl)-6-methoxyindoline-1,2-dicarboxylate to give tert-butyl 1'-(4-bromophenyl)-6-methoxy-2'-oxospiro[indoline-2,3'-pyrrolidine]-1-carboxylate (134 mg, 77% yield). MS(ESI) m/z: 417.2 (M+H-tBu)$^+$.

Example 4

1'-(4-(1H-Pyrazol-4-yl)phenyl)-6-methoxyspiro[indoline-2,3'-pyrrolidin]-2'-one

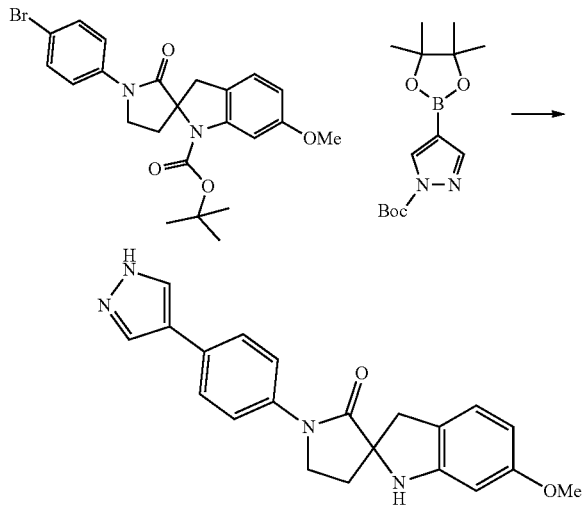

Prepared using a procedure analogous to EXAMPLE 1 except that tert-butyl 1'-(4-bromophenyl)-2'-oxospiro[indoline-2,3'-pyrrolidine]-1-carboxylate, EXAMPLE 1F was replaced by tert-butyl 1'-(4-bromophenyl)-6-methoxy-2'-oxospiro[indoline-2,3'-pyrrolidine]-1-carboxylate to give 1'-(4-(1H-pyrazol-4-yl)phenyl)-6-methoxyspiro[indoline-2,3'-pyrrolidin]-2'-one TFA (7 mg, 11% yield) as a white solid. MS(ESI) m/z: 361.0 (M+H)$^+$. $^1$H NMR (400 MHz, DMSO-d$_6$) δ 8.04 (br. s., 2H), 7.75-7.59 (m, 4H), 6.86 (d, J=7.9 Hz, 1H), 6.11 (dd, J=8.0, 2.3 Hz, 1H), 6.07 (d, J=2.4 Hz, 1H), 3.89-3.72 (m, 2H), 3.66 (s, 3H), 3.03-2.95 (m, 1H), 2.32-2.13 (m, 2H). HPLC: Method A, RT=6.20 min, 99.1% purity; Method B, RT=7.84 min, 98.4% purity.

Example 5

1'-(4-(1H-Pyrazol-4-yl)phenyl)-6-methoxyspiro[indoline-2,3'-pyrrolidin]-2'-one (Enantiomer 1)

and

Example 6

1'-(4-(1H-Pyrazol-4-yl)phenyl)-6-methoxyspiro[indoline-2,3'-pyrrolidin]-2'-one (Enantiomer 2)

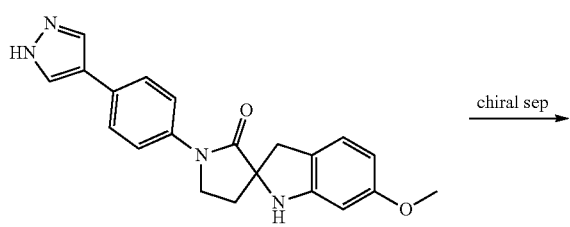

chiral sep

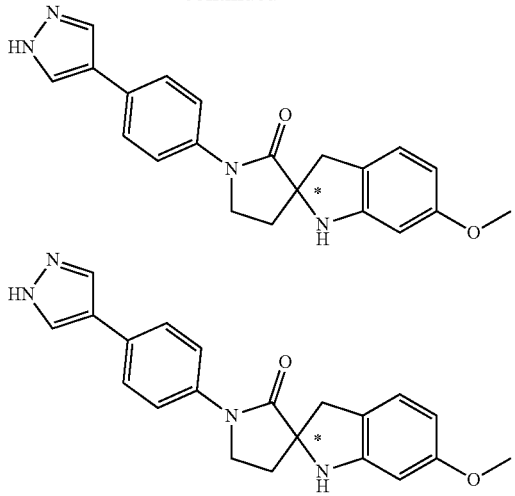

Prepared by chiral separation of racemic 1'-(4-(1H-pyrazol-4-yl)phenyl)-6-methoxyspiro[indoline-2,3'-pyrrolidin]-2'-one, EXAMPLE 4 using Chiralpak IB, 21×250 mm, 5 micron; eluting with 35% MeOH/65% CO$_2$. Flow 45 mL/min, 150 Bar, 40° C. to give 2 enantiomers.

EXAMPLE 5. 1'-(4-(1H-Pyrazol-4-yl)phenyl)-6-methoxyspiro[indoline-2,3'-pyrrolidin]-2'-one (enantiomer 1), 1$^{st}$ peak (10 mg) as a bluish solid. MS(ESI) m/z: 361.3 (M+H)$^+$. $^1$H NMR (400 MHz. DMSO-d$_6$) δ 8.05 (br. s., 2H), 7.78-7.69 (m, 2H), 7.67-7.59 (m, 2H), 6.87 (d, J=7.9 Hz, 1H), 6.33 (s, 1H), 6.12 (dd, J=8.0, 2.3 Hz, 1H), 6.07 (d, J=2.2 Hz, 1H), 3.91-3.75 (m, 2H), 3.67 (s, 3H), 3.20-2.94 (m, 2H), 2.32-2.14 (m, 2H). HPLC: Method A, RT 6.39 min, 96% purity; Method B. RT 8.15 min. 96% purity. Enantiomeric excess >99.0%, RT 11.05 min. Analytical chiral chromatographic condition: Chiralpak IB, 4.6×250 mm, 5 micron. Mobile phase: 35% MeOH/65% CO$_2$. Flow: 2.0 mL/min, 150 Bar, 40° C.

EXAMPLE 6. 1'-(4-(1H-Pyrazol-4-yl)phenyl)-6-methoxyspiro[indoline-2,3'-pyrrolidin]-2'-one (enantiomer 2). 2$^{nd}$ peak (19.6 mg) as a bluish solid. MS(ESI) m/z: 361.3 (M+H)$^+$. HPLC: Method A. RT 6.37 min, 97% purity; Method B, RT 8.12 min, 96% purity. Enantiomeric excess >93.8%, RT 15.03 min. Analytical chiral chromatographic condition: Chiralpak IB, 4.6×250 mm, 5 micron. Mobile phase: 35% MeOH/65% CO$_2$. Flow: 2.0 mL/min, 150 Bar, 40° C.

Example 7

1'-(4-(1H-Pyrazol-4-yl)phenyl)-5-fluorospiro[indoline-2,3'-pyrrolidin]-2'-one, TFA, racemic

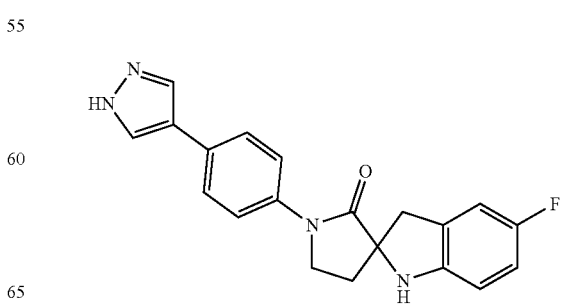

Prepared using a procedure analogous to EXAMPLE 4 except that methyl 6-methoxy-1H-indole-2-carboxylate, EXAMPLE 4A, was replaced by ethyl 5-fluoro-1H-indole-2-carboxylate to give 1'-(4-(1H-pyrazol-4-yl)phenyl)-5-fluorospiro[indoline-2,3'-pyrrolidin]-2'-one, TFA (17 mg, 25% yield). HPLC: Method A, RT=6.37 min, 99.3%6 purity; Method B RT=8.04 min, 98.7% purity. MS(ESI) m/z: 349.0 (M+H)$^+$. $^1$H NMR (400 MHz, DMSO-$d_6$) δ 12.92 (br. s., 1H), 8.18 (s, 1H), 7.92 (s, 1H), 7.76-7.68 (m, 2H), 7.69-7.59 (m, 2H), 6.89 (dd, J=8.7, 2.5 Hz, 1H), 6.81-6.69 (m, 1H), 6.43 (dd, J=8.6, 4.4 Hz, 1H), 6.23 (s, 1H), 3.98-3.70 (m, 2H), 3.29-3.01 (m, 2H), 2.35-2.13 (m, 2H)

Example 8

1'-(4-(1H-Pyrazol-4-yl)phenyl)-5-fluorospiro[indoline-2,3'-pyrrolidin]-2'-one, Enantiomer 1, and Example 9

1'-(4-(H-Pyrazol-4-yl)phenyl)-5-fluorospiro[indoline-2,3'-pyrrolidin]-2'-one, Enantiomer 2

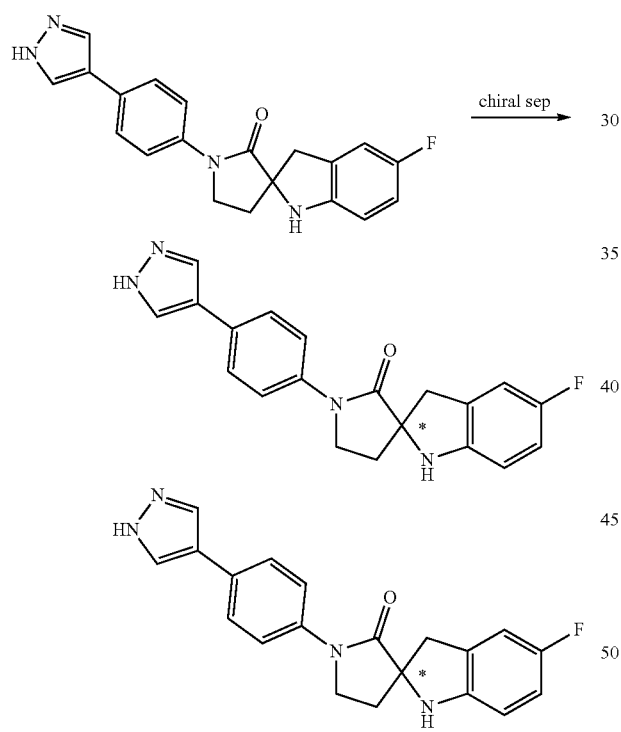

Chiral separation of 1'-(4-1H-pyrazol-4-yl)phenyl)-5-fluorospiro[indoline-2,3'-pyrrolidin]-2'-one, EXAMPLE 7 using Chiralpak IB, 21×250 mm, 5 micron; eluting with 35% MeOH/65% CO$_2$. Flow 45 mL/min, 150 Bar, 40° C. gave the individual enantiomers.

EXAMPLE 8, 1'-(4-(1H-Pyrazol-4-yl)phenyl)-5-fluorospiro[indoline-2,3'-pyrrolidin]-2'-one, TFA (enantiomer 1). Off-white solid. MS(ESI) m/z: 349.3 [M+H]$^+$. $^1$H NMR (500 MHz, DMSO-$d_6$) δ 12.91 (br. s., 1H), 8.15 (br. s., 1H), 7.94 (br. s., 1H), 7.76-7.67 (m, 2H), 7.67-7.60 (m, 2H), 6.94-6.84 (m, 1H), 6.80-6.69 (m, 1H), 6.53 (s, 2H), 6.43 (dd, J=8.4, 4.5 Hz, 1H), 6.23 (br. s., 1H), 3.94-3.72 (m, 2H), 3.25 (d, J=16.5 Hz, 1H), 3.09 (d J=16.5 Hz, 1H), 2.34-2.14 (m, 2H), $^{19}$F NMR (471 MHz, DMSO-$d_6$) δ −78.50 (s, 3F), −133.23 (s, 1F). HPLC: Method A. RT 6.24 min, 97.9% purity; Method B, RT 8.02 min, 98.0% purity. Enantiomeric excess 97.8%, RT 6.19 min. Analytical chiral chromatographic condition: Chiralpak IB, 4.6×250 mm, 5 micron. Mobile phase: 35% MeOH/65% CO$_2$. Flow: 2.0 mL/min, 150 Bar, 40° C.

EXAMPLE 9. 1'-(4-(1H-Pyrazol-4-yl)phenyl)-5-fluorospiro[indoline-2,3'-pyrrolidin]-2'-one, TFA (enantiomer 2). Off-white solid. MS(ESI) m/z: 349.0 [M+H]$^+$. $^1$H NMR (500 MHz, DMSO-$d_6$) δ 8.04 (br. s., 2H), 7.74-7.67 (m, 2H), 7.67-7.60 (m, 2H), 6.87 (dd, J=8.5, 2.5 Hz, 1H), 6.79-6.70 (m, 1H), 6.42 (dd, J=8.4, 4.5 Hz, 1H), 3.88-3.75 (m, 2H), 3.24 (d, J=16.5 Hz, 1H), 3.08 (d, J=16.8 Hz, 1H), 2.32-2.23 (m, 1H), 2.24-2.15 (m, 1H), $^{19}$F NMR (471 MHz, DMSO-$d_6$) δ −73.85 (br. s., 3F), −128.18 (s, 1F). HPLC: Method A, RT 6.19 min, 92% purity; Method B, RT 7.98 min, 94% purity. Enantiomeric excess 93.6%, RT 8.50 min. Analytical chiral chromatographic conditions: Chiralpak IB, 4.6×250 mm, 5 micron. Mobile phase: 35% MeOH/65% CO$_2$. Flow: 2.0 mL/min, 150 Bar, 40° C.

Example 10

1'-(6-Methoxy-5-(H-pyrazol-4-yl)pyridin-2-yl)spiro[indoline-2,3'-pyrrolidin]-2'-one

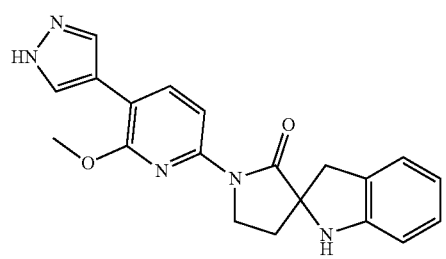 [SMILES: COc1nc(N2CCC3(Cc4ccccc4N3)C2=O)ccc1-c1cn[nH]c1]

Example 10A. 5-Bromo-6-methoxypyridin-2-amine

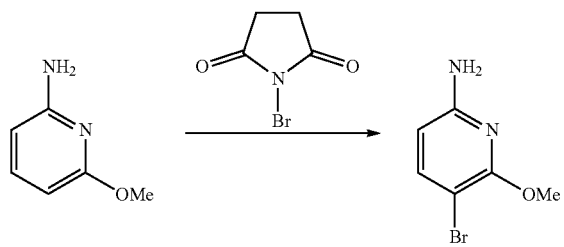 [SMILES: COc1cccc(N)n1 ; O=C1CCC(=O)N1Br ; COc1nc(N)ccc1Br]

To a solution of 6-methoxypyridin-2-amine (0.873 g, 7.03 mmol) in acetonitrile (40 mL) was added N-bromosuccinimide (0.626 g, 3.52 mmol) and the reaction mixture was stirred at rt for 1.25 h. Additional N-bromosuccinimide (0.626 g, 3.52 mmol) added and the reaction mixture was stirred at rt for another 30 min. The reaction mixture was diluted with water and extracted with EtOAc (2×). The combined organic extracts were washed with brine, concentrated and purified by normal phase chromatography to give 5-bromo-6-methoxypyridin-2-amine (354 mg, 25% yield) as an orange oil which solidified upon standing. MS(ESI) m/z:

202.9 (M+H)⁺. ¹H NMR (400 MHz, CDCl₃) δ 7.48 (d, J=8.1 Hz, 1H), 5.98 (d, J=8.1 Hz, 1H), 4.31 (br. s., 2H), 3.91 (s, 3H).

Example 10

1'-(4-(1H-Pyrazol-4-yl)phenyl)-5-fluorospiro[indoline-2,3'-pyrrolidin]-2'-one, TFA

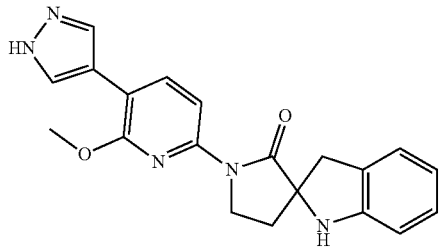 [SMILES: COc1nc(N2CCC3(Cc4ccccc4N3)C2=O)ccc1-c1cn[nH]c1]

Prepared using a procedure analogous to EXAMPLE 1 except that in EXAMPLE 1E, 4-bromoaniline and NaBH₃CN in MeOH were replaced by 5-bromo-6-methoxypyridin-2-amine, EXAMPLE 10A and NaBH(OAc)₃, acetic acid in THF to give 1'-(6-methoxy-5-(1H-pyrazol-4-yl)pyridin-2-yl)spiro[indoline-2,3'-pyrrolidin]-2'-one, TFA (21 mg, 42% yield).

HPLC: Method A. RT=10.91 min, 98.6% purity; Method B, RT=13.86 min, 100% purity. MS(ESI) m/z: 362.3 (M+H)³. ¹H NMR (400 MHz, DMSO-d₆) δ 8.16-8.03 (m, 1H), 7.93 (d, J=8.4 Hz, 1H), 7.01 (d, J=7.3 Hz, 1H), 6.96 (t, J=7.7 Hz, 1H), 6.57 (td, J=7.4, 0.9 Hz, 1H), 6.49 (d, J=7.7 Hz, 1H), 4.18-4.09 (m, 1H), 4.02 (s, 3H), 4.00-3.92 (m, 1H), 3.30-3.06 (m, 2H), 2.32-2.15 (m, 2H)

Example 11

1'-(4-(1H-Pyrazol-4-yl)phenyl)-1,3-dihydrospiro[indene-2,3'-pyrrolidin]-2'-one, TFA

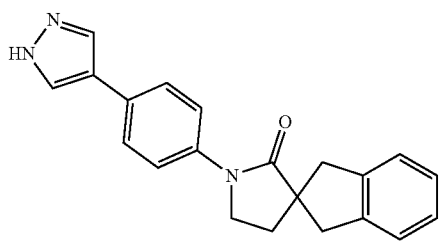 [SMILES: O=C1N(c2ccc(-c3cn[nH]c3)cc2)CCC12Cc1ccccc1C2]

Example 11A. 1'-(4-Bromophenyl)-1,3-dihydrospiro[indene-2,3'-pyrrolidin]-2'-one

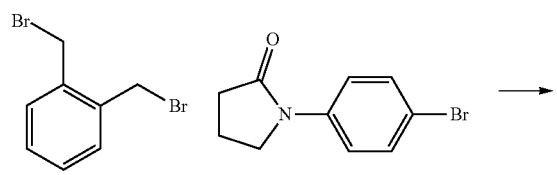

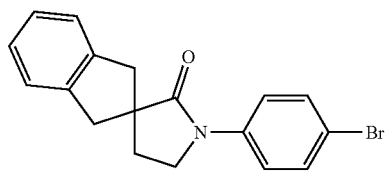

To a solution of 1-(4-bromophenyl)pyrrolidin-2-one (200 mg, 0.833 mmol) in THF (5 mL) was added LiHMDS (2.499 mL, 2.499 mmol) dropwise at −78° C. The reaction was stirred at −30° C. for 30 min then recooled to −78° C. 1,2-bis(bromomethyl)benzene (264 mg, 1.000 mmol) in THF (5 mL) was added dropwise and the reaction was stirred at rt o.n. The mixture was quenched with sat NH₄Cl, extracted EtOAc (2×). The combined organic layers were concentrated then purified by normal phase chromatography to give 1'-(4-bromophenyl)-1,3-dihydrospiro[indene-2,3'-pyrrolidin]-2'-one (57 mg, 20% yield) as a brownish oil. MS(ESI) m/z: 341.95/343.95 (M+H)⁺.

Example 11

1'-(4-Bromophenyl)-1,3-dihydrospiro[indene-2,3'-pyrrolidin]-2'-one, TFA

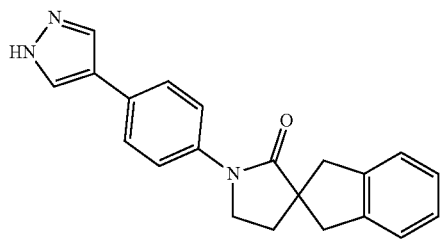 [SMILES: O=C1N(c2ccc(-c3cn[nH]c3)cc2)CCC12Cc1ccccc1C2]

Prepared using a procedure analogous to EXAMPLE 1 except that tert-butyl 1'-(4-bromophenyl)-2'-oxospiro[indoline-2,3'-pyrrolidine]-1-carboxylate, EXAMPLE 1F was replaced by 1'-(4-bromophenyl)-1,3-dihydrospiro[indene-2,3'-pyrrolidin]-2'-one to give 1'-(4-(1H-pyrazol-4-yl)phenyl)-1,3-dihydrospiro[indene-2,3'-pyrrolidin]-2'-one, TFA (4 mg, 5% yield). MS(ESI) m/z: 330.3 (M+H)⁺. HPLC: Method A, RT=11.33 min, 96.5% purity; Method B, RT=14.29 min, 97.9% purity. ¹H NMR (400 MHz, DMSO-d₆) δ 8.18 (s, 1H), 7.92 (s, 1H), 7.77-7.69 (m, 2H), 7.67-7.59 (m, 2H), 7.29-7.21 (m, 2H), 7.20-7.13 (m, 2H), 3.89 (t, J=6.7 Hz, 2H), 3.30-3.21 (m, 3H), 3.00 (d, J=15.8 Hz, 2H), 2.13 (t, J=6.7 Hz, 2H)

Example 12

1'-(4-(1H-Pyrazol-4-yl)phenyl)-5-methoxyspiro[indoline-2,3'-pyrrolidin]-2'-one

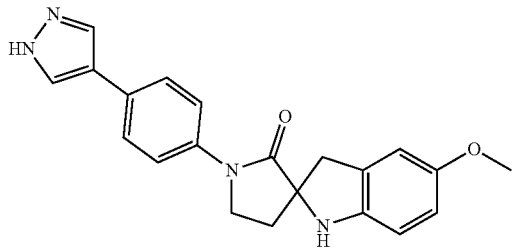 [SMILES: COc1ccc2c(c1)CC1(CCN(c3ccc(-c4cn[nH]c4)cc3)C1=O)N2]

Prepared using a procedure analogous to EXAMPLE 4 except that methyl 6-methoxy-1H-indole-2-carboxylate was replaced by ethyl 5-methoxy-1H-indole-2-carboxylate and NaBH$_3$CN in MeOH was used in the reductive amination to give 1'-(4-(1H-pyrazol-4-yl)phenyl)-5-methoxyspiro[indoline-2,3'-pyrrolidin]-2'-one (45 mg, 50% yield) as a greyish solid. MS(ESI) m/z: 361.05 (M+H)$^+$. $^1$H NMR (400 MHz. DMSO-d$_6$) δ 8.05 (br. s., 2H), 7.77-7.67 (m, 2H), 7.66-7.60 (m, 2H), 6.70 (d, J=2.4 Hz, 1H), 6.56 (dd, J=8.5, 2.5 Hz, 1H), 6.42 (d, J=8.4 Hz, 1H), 5.91 (br. s., 1H), 3.93-3.75 (m, 2H), 3.66 (s, 3H), 3.35 (br. s., 1H), 3.26-3.00 (m, 2H), 2.32-2.12 (m, 2H). HPLC: Method A, RT=5.13 min, 97.1% purity; Method B, RT=6.98 min, 96.8% purity.

Example 13

1'-(4-(1H-Indazol-5-yl)phenyl)spiro[indoline-2,3'-pyrrolidin]-2'-one

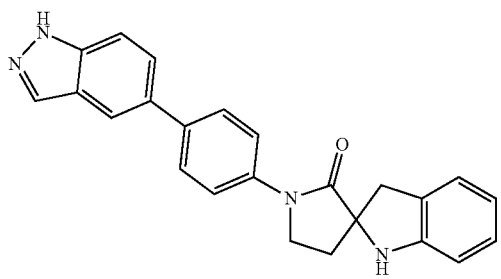 [SMILES: O=C1N(c2ccc(-c3ccc4[nH]ncc4c3)cc2)CCC12Cc1ccccc1N2]

Prepared using a procedure analogous to EXAMPLE 1 except that tert-butyl 4-(4,4,5,5-tetramethyl-1,3,2-dioxaborolan-2-yl)-1H-pyrazole-1-carboxylate was replaced by tert-butyl 5-(4,4,5,5-tetramethyl-1,3,2-dioxaborolan-2-yl)-1H-indazole-1-carboxylate to give 1'-(4-(1H-indazol-5-yl)phenyl)spiro[indoline-2,3'-pyrrolidin]-2'-one (1.2 mg, 7% yield). MS(ESI) m/z: 381.1 (M+H)$^+$. HPLC: METHOD C, RT 1.61 min. $^1$H NMR (500 MHz, DMSO-d$_6$) δ8.15-8.10 (m, 1H), 8.06-8.01 (m, 1H), 7.86-7.81 (m, 2H), 7.78-7.73 (m, 2H), 7.71-7.66 (m, 1H), 7.64-7.59 (m, 1H), 7.03-6.99 (m, 1H), 6.98-6.91 (m, 1H), 6.60-6.53 (m, 1H), 6.51-6.46 (m, 1H), 6.38-6.32 (m, 1H), 3.94-3.79 (m, 2H), 3.28-3.06 (m, 2H), 2.34-2.14 (m, 2H).

Example 14

1'-(4-(1H-Pyrazol-4-yl)phenyl)-6-methoxy-1-methylspiro[indoline-2,3'-pyrrolidin]-2'-one

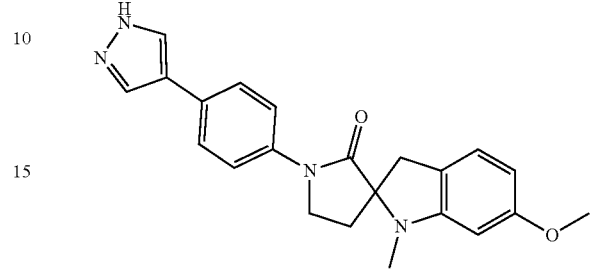

Example 14A. 1'-(4-Bromophenyl)-6-methoxy-1-methylspiro[indoline-2,3'-pyrrolidin]-2'-one

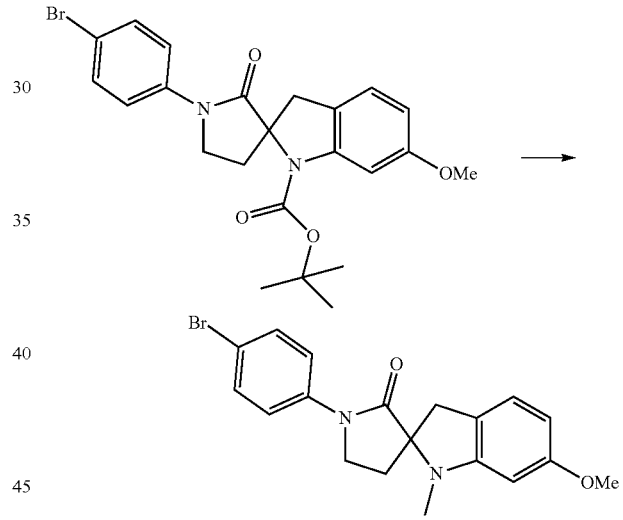

To a solution of tert-butyl 1'-(4-bromophenyl)-6-methoxy-2'-oxospiro[indoline-2,3'-pyrrolidine]-1-carboxylate, EXAMPLE 4F (57 mg, 0.120 mmol) in DCM (0.5 mL) was added TFA (9.28 µl, 0.120 mmol). The reaction was stirred at rt 0.5 h then concentrated. To the residue was added EtOAc, and sat. NaHCO$_3$. Extracted with EtOAc (2×). The combined organic layers were concentrated to dryness. To the residue was added acetonitrile (2 mL), K$_2$CO$_3$ (49.9 mg, 0.361 mmol) followed by iodomethane (0.011 mL, 0.181 mmol). After 4 h, additional iodomethane (0.03 mL) was added and the vial was capped and heated at 65° C. o.n. Water was added and the reaction was extracted with EtOAc (2×). The combined organic layers were concentrated then purified by normal phase chromatography to give 1'-(4-bromophenyl)-6-methoxy-1-methylspiro[indoline-2,3'-pyrrolidin]-2'-one (45 mg, 75% yield). MS(ESI) m/z: 389.0 (M+H)$^+$.

Example 14

1'-(4-(1H-Pyrazol-4-yl)phenyl)-6-methoxy-1-methylspiro[indoline-2,3'-pyrrolidin]-2'-one

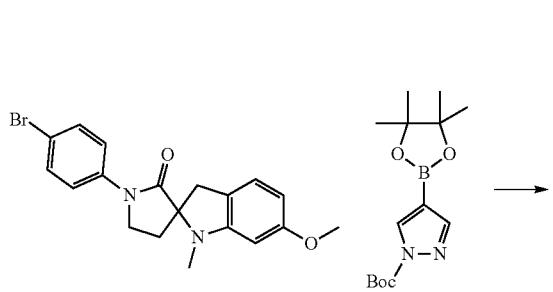

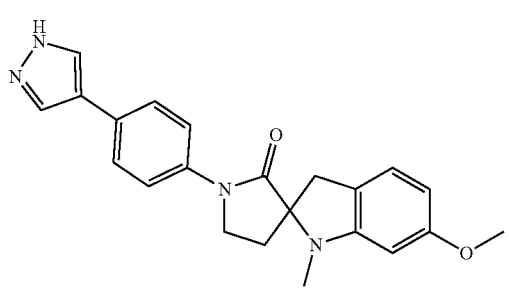 [SMILES: COc1ccc2c(c1)N(C)C1(CCN(c3ccc(-c4cn[nH]c4)cc3)C1=O)C2]

Prepared using a procedure analogous to EXAMPLE 1 except that tert-butyl 1'-(4-bromophenyl)-2'-oxospiro[indoline-2,3'-pyrrolidine]-1-carboxylate, EXAMPLE 1F was replaced by 1'-(4-bromophenyl)-6-methoxy-1-methylspiro[indoline-2,3'-pyrrolidin]-2'-one to give 1'-(4-(1H-pyrazol-4-yl)phenyl)-6-methoxy-1-methylspiro[indoline-2,3'-pyrrolidin]-2'-one (8.2 mg, 33% yield). MS(ESI) m/z: 375.3 (M+H)$^+$. HPLC: Method C, RT=1.54 min. $^1$H NMR (500 MHz, DMSO-d$_6$) δ 8.03 (br. s., 2H), 7.74-7.56 (m, 4H), 6.85 (d, J=7.7 Hz, 1H), 6.10 (d, J=7.7 Hz, 1H), 6.02 (s, 1H), 3.88-3.76 (m, 2H), 3.69 (s, 1H), 3.56 (d, J=10.5 Hz, 1H), 3.07 (q, J=15.6 Hz, 2H), 2.69 (s, 3H), 2.51 (br. s., 9H), 2.45-2.34 (m, 1H), 2.12 (d, J=12.8 Hz, 1H)

Example 15

1'-(4-(1H-Pyrazol-4-yl)phenyl)-5-fluoro-1,3-dihydrospiro[indene-2,3'-pyrrolidin]-2'-one, Enantiomer 1

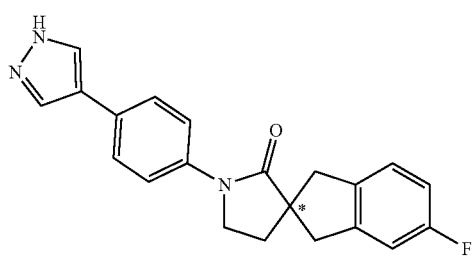 [SMILES: O=C1N(c2ccc(-c3cn[nH]c3)cc2)CCC12Cc1ccc(F)cc1C2]

Example 15A. Methyl 6-fluoro-1-oxo-2,3-dihydro-1H-indene-2-carboxylate

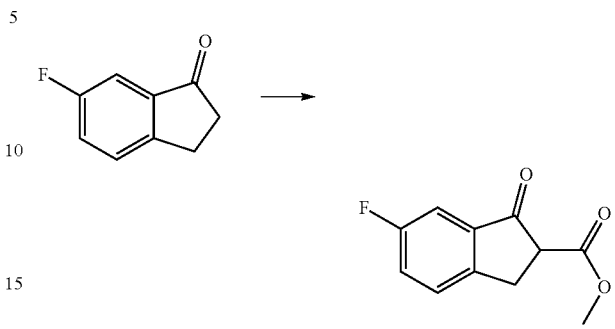

To a suspension of anhyd. THF (10 mL) and sodium hydride 60% in oil (0.84 g, 21.0 mmol) was added dimethyl carbonate (1.179 mL, 14.0 mmol) in portions at rt. The reaction was heated to 70° C. for 0.5 h, then cooled to 0° C., and a solution of 6-fluoro-2,3-dihydro-1H-inden-1-one (1.05 g, 7 mmol) in THF (10 mL) was added dropwise. The resulting mixture was heated at 70° C. Toluene (10 mL) was added to aid stirring. After heating at 70° C. o.n., the reaction was cooled in ice bath, and quenched with water and IN HCl (acidic). Extract with EtOAc (3×). The combined organic layers were washed with brine, concentrated then purified by normal phase chromatography to give methyl 6-fluoro-1-oxo-2,3-dihydro-1H-indene-2-carboxylate (1.16 g, 80% yield) as an orange oil which solidified upon standing. MS(ESI) m/z: 209.1 (M+H)$^+$. $^1$H NMR (400 MHz. CDCl$_3$) 7.78 (dd, J=8.6, 5.3 Hz, 1H), 7.17 (dt, J=8.6, 0.9 Hz, 1H), 7.10 (td, J=8.6, 2.2 Hz, 1H), 3.80 (s, 3H), 3.77 (dd, J=8.1, 4.0 Hz, 1H), 3.61-3.53 (m, 1H), 3.42-3.31 (m, 1H).

Example 15B. Methyl 5-fluoro-2,3-dihydro-1H-indene-2-carboxylate

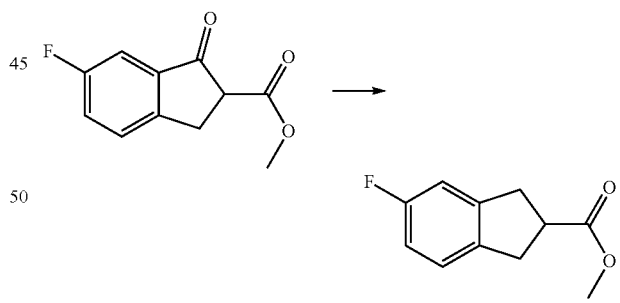

To a brown solution of methyl 6-fluoro-1-oxo-2,3-dihydro-1H-indene-2-carboxylate (0.6 g, 2.88 mmol) in TFA (8 mL) at 0° C. under N$_2$ was added triethylsilane (1.381 mL, 8.65 mmol) dropwise. The reaction was stirred at 0° C. for 0.5 hr then rt on. The reaction was concentrated then poured into sat NaHCO$_3$ and extracted with EtOAc (2×). The combined organic layers were concentrated then purified by normal phase chromatography to give methyl 5-fluoro-2,3-dihydro-1H-indene-2-carboxylate (453 mg, 81% yield) as an orange oil. $^1$H NMR (400 MHz, CDCl$_3$) δ 7.12 (dd, J=7.9, 5.3 Hz, 1H), 6.92-6.79 (m, 2H), 3.73 (s, 3H), 3.44-3.31 (m, 1H), 3.30-3.11 (m, 4H)

Example 15C. Methyl 2-allyl-5-fluoro-2,3-dihydro-1H-indene-2-carboxylate

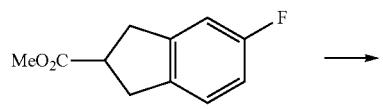

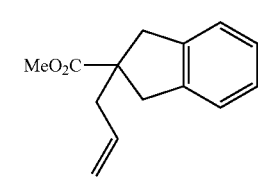

Prepared using a procedure analogous to EXAMPLE 1C except that 1-tert-butyl 2-methyl indoline-1,2-dicarboxylate, EXAMPLE 1B was replaced with methyl 5-fluoro-2,3-dihydro-1H-indene-2-carboxylate to give methyl 2-allyl-5-fluoro-2,3-dihydro-1H-indene-2-carboxylate (465 mg, 85% yield) yellow oil. MS(ESI) m/z: 235.1 (M+H)$^+$. $^1$H NMR (400 MHz, CDCl$_3$) δ 7.09 (dd, J=8.0, 5.2 Hz, 1H), 6.91-6.76 (m, 2H), 5.76-5.61 (m, 1H), 5.12-4.98 (m, 2H), 3.70 (s, 3H), 3.40 (dd, J=18.3, 17.2 Hz, 2H), 2.91 (dd, J=16.3, 11.0 Hz, 2H), 2.46 (dq, J=7.3, 1.2 Hz, 2H)

Example 15D. Methyl 5-fluoro-2-(2-oxoethyl)-2,3-dihydro-1H-indene-2-carboxylate

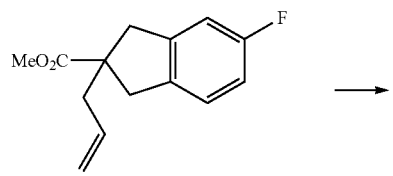

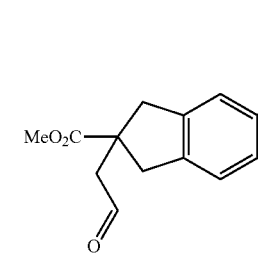

Prepared using a procedure analogous to EXAMPLE 1D except that 1-tert-butyl 2-methyl 2-allylindoline-1,2-dicarboxylate, EXAMPLE 1C was replaced with methyl 2-allyl-5-fluoro-2,3-dihydro-1H-indene-2-carboxylate to give methyl 5-fluoro-2-(2-oxoethyl)-2,3-dihydro-1H-indene-2-carboxylate (330 mg, 70% yield) as brown oil. MS(ESI) m/z: 237.1 (M+H)$^+$.

$^1$H NMR (400 MHz, CDCl$_3$) δ 9.73 (t, J=1.1 Hz, 1H), 7.11 (dd, J=7.7, 5.3 Hz, 1H), 6.92-6.80 (m, 2H), 3.75-3.70 (m, 3H), 3.62-3.44 (m, 2H), 2.99-2.86 (m, 4H)

Example 15E. 1'-(4-Bromophenyl)-5-fluoro-1,3-dihydrospiro[indene-2,3'-pyrrolidin]-2'-one

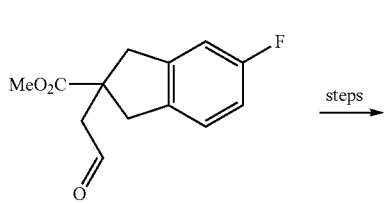

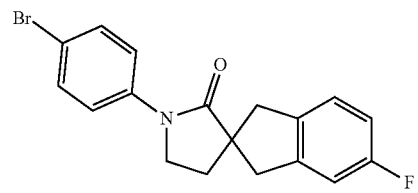

enantiomer 1

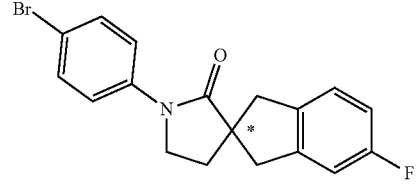

enantiomer 2

Prepared using a procedure analogous to EXAMPLE 1D through EXAMPLE 1F except that 1-tert-butyl 2-methyl 2-(2-oxoethyl)indoline-1,2-dicarboxylate, EXAMPLE 1D was replaced by methyl 5-fluoro-2-(2-oxoethyl)-2,3-dihydro-1H-indene-2-carboxylate to give 1'-(4-bromophenyl)-5-fluoro-1,3-dihydrospiro[indene-2,3'-pyrrolidin]-2'-one (103 mg, 71% yield) as a white solid. MS(ESI) m/z: 360.2/362 (M+H)$^+$. $^1$H NMR (400 MHz, CDCl$_3$) δ 7.65-7.55 (m, 1H), 7.53-7.46 (m, 1H), 7.14 (dd, J=8.1, 5.1 Hz, 1H), 6.90 (t, J=9.2 Hz, 2H), 3.82 (t, J=6.7 Hz, 2H), 3.55-3.35 (m, 2H), 2.89 (dd, J=15.7, 6.3 Hz, 2H), 2.18 (t, J=6.7 Hz, 2H).

The enantiomers were separated. 103 mg racemic mixture gave enantiomer 1 (44.5 mg, 43% yield) as a white solid, RT 12.07, >99.0% enantiomeric excess. Enantiomer 2 (44.5 mg, 43% yield) as a white solid, RT 17.83, 90.2% enantiomeric excess.

Analytical chiral chromatographic conditions: Chiralpak AS-H, 4.6×250 mm, 5 micron. Mobile phase: 25% MeOH/75% CO$_2$. Flow: 2.0 mL/min, 150 Bar, 40° C. Preparative chiral chromatographic condition: Chiralpak AS-H, 21×250 mm, 5 micron. Mobile phase: 25% MeOH/75% CO$_2$. Flow: 45 mL/min, 100 Bar, 40° C.

Example 15

1'-(4-(1H-Pyrazol-4-yl)phenyl)-5-fluoro-1,3-dihydrospiro[indene-2,3'-pyrrolidin]-2'-one, Enantiomer 1

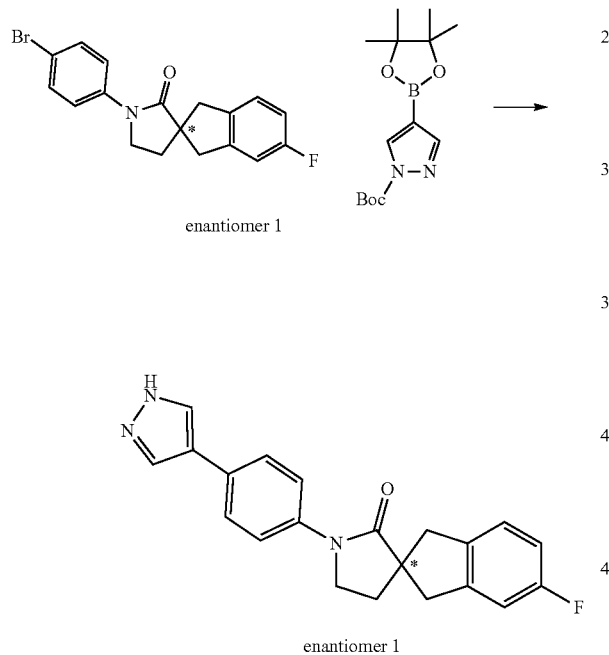

Prepared using a procedure analogous to EXAMPLE 1 except that tert-butyl 1'-(4-bromophenyl)-2'-oxospiro[indoline-2,3'-pyrrolidine]-1-carboxylate, 1F was replaced by 1'-(4-bromophenyl)-5-fluoro-1,3-dihydrospiro[indene-2,3'-pyrrolidin]-2'-one (EXAMPLE 15E, enantiomer 1) to give 1'-(4-(1H-pyrazol-4-yl)phenyl)-5-fluoro-1,3-dihydrospiro[indene-2,3'-pyrrolidin]-2'-one (2.2 mg, 11% yield). MS(ESI) m/z: 348.1 (M+H)$^+$. HPLC: Method C, RT 1.76 min. $^1$H NMR (500 MHz, DMSO-d$_6$) δ 8.14 (br. s., 1H), 7.94 (br. s., 1H), 7.73-7.57 (m, 4H), 7.27-7.19 (m, 1H), 7.07 (d, J=8.9 Hz, 1H), 6.97 (t, J=8.2 Hz, 1H), 3.86 (t, J=6.6 Hz, 2H), 3.30-3.12 (m, 2H), 3.04-2.89 (m, 2H), 2.12 (t, J=6.6 Hz, 2H)

Example 16

1'-(4-(1H-Pyrazol-4-yl)phenyl)-5-fluoro-1,3-dihydrospiro[indene-2,3'-pyrrolidin]-2'-one, Enantiomer 2

Prepared using a procedure analogous to EXAMPLE 1 except that tert-butyl 1'-(4-bromophenyl)-2'-oxospiro[indoline-2,3'-pyrrolidine]-1-carboxylate, 1F was replaced by 1'-(4-bromophenyl)-5-fluoro-1,3-dihydrospiro[indene-2,3'-pyrrolidin]-2'-one (EXAMPLE 15E, enantiomer 2) to give 1'-(4-(1H-pyrazol-4-yl)phenyl)-5-fluoro-1,3-dihydrospiro[indene-2,3'-pyrrolidin]-2'-one (4.2 mg, 42% yield). MS(ESI) m/z: 348.2 (M+H)$^+$. HPLC: Method C, RT 1.68 min. $^1$H NMR (500 MHz, DMSO-d$_6$) δ 8.16 (br. s., 1H), 7.92 (br. s., 1H), 7.73-7.66 (m, 2H), 7.66-7.58 (m, 2H), 7.29-7.19 (m, 1H), 7.07 (d, J=8.8 Hz, 1H), 6.98 (t, J=8.7 Hz, 1H), 3.90-3.81 (m, 2H), 3.30-3.14 (m, 2H), 2.97 (t, J=15.6 Hz, 2H), 2.12 (t, J=6.5 Hz, 2H)

Example 17

5-Fluoro-1'-(6-methoxy-5-(1H-pyrazol-4-yl)pyridin-2-yl)-1,3-dihydrospiro[indene-2,3'-pyrrolidin]-2'-one, Enantiomer 1

Example 17A. 5-Fluoro-1'-(6-methoxy-5-(1H-pyrazol-4-yl)pyridin-2-yl)-1,3-dihydrospiro[indene-2,3'-pyrrolidin]-2'-one

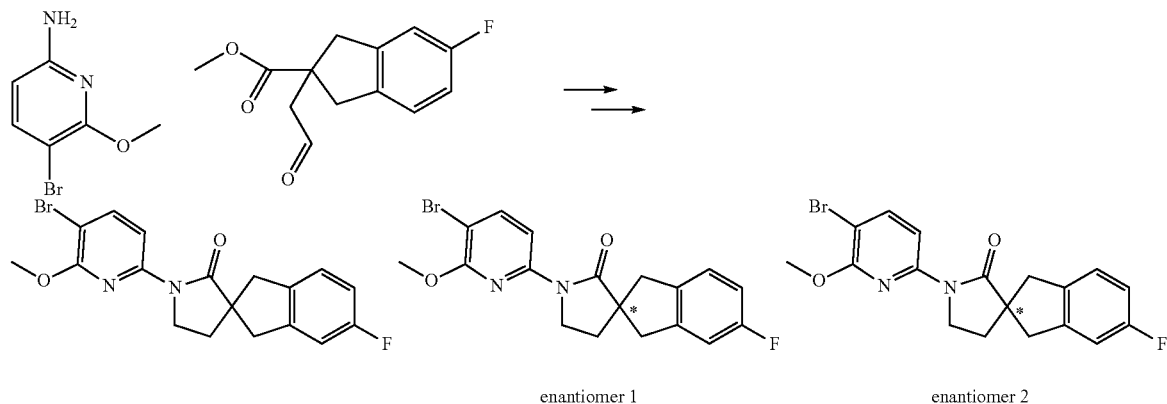

Prepared using a procedure analogous to EXAMPLE 1E through 1F except that 1-tert-butyl 2-methyl 2-(2-oxoethyl)indoline-1,2-dicarboxylate, EXAMPLE 1D and 4-bromoaniline were replaced with methyl 5-fluoro-2-(2-oxoethyl)-2,3-dihydro-1H-indene-2-carboxylate, EXAMPLE 15D and 5-bromo-6-methoxypyridin-2-amine, EXAMPLE 10A to give 1'-(5-bromo-6-methoxypyridin-2-yl)-5-fluoro-1,3-dihydrospiro[indene-2,3'-pyrrolidin]-2'-one (76 mg, 73% yield) as a white solid. MS(ESI) m/z: 391.2/393.2 (M+H)$^+$.
$^1$H NMR (400 MHz, CDCl$_3$) δ 7.94 (d, J=8.4 Hz, 1H), 7.79 (d, J=8.4 Hz, 1H), 7.14 (dd, J=8.1, 5.3 Hz, 1H), 6.95-6.81 (m, 2H), 4.08 (td. J=6.8, 1.5 Hz, 2H), 3.99 (s, 3H), 3.58-3.32 (m, 2H), 2.91 (dd, J=15.8, 6.2 Hz, 2H), 2.15 (dd, J=7.5, 6.4 Hz, 2H). The enantiomers were separated with conditions described in EXAMPLE 9C.

Enantiomer 1 RT 7.79, >99.0% enantiomeric excess.

Enantiomer 2 RT 9.12, >99.0% enantiomeric excess.

Example 17

5-Fluoro-1'-(6-methoxy-5-(1H-pyrazol-4-yl)pyridin-2-yl)-1,3-dihydrospiro[indene-2,3'-pyrrolidin]-2'-one (Enantiomer 1)

-continued

Prepared using a procedure analogous to EXAMPLE 1 except that tert-butyl 1'-(4-bromophenyl)-2'-oxospiro[indoline-2,3'-pyrrolidine]-1-carboxylate, 1F was replaced by 1'-(5-bromo-6-methoxypyridin-2-yl)-5-fluoro-1,3-dihydrospiro[indene-2,3'-pyrrolidin]-2'-one (peak 1) to give 5-fluoro-1'-(6-methoxy-5-(1H-pyrazol-4-yl)pyridin-2-yl)-1,3-dihydrospiro[indene-2,3'-pyrrolidin]-2'-one (enantiomer 1) (3.2 mg, 26% yield). MS(ESI) m/z: 479.20 (M+H)$^+$. HPLC: Method C, RT 1.95 min. $^1$H NMR (500 MHz, DMSO-d$_6$) δ 8.20-7.80 (m, 4H), 7.33-7.18 (m, 1H), 7.07 (d, J=8.8 Hz, 1H), 6.98 (t, J=8.4 Hz, 1H), 4.07 (t, J=6.4 Hz, 2H), 3.99 (s, 3H), 3.32-3.11 (m, 2H), 3.05-2.90 (m, 2H), 2.11 (t, J=6.6 Hz, 2H)

Example 18

5-Fluoro-1'-(6-methoxy-5-(1H-pyrazol-4-yl)pyridin-2-yl)-1,3-dihydrospiro[indene-2,3'-pyrrolidin]-2'-one, Enantiomer 2

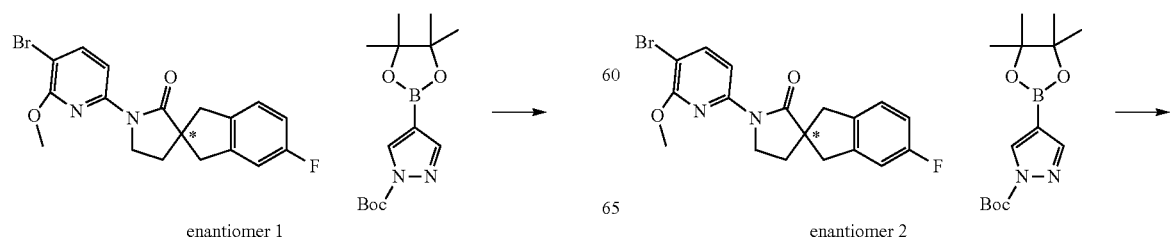

-continued

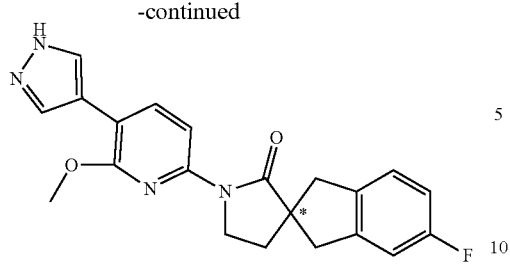

Prepared using a procedure analogous to EXAMPLE 1 except that tert-butyl 1'-(4-bromophenyl)-2'-oxospiro[indoline-2,3'-pyrrolidine]-1-carboxylate, 1F was replaced by 1'-(5-bromo-6-methoxypyridin-2-yl)-5-fluoro-1,3-dihydrospiro[indene-2,3'-pyrrolidin]-2'-one (peak 2, enantiomer 2) to give 5-fluoro-1'-(6-methoxy-5-(1H-pyrazol-4-yl)pyridin-2-yl)-1,3-dihydrospiro[indene-2,3'-pyrrolidin]-2'-one (enantiomer 2) (5 mg, 49% yield). MS(ESI) m/z: 379.3 (M+H)+. HPLC: Method C, RT 1.92 min. $^1$H NMR (500 MHz, DMSO-$d_6$) δ 8.20-7.95 (m, 3H), 7.90 (d, J=8.2 Hz, 1H), 7.27-7.19 (m, 1H), 7.07 (d, J=8.8 Hz, 1H), 6.98 (t, J=8.6 Hz, 1H), 4.06 (t, J=6.7 Hz, 2H), 3.98 (s, 3H), 3.31-3.13 (m, 2H), 2.99 (t, J=15.7 Hz, 2H), 2.11 (t, J=6.6 Hz, 2H)

Example 19

5-Methoxy-1'-(6-methoxy-5-(1H-pyrazol-4-yl)pyridin-2-yl)-1,3-dihydrospiro[indene-2,3'-pyrrolidin]-2'-one, Enantiomer 1

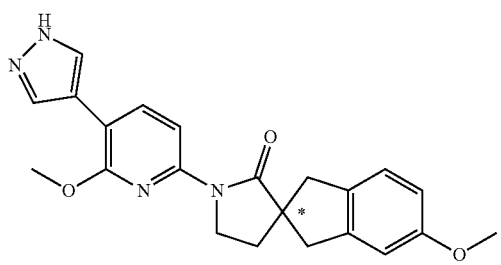 [SMILES: COc1ccc2c(c1)CC1(CCN(c3ccc(-c4cn[nH]c4)c(OC)n3)C1=O)C2]

Example 19A. Methyl 5-methoxy-2-(2-oxoethyl)-2,3-dihydro-1H-indene-2-carboxylate

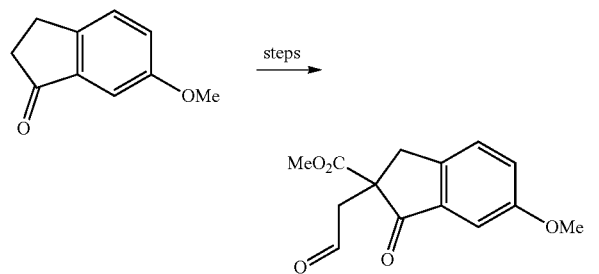

Prepared using a procedure analogous to EXAMPLE 15A-15D except that 6-fluoro-2,3-dihydro-1H-indene-1-one was replaced with and 6-methoxy-2,3-dihydro-1H-inden-1-one to give methyl 5-methoxy-2-(2-oxoethyl)-2,3-dihydro-1H-indene-2-carboxylate (239 mg, 67% yield) as a brown oil. MS(ESI) m/z: 249.2 (M+H)+. $^1$H NMR (400 MHz, CDCl$_3$) δ 9.72 (t, J=1.2 Hz, 1H), 7.07 (d, J=9.0 Hz, 1H), 6.77-6.67 (m, 2H), 3.78 (s, 3H), 3.74-3.68 (m, 3H), 3.62-3.43 (m, 2H), 2.94-2.83 (m, 4H)

Example 19B. 5-Methoxy-1'-(6-methoxy-5-(1H-pyrazol-4-yl)pyridin-2-yl)-1,3-dihydrospiro[indene-2,3'-pyrrolidin]-2'-one

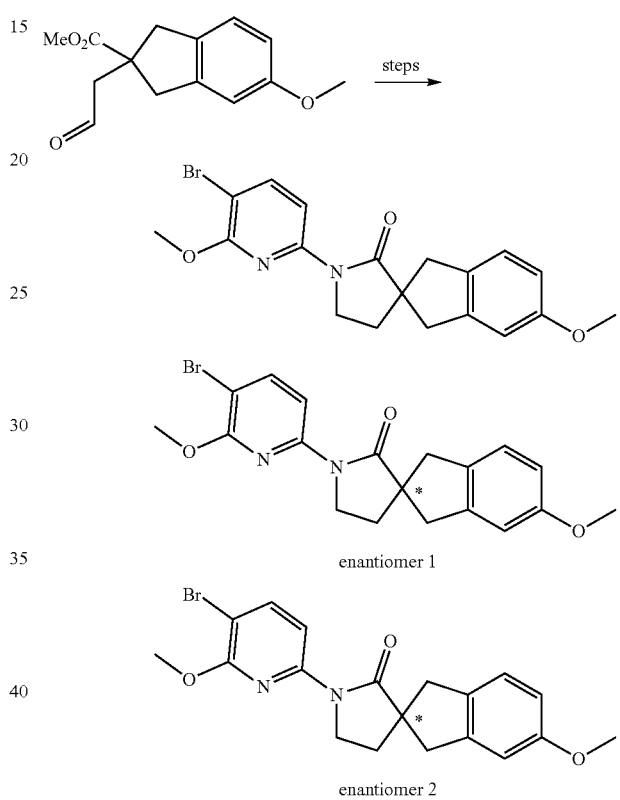

Prepared using a procedure analogous to EXAMPLE 1D through EXAMPLE 1F except that 1-tert-butyl 2-methyl 2-(2-oxoethyl)indoline-1,2-dicarboxylate, EXAMPLE 1D was replaced by methyl 5-methoxy-2-(2-oxoethyl)-2,3-dihydro-1H-indene-2-carboxylate and bromoaniline was replaced with 5-bromo-6-methoxypyridine-2-amine to give 1'-(5-bromo-6-methoxypyridin-2-yl)-5-methoxy-1,3-dihydrospiro[indene-2,3'-pyrrolidin]-2'-one (27 mg, 32% yield) as a white solid. MS(ESI) m/z: 403.2/405.2 (M+H)+. $^1$H NMR (400 MHz, CDCl$_3$) δ 7.95 (d, J=8.6 Hz, 1H), 7.78 (d, 1=8.6 Hz, 1H), 7.11 (d, J=8.1 Hz, 1H), 6.83-6.68 (m, 2H), 4.12-4.03 (m, 2H), 3.99 (s, 3H), 3.79 (s, 3H), 3.53-3.34 (m, 2H), 2.88 (dd, J=15.6, 5.9 Hz, 2H), 2.20-2.09 (m, 2H).

The enantiomers were separated with conditions described in EXAMPLE 15E except mobile phase: 20% MeOH/80% CO$_2$.

Enantiomer 1 RT 7.990, >99.0% enantiomeric excess.

Enantiomer 2 RT 10.816, >99.0% enantiomeric excess.

Example 19

5-Methoxy-1'-(6-methoxy-5-(1H-pyrazol-4-yl)pyridin-2-yl)-1,3-dihydrospiro[indene-2,3'-pyrrolidin]-2'-one, Enantiomer 1

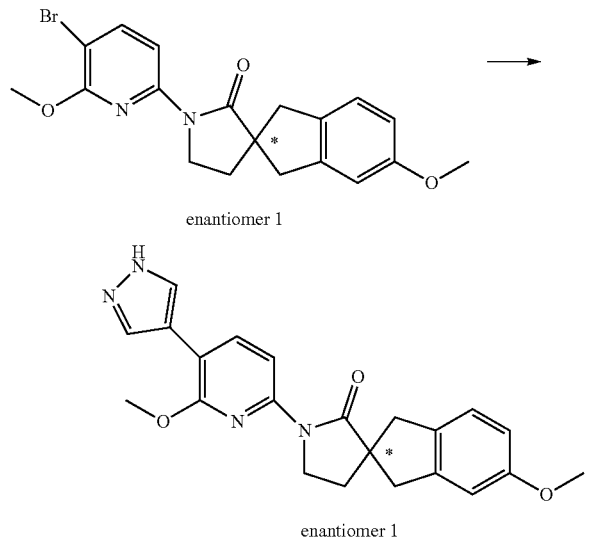

Prepared using a procedure analogous to EXAMPLE 1 except that tert-butyl 1'-(4-bromophenyl)-2'-oxospiro[indoline-2,3'-pyrrolidine]-1-carboxylate, 1F was replaced with 1'-(5-bromo-6-methoxypyridin-2-yl)-5-methoxy-1,3-dihydrospiro[indene-2,3'-pyrrolidin]-2'-one (enantiomer 1) to give 5-methoxy-1'-(6-methoxy-5-(1H-pyrazol-4-yl)pyridin-2-yl)-1,3-dihydrospiro[indene-2,3'-pyrrolidin]-2'-one, Enantiomer 1 (6.5 mg, 53% yield). MS(ESI) m/z: 391.1 (M+H)+. $^1$H NMR (400 MHz, DMSO-$d_6$) δ 8.09 (d, J=8.4 Hz, 3H), 7.94 (d, J=8.1 Hz, 1H), 7.14 (d, J=8.4 Hz, 1H), 6.84 (s, 1H), 6.76 (dd, J=8.1, 2.4 Hz, 1H), 4.09 (t, J=7.4 Hz, 2H), 4.02 (s, 3H), 3.75 (s, 3H), 3.30-3.16 (m, 4H), 3.05-2.87 (m, 2H), 2.12 (t, J=6.8 Hz, 2H). HPLC Method A, RT=5.09 min, 97% purity; Method B, RT=6.99 min. 95% purity.

Example 20

5-Methoxy-1'-(6-methoxy-5-(1H-pyrazol-4-yl)pyridin-2-yl)-1,3-dihydrospiro[indene-2,3'-pyrrolidin]-2'-one, Enantiomer 2

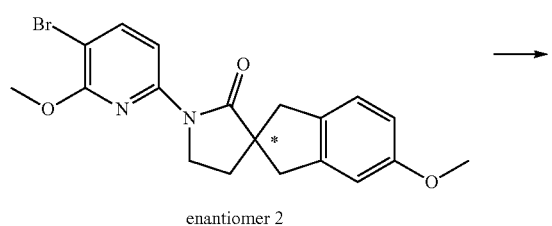

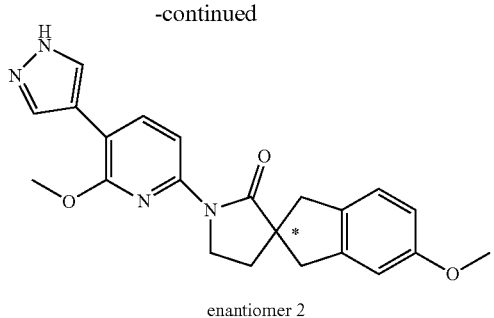

Prepared using a procedure analogous to EXAMPLE 1 except that tert-butyl 1'-(4-bromophenyl)-2'-oxospiro[indoline-2,3'-pyrrolidine]-1-carboxylate, 1F was replaced with 1'-(5-bromo-6-methoxypyridin-2-yl)-5-methoxy-1,3-dihydrospiro[indene-2,3'-pyrrolidin]-2'-one (enantiomer 2) to give 5-methoxy-1'-(6-methoxy-5-(1H-pyrazol-4-yl)pyridin-2-yl)-1,3-dihydrospiro[indene-2,3'-pyrrolidin]-2'-one, Enantiomer 2 (3.1 mg, 26% yield). MS(ESI) m/z: 391.3 (M+H)+. HPLC: Method C, Purity 98%, RT 1.85 min. $^1$H NMR (500 MHz, DMSO-$d_6$) δ 8.14 (br. s., 1H), 8.06 (d, J=8.2 Hz, 1H), 7.99 (br. s., 1H), 7.91 (d, J=8.2 Hz, 1H), 7.12 (d, J=8.2 Hz, 1H), 6.82 (s, 1H), 6.73 (d, J=8.0 Hz, 1H), 4.06 (br. s., 2H), 3.99 (s, 3H), 3.71 (s, 3H), 3.29-3.10 (m, 2H), 2.93 (t, J=16.8 Hz, 2H), 2.09 (t, J=6.6 Hz, 2H).

Example 21

1'-(4-(1H-Pyrazol-4-yl)phenyl)-5-methoxy-1,3-dihydrospiro[indene-2,3'-pyrrolidin]-2'-one, Enantiomer 1

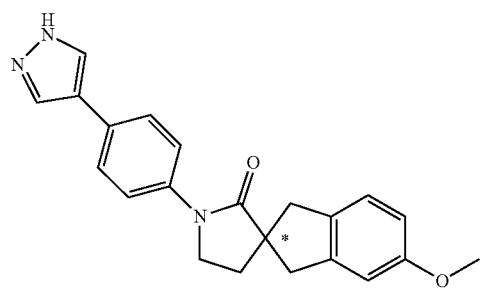 [SMILES: COc1ccc2c(c1)CC1(CCN(c3ccc(-c4cn[nH]c4)cc3)C1=O)C2]

Example 21A. 1'-(4-Bromophenyl)-5-methoxy-1,3-dihydrospiro[indene-2,3'-pyrrolidin]-2'-one

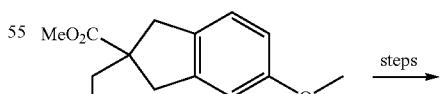

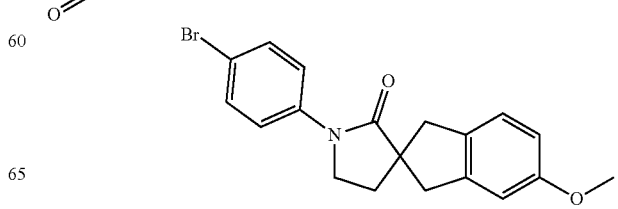

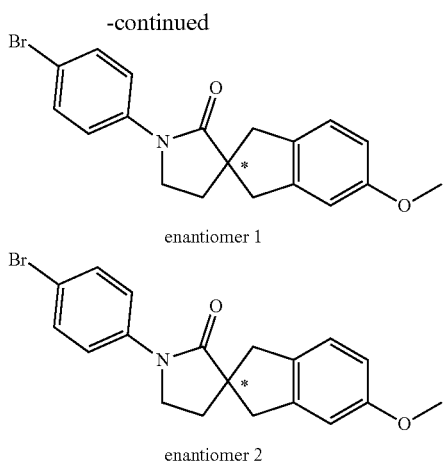

enantiomer 1 enantiomer 2

Prepared using a procedure analogous to EXAMPLE 1E through EXAMPLE 1F except that 1-tert-butyl 2-methyl 2-(2-oxoethyl)indoline-1,2-dicarboxylate, EXAMPLE 1D was replaced by methyl 5-methoxy-2-(2-oxoethyl)-2,3-dihydro-1H-indene-2-carboxylate, EXAMPLE 19A and bromoaniline was replaced with 5-bromo-6-methoxypyridine-2-amine, EXAMPLE 10A to give 1'-(4-bromophenyl)-5-methoxy-1,3-dihydrospiro[indene-2,3'-pyrrolidin]-2'-one (78 mg, 86% yield) as a white solid. MS(ESI) m/z: 372/374.2 (M+H)+. 1H NMR (400 MHz, CDCl3) δ 7.68-7.54 (m, 2H), 7.54-7.43 (m, 2H), 7.11 (d, J=8.1 Hz, 1H), 6.84-6.69 (m, 2H), 3.87-3.75 (m, 5H), 3.54-3.34 (m, 2H), 2.86 (dd, J=15.4, 6.4 Hz, 2H), 2.25-2.11 (m, 2H).

The enantiomers were separated by chiral chromatography.

Analytical chiral chromatographic conditions: Chiralpak AS-H, 4.6×250 mm, 5 micron. Mobile phase: 25% MeOH/75% CO2. Flow: 2.0 mL/min, 150 Bar, 40° C.

Preparative chiral chromatographic conditions: Chiralpak AS-H, 21×250 mm, 5 micron. Mobile phase: 25% MeOH/75% CO2. Flow: 45 mL/min, 100 Bar, 40° C.

Enantiomer 1 RT 8.97 min, >99.0% enantiomeric excess, 1'-(4-bromophenyl)-5-methoxy-1,3-dihydrospiro[indene-2,3'-pyrrolidin]-2'-one, peak 1 (39.2 mg, 50% yield) isolated as a white solid. MS(ESI) m/z: 372.0/374.0 (M+H)+.

Enantiomer 2 RT 11.44 min, 98.0% enantiomeric excess, 1'-(4-bromophenyl)-5-methoxy-1,3-dihydrospiro[indene-2,3'-pyrrolidin]-2'-one, peak 2 (32.6 mg, 42% yield) isolated as a white solid. MS(ESI) m/z: 372.0/374.1 (M+H)+.

Example 21

1'-(4-(1H-Pyrazol-4-yl)phenyl)-5-methoxy-1,3-dihydrospiro[indene-2,3'-pyrrolidin]-2'-one, Enantiomer 1

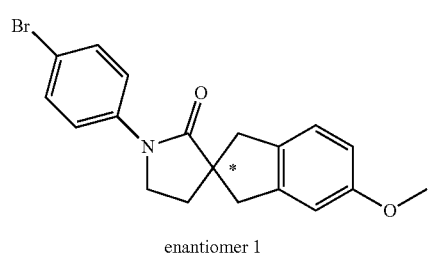

enantiomer 1

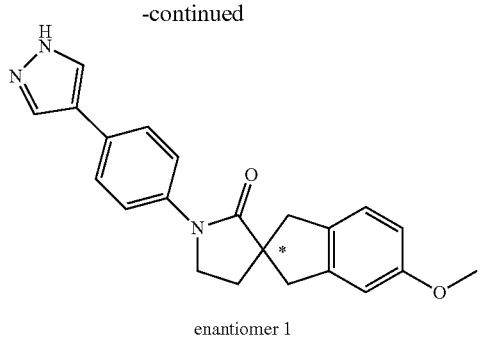

enantiomer 1

Prepared using a procedure analogous to EXAMPLE 1 except that tert-butyl 1'-(4-bromophenyl)-2'-oxospiro[indoline-2,3'-pyrrolidine]-1-carboxylate, 1F was replaced with 1'-(4-bromophenyl)-5-methoxy-1,3-dihydrospiro[indene-2,3'-pyrrolidin]-2'-one, peak 1 to give 1'-(4-(1H-pyrazol-4-yl)phenyl)-5-methoxy-1,3-dihydrospiro[indene-2,3'-pyrrolidin]-2'-one, Enantiomer 1 (6.7 mg, 32% yield). MS(ESI) m/z: 360.1 (M+H)+. 1H NMR (400 MHz, DMSO-d6) δ 8.19 (s, 1H), 7.93 (s, 1H), 7.77-7.60 (m, 4H), 7.14 (d, J=8.1 Hz, 1H), 6.84 (s, 1H), 6.79-6.70 (m, 1H), 3.88 (t, J=6.8 Hz, 2H), 3.75 (s, 3H), 3.29-3.12 (m, 2H), 3.02-2.84 (m, 2H), 2.13 (t, J=6.7 Hz, 2H). HPLC: Method A. RT=4.74 min, 93% purity; Method B, RT=6.83 min, 95% purity.

Example 22

1'-(4-(1H-Pyrazol-4-yl)phenyl)-5-methoxy-1,3-dihydrospiro[indene-2,3'-pyrrolidin]-2'-one, Enantiomer 2

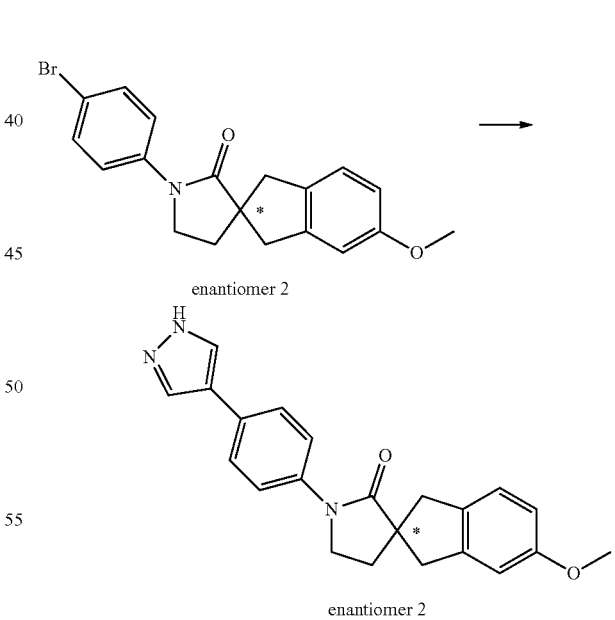

enantiomer 2 enantiomer 2

Prepared using a procedure analogous to EXAMPLE 1 except that tert-butyl 1'-(4-bromophenyl)-2'-oxospiro[indoline-2,3'-pyrrolidine]-1-carboxylate, EXAMPLE 1F was replaced with 1'-(4-bromophenyl)-5-methoxy-1,3-dihydrospiro[indene-2,3'-pyrrolidin]-2'-one, peak 2 to give 1'-(4-(1H-pyrazol-4-yl)phenyl)-5-methoxy-1,3-dihydrospiro[indene-2,3'-pyrrolidin]-2'-one, Enantiomer 2 (3.6 mg, 37% yield). MS(ESI) m/z: 360.3 (M+H)+. HPLC: Method C. Purity 99%, RT 1.61 min. $^1$H NMR (500 MHz, DMSO-d$_6$) δ 8.03 (br. s., 2H), 7.73-7.65 (m, 2H), 7.65-7.58 (m, 2H), 7.12 (d, J=8.2 Hz, 1H), 6.82 (s, 1H), 6.73 (d, J=8.6 Hz, 1H), 3.85 (t, J=6.6 Hz, 2H), 3.71 (s, 3H), 3.25-3.09 (m, 2H), 2.91 (t, J=16.8 Hz, 2H), 2.10 (t, J=6.2 Hz, 2H).

Example 23

1'-(6-Methoxy-5-(1H-pyrazol-4-yl)pyridin-2-yl)-1,3-dihydrospiro[indene-2,3'-pyrrolidin]-2'-one

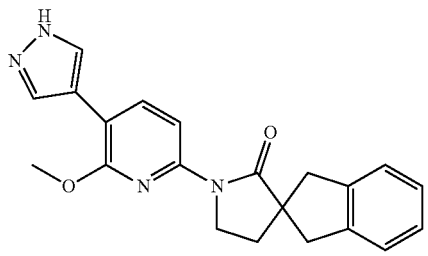 [SMILES: COc1nc(N2CCC3(Cc4ccccc4C3)C2=O)ccc1-c1cn[nH]c1]

Prepared using a procedure analogous to EXAMPLE 1. Except in the synthesis of methyl indoline-2-carboxylate, EXAMPLE 1A, indoline-2-carboxylic acid was replaced with 2,3-dihydro-1H-indene-2-carboxylic acid and in the synthesis of 1-tert-butyl 2-methyl 2-(2-((4-bromophenyl)amino)ethyl)indoline-1,2-dicarboxylate, EXAMPLE 1E, bromoaniline was replaced with 5-bromo-6-methoxypyridine-2-amine. EXAMPLE 10A to give 1'-(6-methoxy-5-(1H-pyrazol-4-yl)pyridin-2-yl)-1,3-dihydrospiro[indene-2,3'-pyrrolidin]-2'-one (1.9 mg, 15% yield). MS(ESI) m/z: 360.9 (M+H)+. HPLC: Method C. RT 1.82 min. $^1$H NMR (500 MHz, DMSO-d$_6$) δ 8.21-7.97 (m, 3H), 7.91 (d, J=8.2 Hz, 1H), 7.23 (d, J=3.4 Hz, 2H), 7.20-7.13 (m, 2H), 4.07 (t, J=6.7 Hz, 2H), 3.99 (s, 3H), 3.26 (d, J=15.9 Hz, 2H), 3.00 (d, J=15.9 Hz, 2H), 2.10 (t, J=6.7 Hz, 2H)

Example 24

1'-(4-(1H-Pyrazol-4-yl)phenyl)-5-methoxy-3H-spiro[benzofuran-2,3'-pyrrolidin]-2'-one

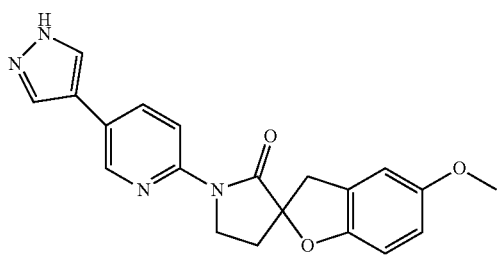 [SMILES: COc1ccc2c(c1)CC1(CCN(c3ccc(-c4cn[nH]c4)cn3)C1=O)O2]

Example 24A. Methyl 5-methoxy benzofuran-2-carboxylate

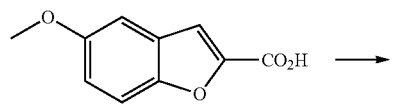

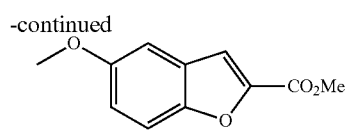

To a solution of 5-methoxybenzofuran-2-carboxylic acid (2000 mg, 10.41 mmol)) in CH$_2$Cl$_2$ (30 mL) and methanol (3 mL) in ice bath was added 2M TMS-diazomethane (6.76 mL, 13.53 mmol) dropwise. The reaction was stirred at 0° C. for 0.5 h. The reaction was concentrated and the beige solid was filtered and washed with hexane to give methyl 5-methoxybenzofuran-2-carboxylate (1.96 g, 91% yield). MS(ESI) m/z: 207.0 (M+H)+. $^1$H NMR (400 MHz, CDCl$_3$) δ 7.59-7.40 (m, 2H), 7.14-7.00 (m, 2H), 3.97 (s, 3H), 3.85 (s, 3H).

Example 24B. Methyl 5-methoxy-2,3-dihydrobenzofuran-2-carboxylate

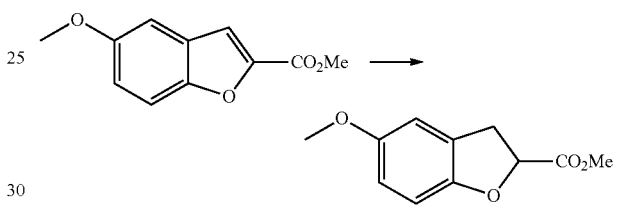

Methyl 5-methoxybenzofuran-2-carboxylate (1.98 g, 9.60 mmol) was dissolved in ethanol (100 mL) in a hydrogenation flask. The solution was bubbled with N$_2$ for 5 minutes then palladium on carbon (10%) (0.34 g, 3.19 mmol) was added. The reaction was hydrogenated over 55 psi of hydrogen overnight. The mixture was filtered, washed with EtOH and EtOAc and additional 500 mg 10% Pd/C was added. Hydrogenated at 55 psi H2 with 500 mg Pd/C for 6 days. The mixture was filtered through Celite and concentrated to give methyl 5-methoxy-2,3-dihydrobenzofuran-2-carboxylate (1.9 g, 95% yield) as a clear yellow oil. MS(ESI) m/z: 209.0 (M+H)+. $^1$H NMR (400 MHz, CDCl$_3$) δ 6.80 (d, J=8.8 Hz, 1H), 6.77-6.73 (m, 1H), 6.72-6.65 (m, 1H), 5.20 (dd, J=10.6, 6.8 Hz, 1H), 3.81 (s, 3H), 3.76-3.72 (m, 3H), 3.54 (dd, J=16.1, 10.3 Hz, 1H), 3.42-3.31 (m, 1H)

Example 24

1'-(4-(1H-Pyrazol-4-yl)phenyl)-5-methoxy-3H-spiro[benzofuran-2,3'-pyrrolidin]-2'-one

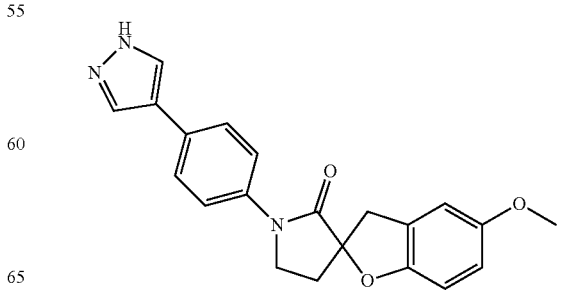

Prepared using a procedure analogous to EXAMPLE 1 except that 1-tert-butyl 2-methyl indoline-1,2-dicarboxylate, EXAMPLE 1B was replaced by methyl 5-methoxy-2,3-dihydrobenzofuran-2-carboxylate to give 1'-(4-(1H-pyrazol-4-yl)phenyl)-5-methoxy-3H-spiro[benzofuran-2,3'-pyrrolidin]-2'-one (2.7 mg, 54% yield). MS(ESI) m/z: 362.0 (M+H)+.

HPLC: Method C, RT 1.39 min. $^1$H NMR (500 MHz, DMSO-$d_6$) δ 8.18 (br. s., 1H), 7.93 (br. s., 1H), 7.75-7.68 (m, 2H), 7.68-7.61 (m, 2H), 6.87 (s, 1H), 6.69 (s, 2H), 3.95 (d, J=6.8 Hz, 1H), 3.86 (br. s., 1H), 3.69 (s, 3H), 3.28 (d, J=16.4 Hz, 1H), 2.44 (dd, J=15.5, 7.4 Hz, 2H)

Example 25

1'-(4-(1H-Pyrazol-4-yl)phenyl)-5-methoxy-3H-spiro[benzofuran-2,3'-pyrrolidin]-2'-one, Enantiomer 1

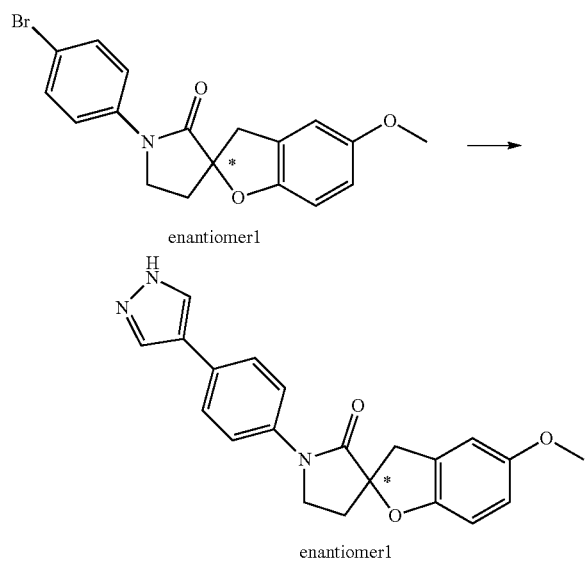

Prepared analogous to EXAMPLE 24 where 1'-(4-bromophenyl)-5-methoxy-3H-spiro[benzofuran-2,3'-pyrrolidin]-2'-one was replaced by 1'-(4-bromophenyl)-5-methoxy-3H-spiro[benzofuran-2,3'-pyrrolidin]-2'-one, Enantiomer 1.

Chiral separation of 1'-(4-bromophenyl)-5-methoxy-3H-spiro[benzofuran-2,3'-pyrrolidin]-2'-one was accomplished using the conditions below, Preparative: Chiralcel OJ-H, 21×250 mm, 5 micron. 25% MeOH/75% $CO_2$ at 45 mL/min. 150 Bar, 40° C.

Analytical: Chiralcel OJ-H, 4.6×250 mm, 5 micron. 25% MeOH/75% $CO_2$ at 2 mL/min, 150 Bar, 40° C.

Enantiomer 1, RT 11.33 min, enantiomeric excess >99.0%

Enantiomer 2, RT 15.26 min, enantiomeric excess >96.6%

1'-(4-(1H-Pyrazol-4-yl)phenyl)-5-methoxy-3H-spiro[benzofuran-2,3'-pyrrolidin]-2'-one, enantiomer 1 (13 mg, 43% yield) isolated as a white solid. MS(ESI) m/z: 362.1 (M+H)+. HPLC: Method A, RT=7.13 min, 95.4% purity; Method B, RT=8.83 min, 98.6% purity. $^1$H NMR (400 MHz, DMSO-$d_6$) δ 8.09 (br. s., 2H), 7.81-7.72 (m, 2H), 7.71-7.61 (m, 2H), 6.89 (d, J=0.9 Hz, 1H), 6.76-6.64 (m, 2H), 4.05-3.93 (m, 1H), 3.91-3.81 (m, 1H), 3.71 (s, 3H), 3.51 (d, J=16.7 Hz, 1H), 3.29-3.12 (m, 1H), 2.48-2.38 (m, 2H)

Example 26

1'-(4-(1H-Pyrazol-4-yl)phenyl)-5-methoxy-3H-spiro[benzofuran-2,3'-pyrrolidin]-2'-one, Enantiomer 2

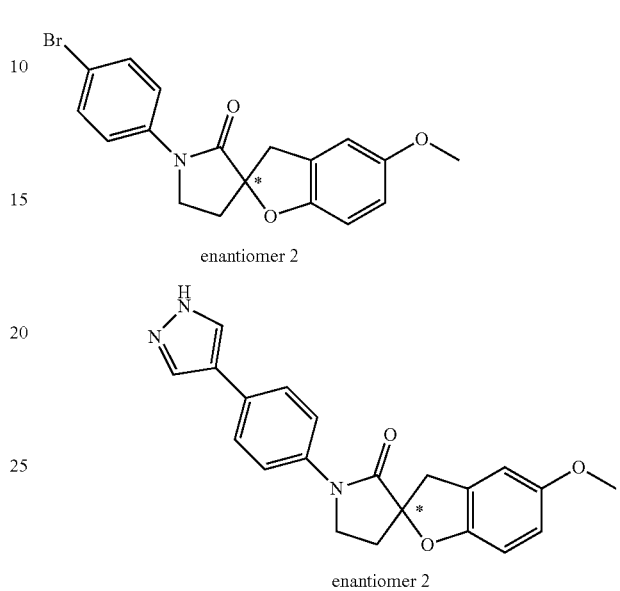

Prepared analogous to EXAMPLE 24 where 1'-(4-bromophenyl)-5-methoxy-3H-spiro[benzofuran-2,3'-pyrrolidin]-2'-one was replaced by 1'-(4-bromophenyl)-5-methoxy-3H-spiro[benzofuran-2,3'-pyrrolidin]-2'-one, Enantiomer 2. 1'-(4-(1H-Pyrazol-4-yl)phenyl)-5-methoxy-3H-spiro[benzofuran-2,3'-pyrrolidin]-2'-one, Enantiomer 2 (12 mg, 40% yield) as white solid. MS(ESI) m/z: 362.1 (M+H)+. HPLC: Method A. RT=7.14 min, 96.4% purity; Method B, RT=8.83 min. 97.4% purity. $^1$H NMR (400 MHz, DMSO-$d_6$) δ 8.09 (br. s., 2H), 7.79-7.71 (m, 2H), 7.70-7.61 (m, 2H), 6.89 (d, J=1.1 Hz, 1H), 6.76-6.66 (m, 2H), 4.04-3.92 (m, 1H), 3.91-3.83 (m, 1H), 3.71 (s, 3H), 3.51 (d, J=16.9 Hz, 1H), 3.32-3.24 (m, 1H), 2.50-2.35 (m, 2H)

Example 27

1'-(4-(1H-Pyrazol-4-yl)phenyl)-4-methylspiro[indoline-2,3'-pyrrolidin]-2'-one

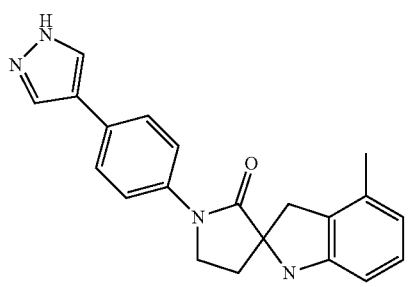 [SMILES: Cc1cccc2c1CC1(CCN(c3ccc(-c4cn[nH]c4)cc3)C1=O)N2]

Example 27A. Methyl 4-methyl-1H-indole-2-carboxylate

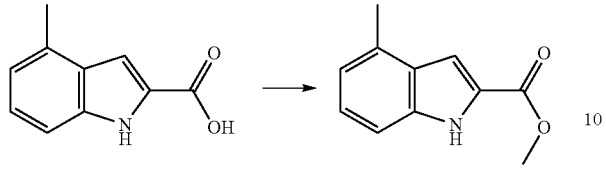

To a solution of 4-methyl-1H-indole-2-carboxylic acid (0.5 g, 2.85 mmol) in MeOH (5 mL) was added sulfuric acid (0.25 ml, 4.69 mmol) dropwise and heated at 65° C. o.n. The reaction was diluted with EtOAc, neutralized with 1M $K_2HPO_4$, extracted with EtOAc (2×). The combined organic layers were washed with brine, dry $MgSO_4$ and concentrated to give methyl 4-methyl-1H-indole-2-carboxylate as a brown solid which was used without further purification. MS(ESI) m-z: 190.1 $(M+H)^3$. $^1$H NMR (400 MHz, CDCl$_3$) δ 7.36-7.18 (m, 4H), 6.95 (d, J=6.8 Hz, 1H), 3.95 (s, 3H), 2.57 (s, 3H).

EXAMPLE 27. 1'-(4-(1H-Pyrazol-4-yl)phenyl)-4-methylspiro[indoline-2,3'-pyrrolidin]-2'-one was prepared using a procedure analogous to EXAMPLE 4 except that in EXAMPLE 4A, methyl 6-methoxy-1H-indole-2-carboxylate was replaced by methyl 4-methyl-1H-indole-2-carboxylate and NaBH$_3$CN in MeOH was used in the reductive amination to give 1'-(4-(1H-pyrazol-4-yl)phenyl)-4-methylspiro[indoline-2,3'-pyrrolidin]-2'-one (3.3 mg, 21% yield). MS(ESI) m/z: 345.0 $(M+H)^+$. HPLC: Method C RT 1.33 min. $^1$H NMR (500 MHz, DMSO-d$_6$) δ 8.13 (br. s., 1H), 7.93 (br. s., 1H), 7.74-7.55 (m, 4H), 6.84 (t, J=7.5 Hz, 1H), 6.47-6.25 (m, 2H), 6.19 (s, 1H), 3.81 (d, J=6.2 Hz, 1H), 3.73-3.52 (m, 1H), 3.21-2.91 (m, 2H), 2.32-2.13 (m, 2H), 2.10 (s, 3H)

Example 28

1-(4-(1H-Pyrazol-4-yl)phenyl)-1',3'-dihydrospiro[pyrrolidine-3,2'-pyrrolo[3,2-b]pyridin]-2-one

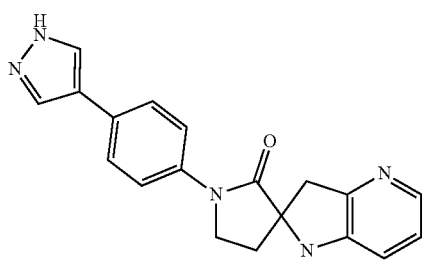 [SMILES: O=C1N(c2ccc(-c3cn[nH]c3)cc2)CCC12Cc1ncccc1N2]

Prepared using a procedure analogous to EXAMPLE 4 except that methyl 6-methoxy-1H-indole-2-carboxylate was replaced by methyl 1H-pyrrolo[3,2-b]pyridine-2-carboxylate and NaBH$_3$CN in MeOH was used in the reductive amination as in EXAMPLE 1E to give 1-(4-(1H-pyrazol-4-yl)phenyl)-1',3'-dihydrospiro[pyrrolidine-3,2'-pyrrolo[3,2-b]pyridin]-2-one (0.9 mg, 13%). MS(ESI) m/z: 332.1 $(M+H)^+$. HPLC: Method C, RT 0.58 min. $^1$H NMR (500 MHz, DMSO-d$_6$) δ 8.04 (br. s., 2H), 7.81-7.57 (m, 5H), 6.99-6.87 (m, 1H), 6.75 (d, J=7.7 Hz, 1H), 3.97-3.74 (m, 2H), 3.41-3.09 (m, 2H), 2.42-2.32 (m, 1H), 2.29-2.15 (m, 1H)

Example 29

1'-(4-(1H-Pyrazol-4-yl)phenyl)-3H-spiro[benzofuran-2,3'-pyrrolidin]-2'-one racemate

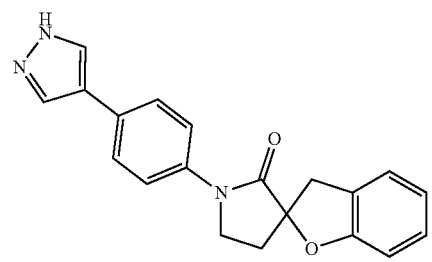 [SMILES: O=C1N(c2ccc(-c3cn[nH]c3)cc2)CCC12Cc1ccccc1O2]

Prepared using a procedure analogous to EXAMPLE 24 except that methyl 5-hydroxy-2,3-dihydrobenzofuran-2-carboxylate was replaced by 2,3-dihydrobenzofuran-2-carboxylic acid to give 1'-(4-(1H-pyrazol-4-yl)phenyl)-3H-spiro[benzofuran-2,3'-pyrrolidin]-2'-one (3 mg, 20% yield) as a white solid. MS(ESI) m/z: 332.1 $(M+H)^+$. HPLC: Method A, RT=7.43 min, 94.8% purity; Method B, RT=9.12 min, 100% purity. $^1$H NMR (400 MHz, DMSO-d$_6$) δ 8.21 (br. s., 1H), 7.94 (br. s., 1H), 7.77-7.71 (m, 2H), 7.70-7.64 (m, 2H), 7.27 (d, J=6.6 Hz, 1H), 7.15 (t, J=7.2 Hz, 1H), 6.90 (td, J=7.4, 1.0 Hz, 1H), 6.81 (d, J=8.1 Hz, 1H), 4.00 (dt, J=9.9, 6.8 Hz, 1H), 3.94-3.85 (m, 1H), 3.54 (d, J=16.5 Hz, 1H)

Example 30

1'-(4-(1H-Pyrazol-4-yl)phenyl)-3H-spiro[benzofuran-2,3'-pyrrolidin]-2'-one Enantiomer 1

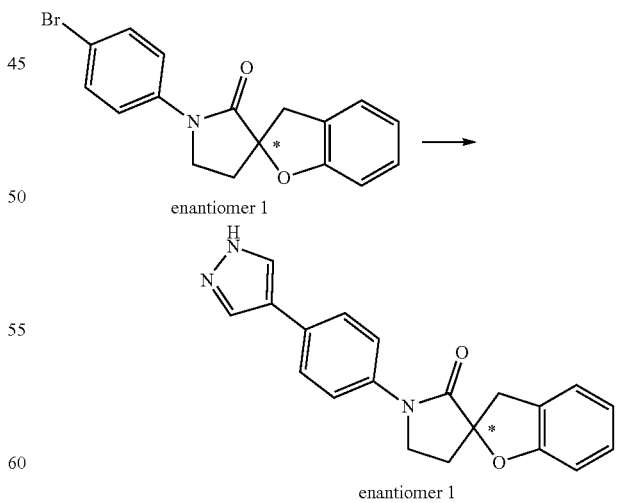

Prepared analogously to EXAMPLE 1 where tert-butyl 1'-(4-bromophenyl)-2'-oxospiro[indoline-2,3'-pyrrolidine]-1-carboxylate, enantiomer 1 was replaced by 1'-(4-bromophenyl)-3H-spiro[benzofuran-2,3'-pyrrolidin]-2'-one, Enantiomer 1. Chiral separation of 1'-(4-bromophenyl)-3H-spiro[benzofuran-2,3'-pyrrolidin]-2'-one was accomplished using the conditions described in EXAMPLE 1F except the mobile phase: 25% MeOH/75% $CO_2$. 1'-(4-(1H-Pyrazol-4-yl)phenyl)-3H-spiro[benzofuran-2,3'-pyrrolidin]-2'-one, Enantiomer 1 (17 mg, 49% yield) as a white solid. MS(ESI) m/z: 332.1 (M+H)$^+$. HPLC: Method A, RT=7.34 min, 97.3% purity; Method B, RT=9.04 min, 97.7% purity, 1H NMR (400 MHz, DMSO-$d_6$) δ 8.08 (br. s., 2H), 7.80-7.71 (m, 2H), 7.71-7.62 (m, 2H), 7.32-7.19 (m, 1H), 7.17-7.07 (m, 1H), 6.90 (td, J=7.5, 0.9 Hz, 1H), 6.81 (d, J=7.9 Hz, 1H), 4.04-3.95 (m, 1H), 3.93-3.82 (m, 1H), 3.53 (d, J=16.1 Hz, 2H), 3.37-3.26 (m, 2H), 2.50-2.39 (m, 2H)

Example 31

1'-(4-(1H-Pyrazol-4-yl)phenyl)-3H-spiro[benzofuran-2,3'-pyrrolidin]-2'-one Enantiomer 2

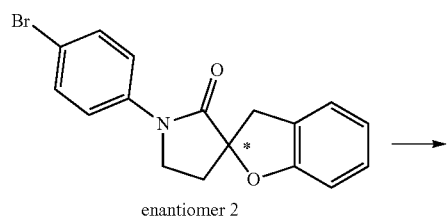

enantiomer 2

Prepared analogously to EXAMPLE 1 where tert-butyl 1'-(4-bromophenyl)-2'-oxospiro[indoline-2,3'-pyrrolidine]-1-carboxylate, enantiomer 1 was replaced by 1'-(4-bromophenyl)-3H-spiro[benzofuran-2,3'-pyrrolidin]-2'-one, Enantiomer 2 to afford 1'-(4-(1H-pyrazol-4-yl)phenyl)-3H-spiro[benzofuran-2,3'-pyrrolidin]-2'-one, Enantiomer 2 (15 mg, 43% yield) as a white solid. MS(ESI) m/z: 332.1 (M+H)$^+$. HPLC: Method A, RT=7.36 min, 96.8% purity; Method B. RT=9.05 min, 96.8% purity. $^1$H NMR (400 MHz, DMSO-$d_6$) δ 8.08 (br. s., 2H), 7.79-7.72 (m, 2H), 7.72-7.63 (m, 2H), 7.33-7.23 (m, 1H), 7.18-7.07 (m, 1H), 6.90 (td, J=7.5, 0.9 Hz, 1H), 6.81 (d, J=7.9 Hz, 1H), 4.04-3.95 (m, 1H), 3.93-3.83 (m, 1H), 3.53 (d, J=16.3 Hz 1H), 3.35-3.27 (m, 1H), 2.50-2.39 (m, 2H)

Example 32

1'-(4-(1H-Pyrazol-4-yl)phenyl)-3H-spiro[benzofuran-2,3'-pyrrolidin]-2'-one, Racemic

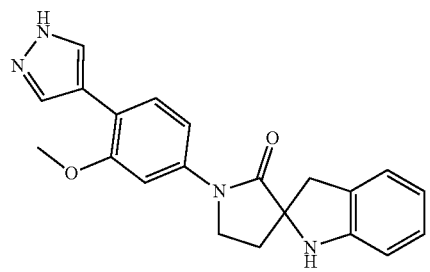 [SMILES: COc1cc(N2CCC3(Cc4ccccc4N3)C2=O)ccc1-c1cn[nH]c1]

Prepared using a procedure analogous to EXAMPLE 1 except that in step 1E, 4-bromoaniline was replaced by 4-bromo-3-methoxyaniline to give 1'-(3-methoxy-4-(1H-pyrazol-4-yl)phenyl)spiro[indoline-2,3'-pyrrolidin]-2'-one (6 mg, 39% yield) as an off-white solid. MS(ESI) m/z: 361.1 (M+H)$^+$. HPLC: Method A. RT=6.67 min, 98.9% purity; Method B. RT=8.43 min, 98.9% purity. $^1$H NMR (400 MHz, DMSO-$d_6$) δ 8.04 (br. s., 2H), 7.70-7.62 (m, 2H), 7.21 (dd, J=8.5, 2.1 Hz, 1H), 7.01 (d, J=7.3 Hz, 1H), 6.96 (t, J=7.0 Hz, 1H), 6.61-6.54 (m, 1H), 6.49 (d, J=7.7 Hz, 1H), 6.33 (br. s., 1H), 3.97-3.78 (m, 5H), 3.29-3.03 (m, 2H), 2.37-2.15 (m, 2H)

Example 33

1'-(4-(1H-Pyrazol-4-yl)phenyl)-3H-spiro[benzofuran-2,3'-pyrrolidin]-2'-one, Enantiomer

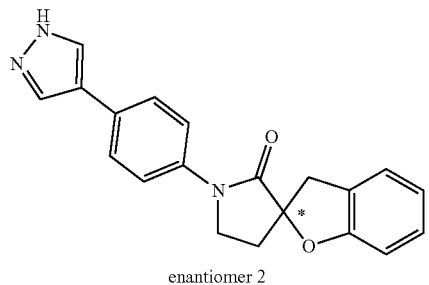

enantiomer 1

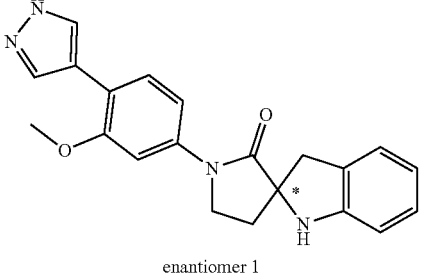

enantiomer 1

Prepared analogously to EXAMPLE 1 where tert-butyl 1'-(4-bromophenyl)-2'-oxospiro[indoline-2,3'-pyrrolidine]-1-carboxylate, EXAMPLE 1G enantiomer 1 was replaced by 1'-(4-bromophenyl)-3H-spiro[benzofuran-2,3'-pyrrolidin]-2'-one, enantiomer 1. Chiral separation of tert-butyl 1'-(4-bromo-3-methoxyphenyl)-2'-oxospiro[indoline-2,3'-pyrrolidine]-1-carboxylate was accomplished using the conditions described in EXAMPLE 1G except the mobile phase: 20% MeOH/80% CO$_2$.

Peak 1 RT 11.23 min, >99.0% enantiomeric excess

Peak 2 RT 15.64 min, >99.0%/o enantiomeric excess

1'-(3-Methoxy-4-(1H-pyrazol-4-yl)phenyl)spiro[indoline-2,3'-pyrrolidin]-2'-one, enantiomer 1 (10 mg, 43% yield) was isolated as a beige solid. MS(ESI) m/z: 361.1 (M+H)$^+$. HPLC: Method A. RT=6.52 min, 98.0% purity; Method B, RT=8.32 min, 98.0% purity. $^1$H NMR (400 MHz, DMSO-d$_6$) δ 8.12 (br. s., 1H), 7.97 (br. s., 1H), 7.70-7.60 (m, 2H), 7.21 (dd, J=8.6, 2.0 Hz, 1H), 7.01 (d, J=7.3 Hz, 1H), 6.96 (t, J=7.6 Hz, 1H), 6.57 (t, J=7.3 Hz, 1H), 6.49 (d, J=7.7 Hz, 1H), 6.33 (s, 1H), 3.96-3.79 (m, 5H), 3.25 (d, J=16.1 Hz 1H), 3.14-3.04 (m, 1H), 2.38-2.16 (m, 2H)

Example 34

1'-(4-(1H-Pyrazol-4-yl)phenyl)-3H-spiro[benzofuran-2,3'-pyrrolidin]-2'-one, Enantiomer

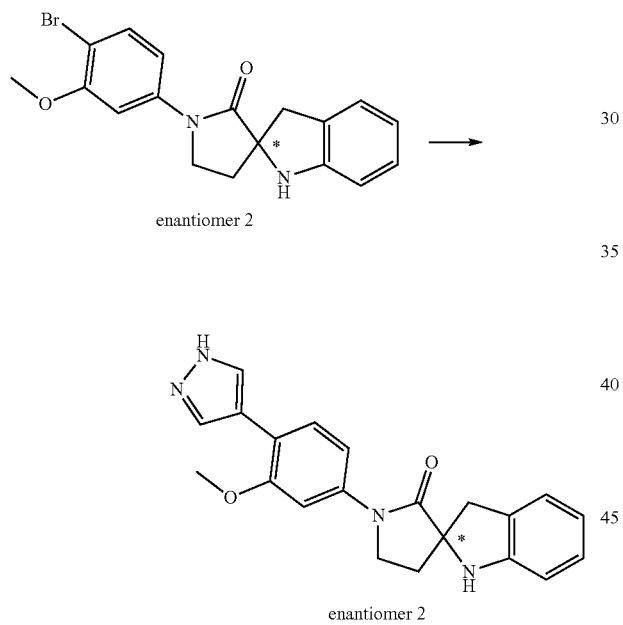

enantiomer 2

Prepared analogous to EXAMPLE 1 where tert-butyl 1'-(4-bromophenyl)-2'-oxospiro[indoline-2,3'-pyrrolidine]-1-carboxylate, EXAMPLE 1G enantiomer 1 was replaced by 1'-(4-bromophenyl)-3H-spiro[benzofuran-2,3'-pyrrolidin]-2'-one, enantiomer 2. 1'-(3-methoxy-4-(1H-pyrazol-4-yl)phenyl)spiro[indoline-2,3'-pyrrolidin]-2'-one (10 mg, 43% yield) was isolated as a beige solid. MS(ESI) m/z: 361.1 (M+H)$^+$. HPLC: Method A, RT=6.55 min, 97.3% purity; Method B, RT=8.32 min, 97.6% purity. $^1$H NMR (400 MHz, DMSO-d$_6$) δ 8.19-7.90 (m, 2H), 7.72-7.61 (m, 2H), 7.21 (dd, J=8.6, 2.0 Hz, 1H), 7.01 (d, J=7.3 Hz, 1H), 6.96 (t, J=7.7 Hz, 1H), 6.57 (t, J=7.3 Hz, 1H), 6.49 (d, J=7.7 Hz, 1H), 6.33 (s, 1H), 3.96-3.78 (m, 5H), 3.28-3.04 (m, 2H), 2.37-2.16 (m, 2H).

Example 35

1'-(3-Methoxy-4-(1H-pyrazol-4-yl)phenyl)-1,3-dihydrospiro[indene-2,3'-pyrrolidin]-2'-one

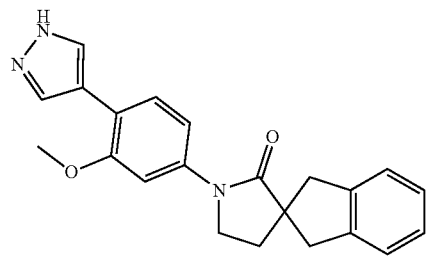 [SMILES: COc1cc(N2CCC3(Cc4ccccc4C3)C2=O)ccc1-c1cn[nH]c1]

Prepared using a procedure analogous to EXAMPLE 1 except that in EXAMPLE 1A, indoline-2-carboxylic acid was replaced by 2,3-dihydro-1H-indene-2-carboxylic acid and in EXAMPLE 1E, 4-bromoaniline was replaced by 4-bromo-3-methoxyaniline to give 1'-(3-methoxy-4-(1H-pyrazol-4-yl)phenyl)-1,3-dihydrospiro[indene-2,3'-pyrrolidin]-2'-one (7.2 mg, 37% yield). MS(ESI) m/z: 360.0 (M+H)$^+$. HPLC: Method C, RT 1.63 min. $^1$H NMR (500 MHz. DMSO-d$_6$) δ 8.19-7.84 (m, 2H), 7.69-7.57 (m, 2H), 7.23 (d, J=3.5 Hz, 2H), 7.17 (d, J=3.9 Hz, 3H), 3.94-3.79 (m 5H), 3.25 (d, J=15.8 Hz, 2H), 2.99 (d, J=15.9 Hz, 2H), 2.12 (t, J=6.6 Hz, 2H)

Example 36

1'-(4-1H-Pyrazol-4-yl)phenyl)-6-hydroxyspiro[indoline-2,3'-pyrrolidin]-2'-one

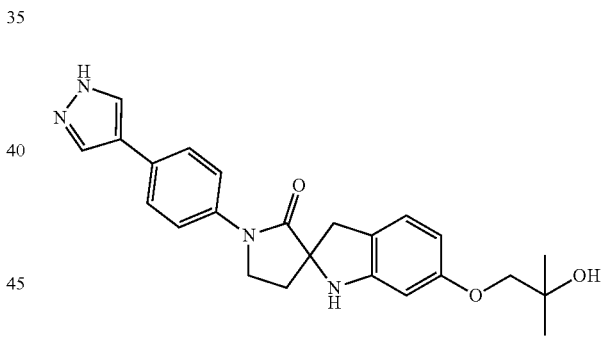

Example 37

1'-(4-(H-Pyrazol-4-yl)phenyl)-6-(2-hydroxy-2-methylpropoxy)spiro[indoline-2,3'-pyrrolidin]-2'-one

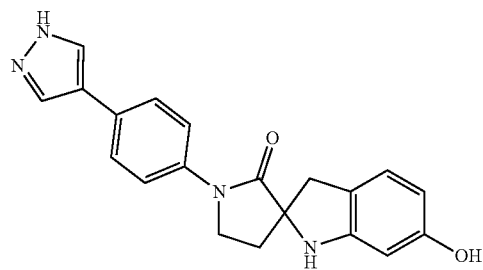 [SMILES: O=C1N(c2ccc(-c3cn[nH]c3)cc2)CCC12Cc1ccc(O)cc1N2]

Example 36A. 1'-(4-Bromophenyl)-6-hydroxyspiro[indoline-2,3'-pyrrolidin]-2'-one

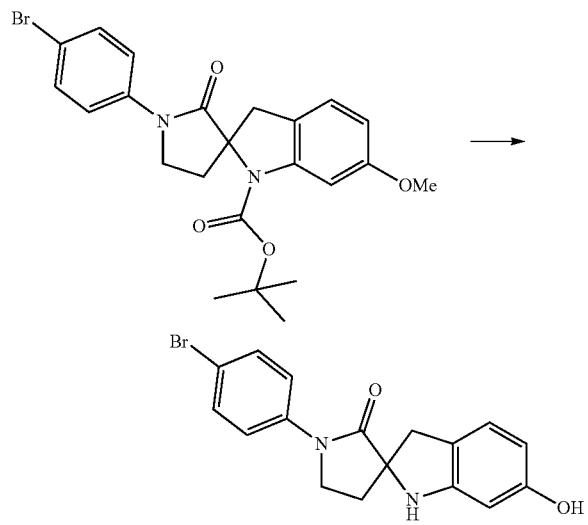

To a solution of tert-butyl 1'-(4-bromophenyl)-6-methoxy-2'-oxospiro[indoline-2,3'-pyrrolidine]-1-carboxylate, 2E (1.08 g, 2.282 mmol) in anhydrous $CH_2Cl_2$ was added $BBr_3$ 1M in heptane (6.84 ml, 6.84 mmol) dropwise at 0° C. The resulting solution was slowly warmed to rt and stirred at rt o.n. The reaction was cooled in ice bath, and quenched with sat $NaHCO_3$. Extracted EtOAc (3×). The combined organic layers were washed with brine, dried $MgSO_4$ and concentrated to give 1'-(4-bromophenyl)-6-hydroxyspiro[indoline-2,3'-pyrrolidin]-2'-one (0.82 g, 100% yield) as an off white solid. MS(ESI) m/z: 360.9 (M+H)$^+$.

Example 36B. Tert-butyl 1'-(4-bromophenyl)-6-hydroxy-2'-oxospiro[indoline-2,3'-pyrrolidine]-1-carboxylate

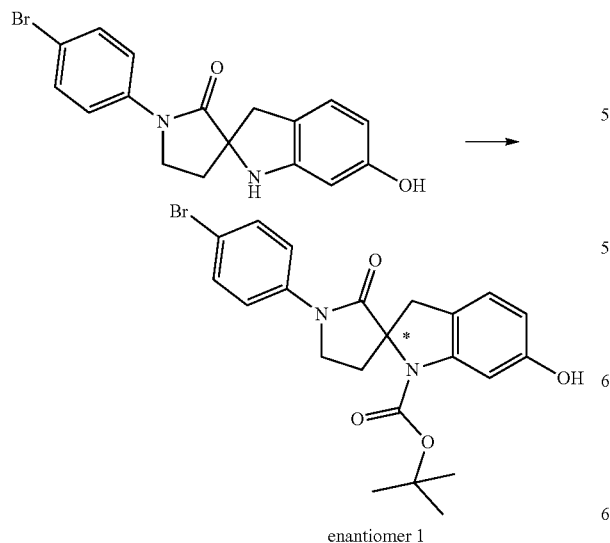

enantiomer 1

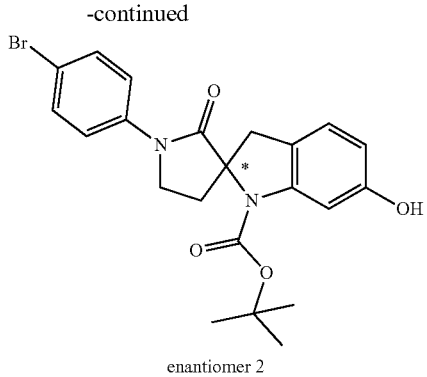

enantiomer 2

To a solution of 1'-(4-bromophenyl)-6-hydroxyspiro[indoline-2,3'-pyrrolidin]-2'-one (1.13 g, 3.15 mmol) in $CH_2Cl_2$ (20 mL) was added $Et_3N$ (0.66 mL, 4.72 mmol), DMAP (0.038 g, 0.315 mmol) and BOC-anhydride (0.876 mL, 3.77 mmol). After 1 h, water was added to the reaction mixture and extracted with AcOEt, the organic layer was washed with 1 M HCl, saturated aqueous $NaHCO_3$ and brine, concentrated then purified by normal phase chromatography give tert-butyl 1'-(4-bromophenyl)-6-hydroxy-2'-oxospiro[indoline-2,3'-pyrrolidine]-1-carboxylate (530 mg, 37% yield) as a white solid. $^1$H NMR (500 MHz, $CDCl_3$) δ 7.65-7.57 (m, 2H), 7.50 (d, J=9.1 Hz, 2H), 7.02 (d, J=8.0 Hz, 1H), 6.55 (dd, J=8.0, 2.2 Hz, 1H), 6.50 (d, J=2.2 Hz, 1H), 3.81-3.75 (m, 2H), 3.40 (dd. J=15.5, 1.0 Hz, 1H), 3.07 (d, J=15.7 Hz, 1H), 2.43 (dt, J=12.7, 4.8 Hz, 1H), 2.24 (dt, J=12.9, 8.4 Hz, 1H), 1.55 (s, 9H).

Chiral separation was accomplished using the conditions below:

Analytical chiral chromatographic conditions: Chiralpak IB, 4.6×250 mm, 5 micron.

Mobile phase: 35% MeOH/65% $CO_2$. Flow: 2.0 mL/min, 150 Bar, 40° C.

Enantiomer 1 RT 7.26 min.

Enantiomer 2 RT 8.71 min Preparative chiral chromatographic conditions: Chiralpak IB, 21×250 mm, 5 micron.

Mobile phase: 35% MeOH/65% $C_{o2}$. Flow: 45 mL/min, 100 Bar, 40° C.

Example 36C. Tert-butyl 1'-(4-bromophenyl)-6-(2-hydroxy-2-methylpropoxy)-2'-oxospiro[indoline-2,3'-pyrrolidine]-1-carboxylate

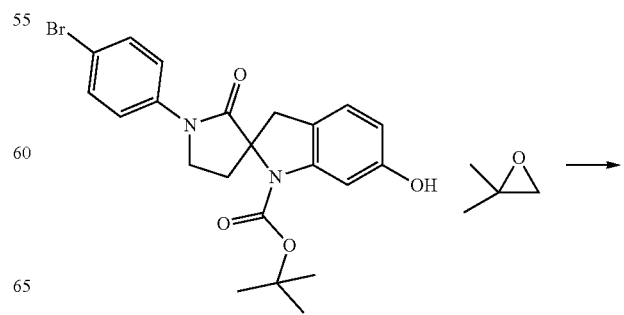

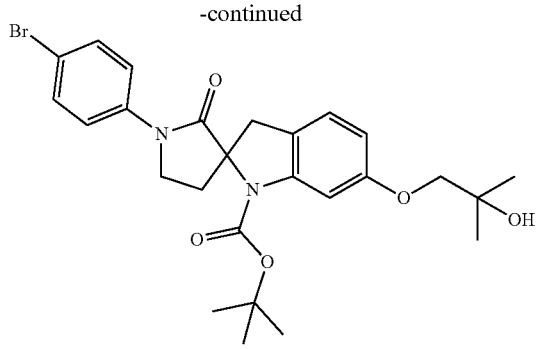

To a solution of tert-butyl 1'-(4-bromophenyl)-6-hydroxy-2'-oxospiro[indoline-2,3'-pyrrolidine]-1-carboxylate (50 mg, 0.109 mmol) in acetonitrile (2 mL) and water (0.13 mL) was added K$_2$CO$_3$ (60.2 mg, 0.435 mmol) and 2,2-dimethyloxirane (0.147 mL, 1.633 mmol) at rt. The reaction was microwaved at 120° C. for 30 min. MS(ESI) m/z: 373/375.0 (M+H-tBu)$^+$. The reaction mixture was diluted with EtOAc, acidified with 1.0 N HCl, washed with water and brine. The organic phase was dried over MgSO$_4$, filtered and concentrated to give crude mixture containing tert-butyl 1'-(4-bromophenyl)-6-(2-hydroxy-2-methylpropoxy)-2'-oxospiro[indoline-2,3'-pyrrolidine]-1-carboxylate and tert-butyl 1'-(4-bromophenyl)-6-hydroxy-2'-oxospiro[indoline-2,3'-pyrrolidine]-1-carboxylate which was used as is in the next step without further purification.

Example 36

1'-(4-(1H-Pyrazol-4-yl)phenyl)-6-(2-hydroxy-2-methylpropoxy)spiro[indoline-2,3'-pyrrolidin]-2'-one and EXAMPLE 37 1'-(4-(1H-pyrazol-4-yl)phenyl)-6-hydroxyspiro[indoline-2,3'-pyrrolidin]-2'-one

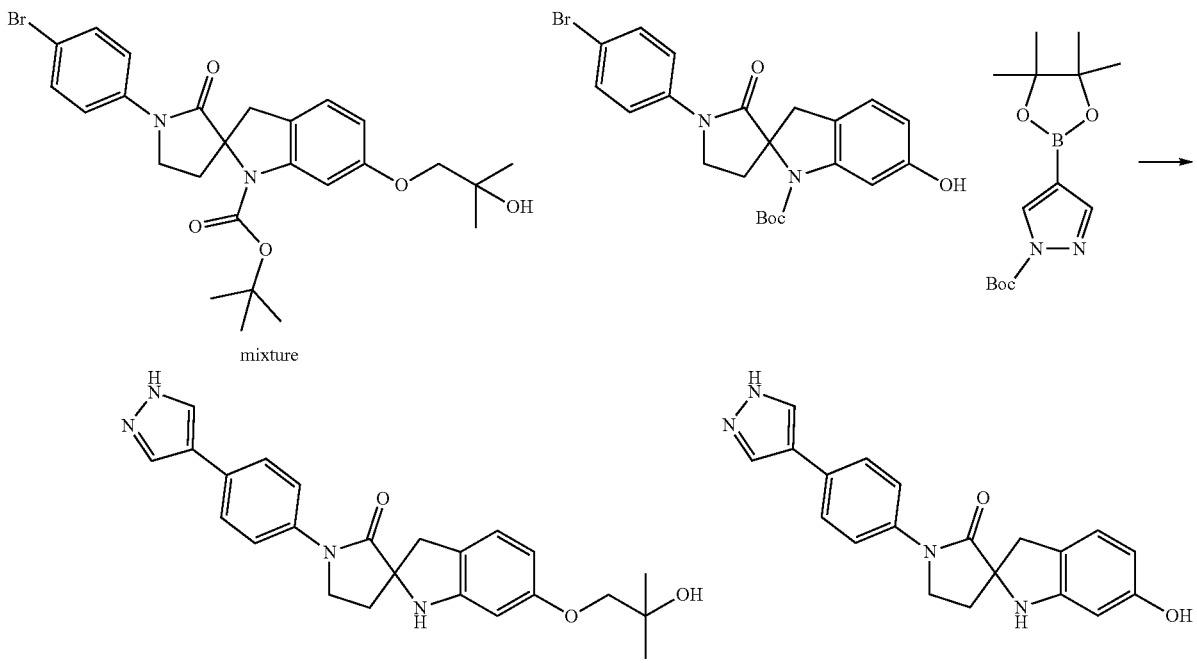

Prepared using a procedure analogous to EXAMPLE 1 except that tert-butyl 1'-(4-bromophenyl)-2'-oxospiro[indoline-2,3'-pyrrolidine]-1-carboxylate, 1F was replaced by the crude mixture containing tert-butyl 1'-(4-bromophenyl)-6-(2-hydroxy-2-methylpropoxy)-2'-oxospiro[indoline-2,3'-pyrrolidine]-1-carboxylate and tert-butyl 1'-(4-bromophenyl)-6-hydroxy-2'-oxospiro[indoline-2,3'-pyrrolidine]-1-carboxylate to give EXAMPLE 36, 1'-(4-(1H-pyrazol-4-yl)phenyl)-6-(2-hydroxy-2-methylpropoxy)spiro[indoline-2,3'-pyrrolidin]-2'-one (0.4 mg, 1%). MS(ESI) m % z: 419.1 (M+H)$^+$. HPLC: Method C, RT 1.28 min. $^1$H NMR (500 MHz, DMSO-d$_6$) δ 8.12 (br. s., 2H), 7.77-7.67 (m, 2H), 7.63 (d, J=8.5 Hz, 2H), 6.85 (d, J=7.9 Hz, 1H), 6.29 (s, 1H), 6.17-6.04 (m, 2H), 3.89-3.67 (m, 2H), 3.60 (s, 2H), 3.16-2.94 (m, 2H), 2.33-2.14 (m, 2H), 1.18 (s, 6H)

EXAMPLE 37, 1'-(4-(1H-pyrazol-4-yl)phenyl)-6-hydroxyspiro[indoline-2,3'-pyrrolidin]-2'-one, (12.2 mg, 23%). MS(ESI) m/z: 346.8 (M+H)$^+$. HPLC: Method C, RT 0.97 min. $^1$H NMR (500 MHz, DMSO-d$_6$) δ 8.03 (br. s., 2H), 7.73-7.66 (m, 2H), 7.65-7.59 (m, 2H), 6.74 (d, J=7.6 Hz, 1H), 6.02-5.91 (m 2H), 3.90-3.70 (m, 2H), 3.13-2.83 (m 2H), 2.27-2.09 (m, 2H)

Example 38

1'-(4-(1H-Pyrazol-4-yl)phenyl)-4-fluoro-6-methoxyspiro[indoline-2,3'-pyrrolidin]-2'-one, racemic

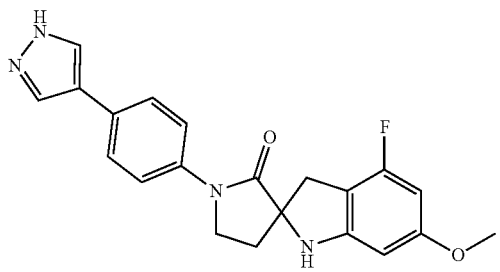 [SMILES: COc1cc(F)c2c(c1)NC1(CCN(c3ccc(-c4cn[nH]c4)cc3)C1=O)C2]

Example 38A. (Z)-Methyl 2-azido-3-(2-fluoro-4-methoxyphenyl)acrylate

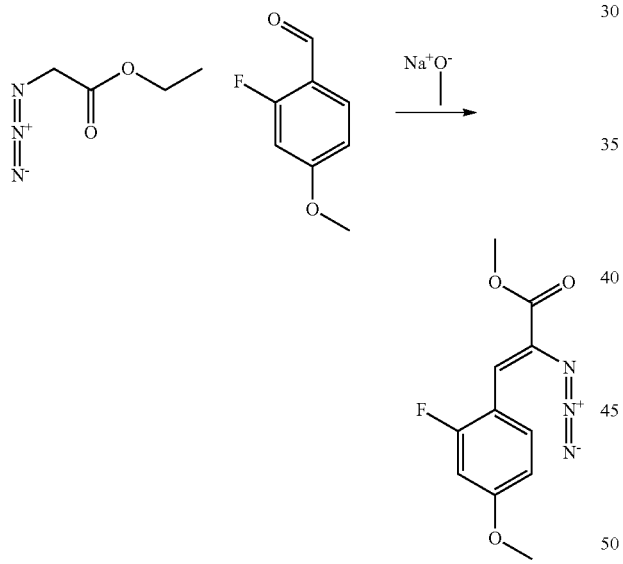

A solution of sodium methoxide 25% in MeOH (11.87 mL, 51.9 mmol) in MeOH (20 mL) was cooled to −10° C. To this solution was added dropwise a solution of 2-fluoro-4-methoxybenzaldehyde (2.0 g, 13.0 mmol) and ethyl azidoacetate (6.70 g, 51.9 mmol) in MeOH (5 ml) through addition funnel over 0.5 h. The reaction which became thick yellow was stirred at −10° C. for an additional 1.5 h. Water was added and the mixture was extracted with ether (3×). The combined organic layers were washed with water, concentrated then purified by normal phase chromatography to give (Z)-methyl 2-azido-3-(2-fluoro-4-methoxyphenyl) acrylate (1.96 g, 60% yield) as a pale yellow solid. MS(ESI) m z: 224.0 (M+H—$N_2$)$^+$. $^1$H NMR (400 MHz, CDCl$_3$) δ 8.28 (t, J=8.8 Hz, 1H), 7.12 (s, 1H), 6.73 (dd. J=8.9, 2.5 Hz, 1H), 6.62 (dd, J=12.4, 2.5 Hz, 1H), 3.90 (s, 3H), 3.83 (s, 3H)

Example 38B. Methyl 4-fluoro-6-methoxy-1H-indole-2-carboxylate

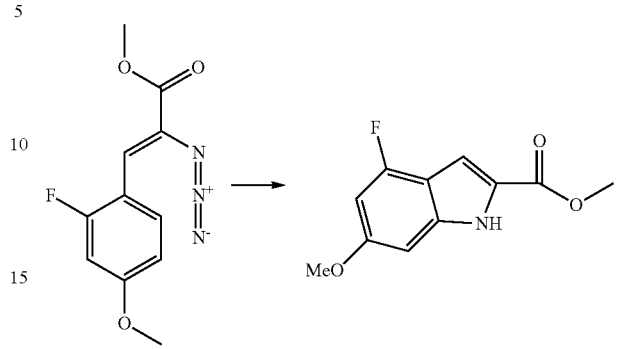

A solution of (Z)-methyl 2-azido-3-(2-fluoro-4-methoxyphenyl)acrylate (800 mg, 3.18 mmol) in xylene (10 ml) was added dropwise to refluxing xylene (10 ml) at 138° C. under $N_2$ then stirred at 138° C. for 1 h. The solvent was evaporated off and the residue was used without further purification to give methyl 4-fluoro-6-methoxy-1H-indole-2-carboxylate (0.57 g, 80% yield) as a yellow solid. MS(ESI) m/z: 224, 1 (M+H)$^+$. $^1$H NMR (400 MHz, CDCl$_3$) δ 7.21 (dd, J=2.2, 0.9 Hz, 1H), 6.63 (dd, J=2.0, 0.9 Hz, 1H), 6.52 (dd, J=11.6, 1.9 Hz, 1H), 3.93 (s, 3H), 3.84 (s, 3H)

Example 38C. 1-Tert-butyl 2-methyl 4-fluoro-6-methoxy-1H-indole-1,2-dicarboxylate

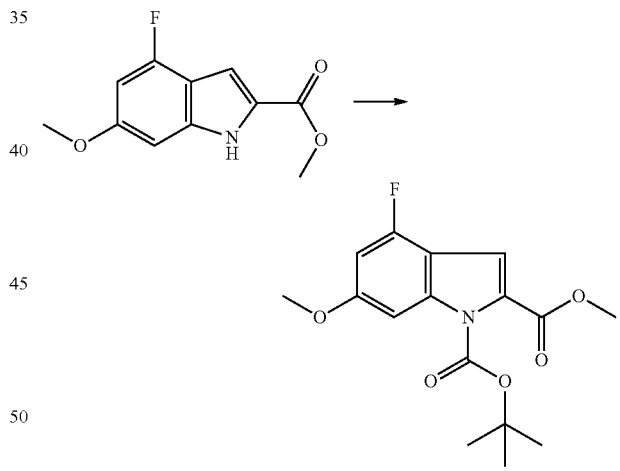

To a solution of methyl 4-fluoro-6-methoxy-H-indole-2-carboxylate (0.57 g, 2.55 mmol) in EtOAc (10 mL) at 0° C. was added Et$_3$N (0.534 mL, 3.83 mmol), DMAP (0.031 g, 0.255 mmol) and BOC-anhydride (0.71 mL, 3.06 mmol). The mixture was stirred at rt o.n. Water was added to the reaction mixture and extracted with EtOAc. The organic layer was washed with 1 M HCl, saturated aqueous NaHCO$_3$ and brine, dried over MgSO$_4$, concentrated and purified by normal phase chromatography to give 1-tert-butyl 2-methyl 4-fluoro-6-methoxy-1H-indole-1,2-dicarboxylate (762 mg, 92% yield). MS(ESI) m/z: 224.0 (M+H-Boc)$^+$. $^1$H NMR (400 MHz, CDCl$_3$) δ 7.43 (d, J=1.8 Hz, 1H), 7.14 (d, J=0.7 Hz, 1H), 6.60 (dd, J=11.0, 2.0 Hz, 1H), 3.90 (s, 3H), 3.88 (s, 3H)

Example 38D. 1-Tert-butyl 2-methyl 4-fluoro-6-methoxyindoline-1,2-dicarboxylate

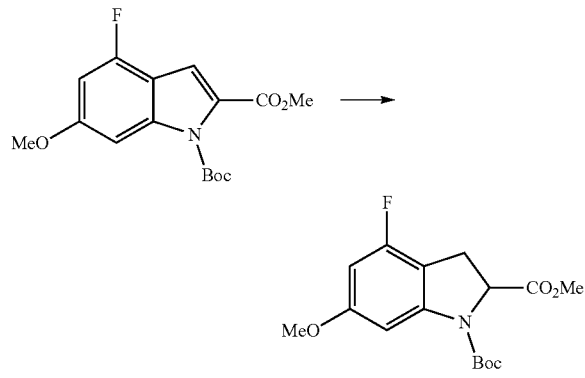

1-Tert-butyl 2-methyl 4-fluoro-6-methoxy-1H-indole-1,2-dicarboxylate (760 mg, 2.351 mmol) was dissolved in ethanol (100 mL) in a hydrogenation flask, then 10 Pd—C (100 mg, 0.940 mmol) was added. The mixture was hydrogenated at 55 psi $H_2$ o.n. The mixture was filtered through Celite and concentrated to give 1-tert-butyl 2-methyl 4-fluoro-6-methoxyindoline-1,2-dicarboxylate (0.71 g, 93% yield) as a clear, colorless oil that solidified upon standing. MS(ESI) m/z: 326.1 (M+H)$^+$.

Example 38

1'-(4-(1H-Pyrazol-4-yl)phenyl)-4-fluoro-6-methoxyspiro[indoline-2,3'-pyrrolidin]-2'-one, Racemic

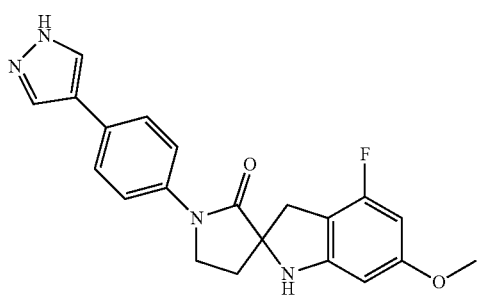 [SMILES: COc1cc(F)c2c(c1)NC1(CCN(c3ccc(-c4cn[nH]c4)cc3)C1=O)C2]

Prepared using a procedure analogous to EXAMPLE 4 except that 1-tert-butyl 2-methyl 6-methoxyindoline-1,2-dicarboxylate was replaced by 1-tert-butyl 2-methyl 4-fluoro-6-methoxyindoline-1,2-dicarboxylate and in EXAMPLE 4E NaBH$_3$CN and MeOH was used in the reductive amination to give 1'-(4-(1H-pyrazol-4-yl)phenyl)-4-fluoro-6-methoxyspiro[indoline-2,3'-pyrrolidin]-2'-one (3.9 mg, 25% yield). MS(ESI) m/z: 379.0 (M+H)$^+$. HPLC: Method C, RT 1.44 min. $^1$H NMR (500 MHz, DMSO-d$_6$) δ 8.17 (br. s., 1H), 7.94 (br. s., 1H), 7.74-7.59 (m, 5H), 6.71 (s, 1H), 5.96 (d, J=10.9 Hz, 1H), 5.91 (s, 1H), 3.88-3.76 (m, 2H), 3.68-3.68 (m, 1H), 3.67 (s, 3H), 3.19-3.02 (m, 2H), 2.36-2.14 (m, 2H)

Example 39

1'-(4-(1H-Pyrazol-4-yl)phenyl)-4-fluoro-6-methoxyspiro[indoline-2,3'-pyrrolidin]-2'-one, Enantiomer 1

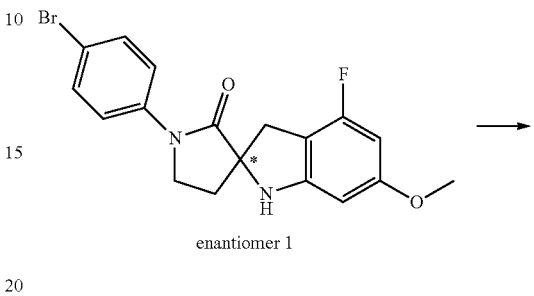

enantiomer 1

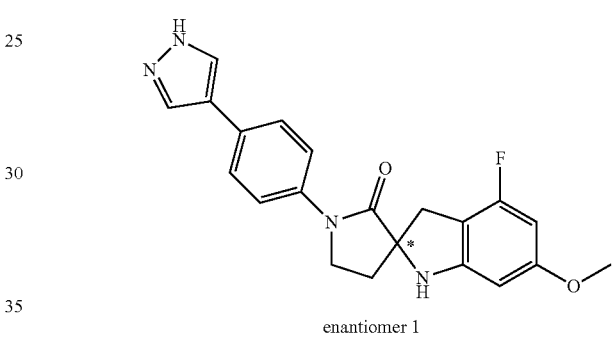

enantiomer 1

Prepared analogous to EXAMPLE 1 where tert-butyl 1'-(4-bromophenyl)-2'-oxospiro[indoline-2,3'-pyrrolidine]-1-carboxylate, EXAMPLE 1F was replaced by tert-butyl 1'-(4-bromophenyl)-4-fluoro-6-methoxy-2'-oxospiro[indoline-2,3'-pyrrolidine]-1-carboxylate, enantiomer 1. Chiral separation of tert-butyl 1'-(4-bromophenyl)-4-fluoro-6-methoxy-2'-oxospiro[indoline-2,3'-pyrrolidine]-1-carboxylate was accomplished using the conditions below:

Analytical chiral chromatographic condition: Chiralpak AD-H, 4.6×250 mm, 5 micron. Mobile phase: 35% IPA/65% CO$_2$. Flow: 2.0 mL/min, 150 Bar, 40° C.

Preparative chiral chromatographic condition: Chiralpak AD-H, 21×250 mm, 5 micron. Mobile phase: 20% MeOH/80% CO$_2$. Flow: 45 mL/min, 100 Bar, 40° C.

Enantiomer 1 RT 2.98, >99.0% enantiomeric excess

Enantiomer 2 RT 4.34, >99.0% enantiomeric excess

1'-(4-(1H-Pyrazol-4-yl)phenyl)-4-fluoro-6-methoxyspiro[indoline-2,3'-pyrrolidin]-2'-one, enantiomer 1 (19 mg, 60% yield) as an off white solid. MS(ESI) m/z: 379.1 (M+H)$^+$. HPLC: Method A, RT=7.21 min, 96.6% purity; Method B, RT=8.86 min, 98.9%6 purity. $^1$H NMR (400 MHz, DMSO-d$_6$) δ 8.06 (br. s., 2H), 7.81-7.69 (m, 2H), 7.69-7.61 (m, 2H), 6.71 (br. s., 1H), 6.04-5.86 (m, 2H), 3.93-3.78 (m, 2H), 3.69 (s, 3H), 3.22-2.97 (m, 2H), 2.42-2.12 (m, 2H)

Example 40

1'-(4-(1H-Pyrazol-4-yl)phenyl)-4-fluoro-6-methoxyspiro[indoline-2,3'-pyrrolidin]-2'-one, Enantiomer 2

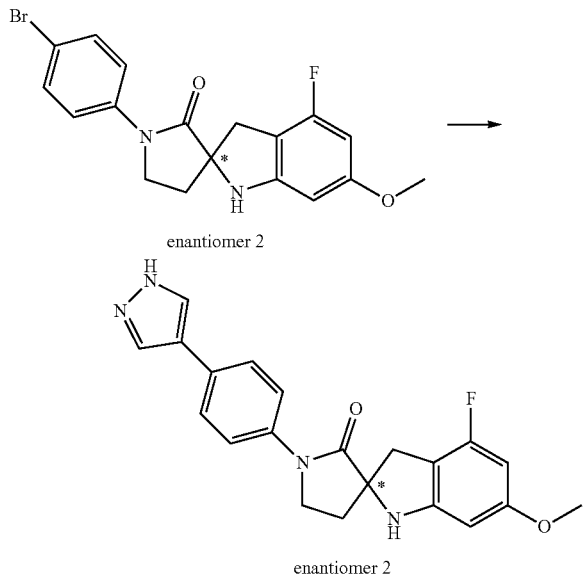

enantiomer 2

↓ enantiomer 2

Prepared analogous to EXAMPLE 1 where tert-butyl 1'-(4-bromophenyl)-2'-oxospiro[indoline-2,3'-pyrrolidine]-1-carboxylate, EXAMPLE 1F was replaced by tert-butyl 1'-(4-bromophenyl)-4-fluoro-6-methoxy-2'-oxospiro[indoline-2,3'-pyrrolidine]-1-carboxylate, enantiomer 2.

1'-(4-(1H-Pyrazol-4-yl)phenyl)-4-fluoro-6-methoxyspiro[indoline-2,3'-pyrrolidin]-2'-one, Enantiomer 2 (22 mg, 71% yield) was isolated as an off-white solid. MS(ESI) m/z: 379.1 (M+H)+. HPLC: Method A, RT=7.20 min, 98.5% purity; Method B. RT=8.85 min, 99.6% purity. $^1$H NMR (400 MHz, DMSO-$d_6$) δ 8.05 (br. s., 2H), 7.79-7.56 (m, 4H), 6.71 (br. s., 1H), 6.05-5.85 (m, 2H), 3.94-3.76 (m, 2H), 3.69 (s, 3H), 3.21-3.01 (m, 2H), 2.38-2.14 (m, 2H)

Example 41

1'-(5-(1H-Pyrazol-4-yl)pyridin-2-yl)spiro[indoline-2,3'-pyrrolidin]-2'-one

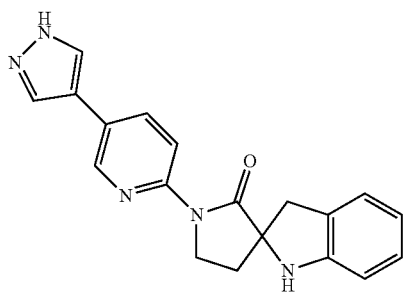 [SMILES: O=C1N(c2ccc(-c3cn[nH]c3)cn2)CCC12Cc1ccccc1N2]

Prepared using a procedure analogous to EXAMPLE 1 except that in the synthesis of 1-tert-butyl 2-methyl 2-(2-((4-bromophenyl)amino)ethyl)indoline-1,2-dicarboxylate, EXAMPLE 1E, 4-bromoaniline was replaced by 5-bromopyridin-2-amine to give (6 mg, 50% yield). MS(ESI) m/z: 332.2 (M+H)+. HPLC: Method C, RT 1.16 min. $^1$H NMR (500 MHz. DMSO-$d_6$) δ 8.71 (s, 1H), 8.41-8.15 (m, 2H), 8.11-7.91 (m, 2H), 7.11-6.87 (m, 2H), 6.66-6.41 (m, 2H), 6.33 (s, 1H), 4.13-3.98 (m, 1H), 3.91 (dt, J=10.9, 7.0 Hz, 1H), 3.28-3.18 (m, 1H), 3.09 (d, J=16.2 Hz, 1H), 2.33-2.09 (m, 2H)

Example 42

1'-(4-(1H-Pyrazol-4-yl)phenyl)-6-(cyclopropylmethoxy)spiro[indoline-2,3'-pyrrolidin]-2'-one, Enantiomer 1

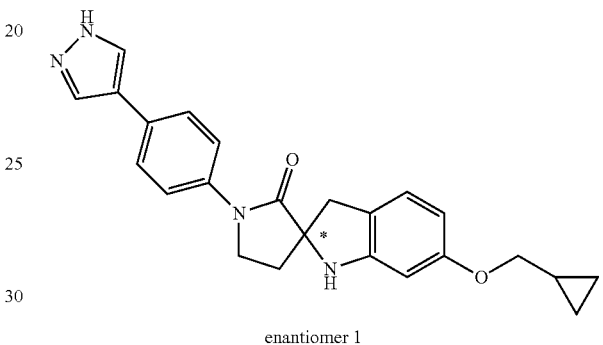

enantiomer 1

Example 42A. Tert-butyl 1'-(4-bromophenyl)-6-(cyclopropylmethoxy)-2'-oxospiro[indoline-2,3'-pyrrolidine]-1-carboxylate, Enantiomer 1

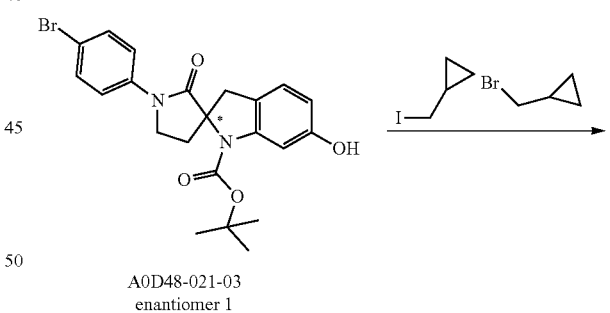

A0D48-021-03
enantiomer 1

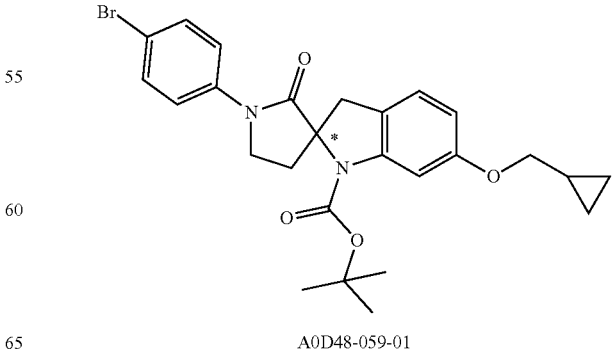

A0D48-059-01

To a solution of tert-butyl 1'-(4-bromophenyl)-6-hydroxy-2'-oxospiro[indoline-2,3'-pyrrolidine]-1-carboxylate, EXAMPLE 36B enantiomer 1, (30 mg, 0.065 mmol) in DMF (1 mL) was added potassium carbonate (36.1 mg, 0.261 mmol) followed by (iodomethyl)cyclopropane (35 µl, 0.196 mmol). After overnight stirring, mainly staring material was observed. NaH (5.2 mg, 0.13 mmol) and (bromomethyl)cyclopropane (20 µl, 0.206 mmol) was added, The reaction was stirred at rt for 5 h, then it was concentrated and purified by normal phase chromatography to give tert-butyl 1'-(4-bromophenyl)-6-(cyclopropylmethoxy)-2'-oxospiro[indoline-2,3'-pyrrolidine]-1-carboxylate, enantiomer 1 (17 mg, 51% yield) as a clear glass. MS(ESI) m/z=: 412.9/414.9 (M+H-Boc)$^+$.

Example 42. 1'-(4-(1H-Pyrazol-4-yl)phenyl)-6-(cyclopropylmethoxy)spiro[indoline-2,3'-pyrrolidin]-2'-one, Enantiomer 1

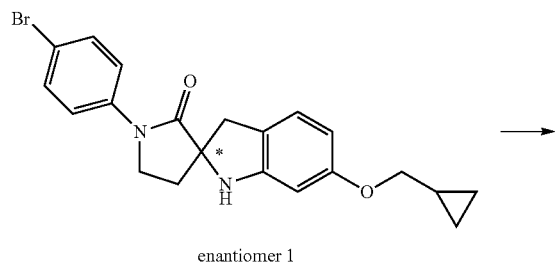

enantiomer 1

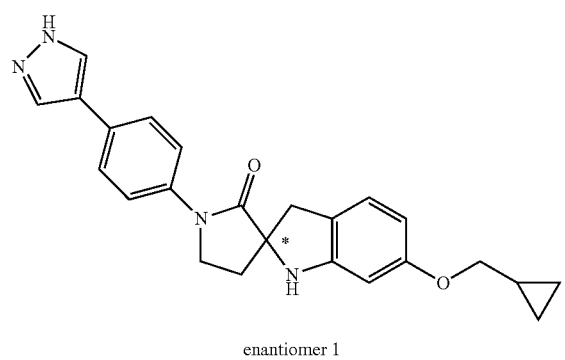

enantiomer 1

Prepared using a procedure analogous to EXAMPLE 4 except that tert-butyl 1'-(4-bromophenyl)-6-methoxy-2'-oxospiro[indoline-2,3'-pyrrolidine]-1-carboxylate, EXAMPLE 4F was replaced by tert-butyl 1'-(4-bromophenyl)-6-(cyclopropylmethoxy)-2'-oxospiro[indoline-2,3'-pyrrolidine]-1-carboxylate, enantiomer 1 to give 1'-(4-(1H-pyrazol-4-yl)phenyl)-6-(cyclopropylmethoxy)spiro[indoline-2,3'-pyrrolidin]-2'-one, enantiomer 1 (4.2 mg, 30% yield). MS(ESI) m/z: 401.1 (M+H)$^+$. HPLC: Method C, RT 1.59 min. $^1$H NMR (500 MHz, DMSO-$d_6$) δ 8.17 (br. s., 1H), 7.92 (br. s., 1H), 7.76-7.68 (m, 2H), 7.63 (d, J=8.2 Hz, 2H), 6.84 (d, J=7.6 Hz, 1H), 6.29 (s, 1H), 6.14-5.99 (m, 2H), 3.97-3.74 (m, 2H), 3.71 (d, J=6.7 Hz, 2H), 3.19-2.88 (m, 2H), 2.33-2.10 (m, 2H), 1.18 (br. s., 1H), 0.55 (d, J=7.3 Hz, 2H), 0.29 (d, J=4.6 Hz, 2H)

Example 43

1'-(4-(1H-Pyrazol-4-yl)phenyl)-6-(cyclopropylmethoxy)spiro[indoline-2,3'-pyrrolidin]-2'-one, Enantiomer 2

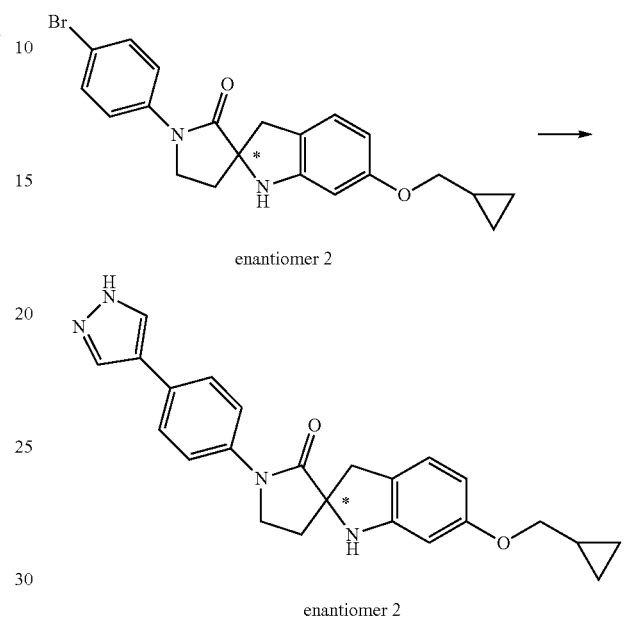

enantiomer 2 enantiomer 2

Prepared using a procedure analogous to EXAMPLE 42 except that tert-butyl 1'-(4-bromophenyl)-6-(cyclopropylmethoxy)-2'-oxospiro[indoline-2,3'-pyrrolidine]-1-carboxylate, enantiomer 1 was replaced by tert-butyl 1'-(4-bromophenyl)-6-(cyclopropylmethoxy)-2'-oxospiro[indoline-2,3'-pyrrolidine]-1-carboxylate, enantiomer 2 to give 1'-(4-(1H-pyrazol-4-yl)phenyl)-6-(cyclopropylmethoxy)spiro[indoline-2,3'-pyrrolidin]-2'-one, Enantiomer 2 (5.1 mg, 31% yield). MS(ESI) m/z: 401.1 (M+H)$^+$. HPLC: Method C, RT 1.59 min. $^1$H NMR (500 MHz, DMSO-$d_6$) δ 8.17 (br. s., 1H), 7.92 (br. s., 1H), 7.77-7.54 (m, 4H), 6.84 (d, J=7.3 Hz, 1H), 6.29 (br. s., 1H), 6.16-5.97 (m, 2H), 3.92-3.75 (m, 2H), 3.71 (d, J=6.7 Hz, 2H), 3.18-2.88 (m, 2H), 2.32-2.08 (m, 2H), 1.18 (br. s., 1H), 0.55 (d, J=7.3 Hz, 2H), 0.30 (br. s., 2H)

Example 44

1'-(5-(1H-Pyrazol-4-yl)pyrazin-2-yl)spiro[indoline-2,3'-pyrrolidin]-2'-one

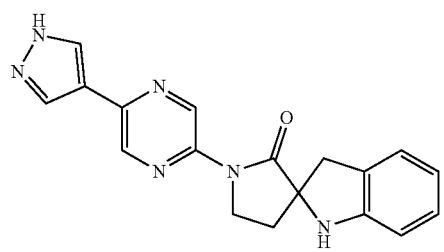 [SMILES: O=C1N(c2cnc(-c3cn[nH]c3)cn2)CCC12Cc1ccccc1N2]

Prepared using a procedure analogous to EXAMPLE 1 except that in the synthesis of 1-tert-butyl 2-methyl 2-(2-((4-bromophenyl)amino)ethyl)indoline-1,2-dicarboxylate, EXAMPLE 1E, 4-bromoaniline was replaced by 5-bromopyrazin-2-amine to give (9 mg, 43% yield). MS(ESI) m/z: 333.1 (M+H)$^+$. HPLC: Method C, RT 1.25 min. $^1$H NMR (500 MHz, DMSO-d$_6$) δ 9.49 (s, 1H), 8.85 (s, 1H), 8.41 (br. s., 1H), 8.12 (br. s., 1H), 7.11-6.89 (m, 2H), 6.68-6.44 (m, 2H), 6.37 (s, 1H), 4.03 (br. s., 1H), 3.94-3.77 (m, 1H), 3.30 (d, J=16.2 Hz, 1H), 3.12 (d, J=16.2 Hz, 1H), 2.37-2.13 (m, 2H)

Example 45

1'-(4-(Pyridin-4-yl)phenyl)spiro[indoline-2,3'-pyrrolidin]-2'-one

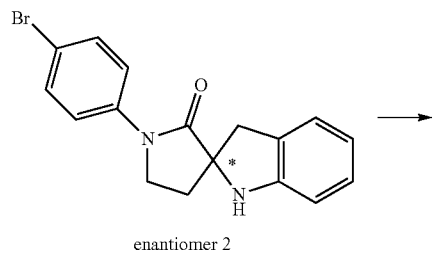

enantiomer 2

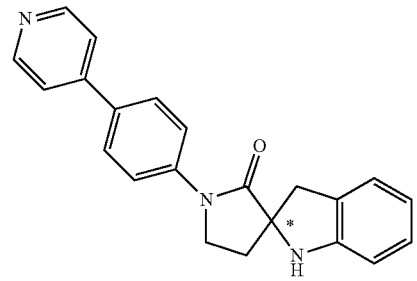

Prepared analogous to EXAMPLE 2 where tert-butyl 4-(4,4,5,5-tetramethyl-1,3,2-dioxaborolan-2-yl)-1H-pyrazole-1-carboxylate was replaced by pyridine-4-boronic acid pinacol ester to give 1'-(4-(pyridin-4-yl)phenyl)spiro[indoline-2,3'-pyrrolidin]-2'-one (8.2 mg, 69% yield). MS(ESI) m/z: 342.0 (M+H)$^3$. HPLC: Method C, RT 1.07 min. $^1$H NMR (500 MHz, DMSO-d$_6$) δ 8.59 (br. s., 2H), 7.87 (s, 4H), 7.73 (d, J=4.5 Hz, 2H), 7.04-6.87 (m, 2H), 6.61-6.42 (m, 2H), 6.26 (s, 1H), 3.86 (d, J=16.1 Hz, 1H), 3.31-2.98 (m, 3H), 2.35-2.14 (m, 2H)

Example 46

1'-(4-(Pyridin-4-yl)phenyl)-3H-spiro[benzofuran-2,3'-pyrrolidin]-2'-one

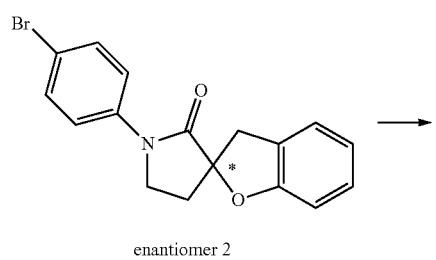

enantiomer 2

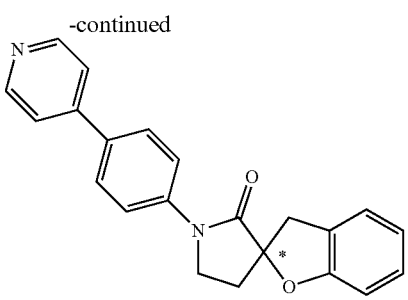

Prepared analogous to EXAMPLE 31 where tert-butyl 4-(4,4,5,5-tetramethyl-1,3,2-dioxaborolan-2-yl)-1H-pyrazole-1-carboxylate was replaced by pyridine-4-boronic acid pinacol ester to give 1'-(4-(pyridin-4-yl)phenyl)-3H-spiro[benzofuran-2,3'-pyrrolidin]-2'-one (7.2 mg, 72% yield). MS(ESI) m/z: 343.1 (M+H)$^+$. HPLC: Method C RT 1.26 min. $^1$H NMR (500 MHz. DMSO-d$_6$) δ 8.64 (br. s., 2H), 7.96-7.79 (m, 7H), 7.35-7.01 (m, 5H), 6.94-6.73 (m, 2H), 4.07-3.88 (m, 2H), 3.53-3.27 (m, 2H), 2.94-2.68 (m, 2H)

Example 47

1-(4-(1H-pyrazol-4-yl)phenyl)-3',4'-dihydro-1 $^1$H-spiro[pyrrolidine-3,2'-quinolin]-2-one

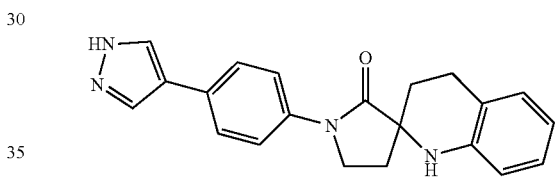

Prepared using a procedure analogous to EXAMPLE 1, by replacing 1B with 1-(tert-butyl) 2-methyl 3,4-dihydroquinoline-1,2(2H)-dicarboxylate. MS(ESI) m/z: 345.1 (M+H)$^+$. HPLC: Method A. RT=10.19 min, 99% purity; Method B, RT=8.57 min, 99% purity. $^1$H NMR (400 MHz, DMSO-d$_6$) δ 8.06 (br. s., 2H), 7.75-7.69 (m, 2H), 7.68-7.62 (m, 2H), 6.96-6.85 (m, 2H), 6.59-6.42 (m, 2H), 3.93-3.76 (m, 2H), 2.94-2.80 (m, 1H), 2.65 (dt, J=16.1, 5.8 Hz, 1H), 2.25-2.10 (m, 2H), 2.07-1.90 (m, 1H), 1.88-1.73 (m, 1H), 1.33-1.18 (m, 3H)

Example 48

1'-(4-(1H-pyrazol-4-yl)phenyl)-1,4-dihydro-2H-spiro[isoquinoline-3,3'-pyrrolidin]-2'-one

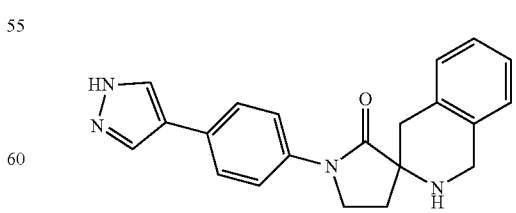

Prepared using a procedure analogous to EXAMPLE 1, by replacing 1B with 2-(tert-butyl) 3-methyl 3,4-dihydroisoquinoline-2,3(1H)-dicarboxylate. MS(ESI) m/z: 344.9 (M+H)$^+$. HPLC: Method C, RT 1.06 min. $^1$H NMR (500

MHz, DMSO-d$_6$) δ 7.75-7.60 (m, 4H), 7.25-7.11 (m, 4H), 4.25-4.04 (m, 2H), 3.99-3.84 (m, 2H), 3.02-2.90 (m, 2H), 2.29-2.16 (m, 1H), 2.08-1.97 (m, 1H)

Example 49

1'-(4-(1H-pyrrolo[2,3-b]pyridin-4-yl)phenyl)-1,4-dihydro-2H-spiro[isoquinoline-3,3'-pyrrolidin]-2'-one

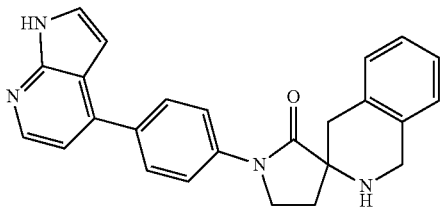 [SMILES: O=C1N(c2ccc(-c3ccnc4[nH]ccc34)cc2)CCC12Cc1ccccc1CN2]

Prepared using a procedure analogous to EXAMPLE 1, by replacing 1B with 2-(tert-butyl) 3-methyl 3,4-dihydroisoquinoline-2,3(1H)-dicarboxylate and by replacing tert-butyl 4-(4,4,5,5-tetramethyl-1,3,2-dioxaborolan-2-yl)-1H-pyrazole-1-carboxylate with 4-(4,4,5,5-tetramethyl-1,3,2-dioxaborolan-2-yl)-1H-pyrrolo[2,3-b]pyridine. MS(ESI) min: 395.2 (M+H)$^+$. HPLC: Method C, RT 0.87 min. $^1$H NMR (500 MHz, DMSO-d$_6$) 8.32 (d, J=4.9 Hz, 1H), 7.98-7.86 (m, 4H), 7.59 (br. s., 1H), 7.32 (d, J=3.7 Hz, 3H), 7.30-7.23 (m, 3H), 6.67 (br. s., 1H), 4.53-4.39 (m, 2H), 4.18-4.04 (m, 2H), 3.35-3.12 (m, 2H), 2.55 (s, 3H), 2.18 (dd, J=12.6, 5.9 Hz, 1H)

Example 50

1'-(4-(1H-pyrazol-4-yl)phenyl)spiro[chromane-2,3'-pyrrolidin]-2'-one

Prepared using a procedure analogous to EXAMPLE 1, by replacing 1B with methyl chromane-2-carboxylate. MS(ESI) m/z: 346.1 (M+H)$^+$. HPLC: Method A, RT=9.39 min. 96% purity; Method B, RT=7.88 min, 96% purity. $^1$H NMR (500 MHz, DMSO-d$_6$) δ 8.24-8.14 (m, 1H), 7.98-7.88 (m, 1H), 7.75-7.69 (m, 2H), 7.68-7.63 (m, 2H), 7.15-7.07 (m, 2H), 6.89-6.84 (m, 1H), 6.82-6.78 (m, 1H), 3.96-3.84 (m, 2H), 2.98-2.88 (m, 1H), 2.87-2.76 (m, 1H), 2.40-2.25 (m, 2H), 2.22-2.12 (m, 1H), 2.06-1.96 (m, 1H)

Example 51

1'-(4-(1H-pyrazol-4-yl)phenyl)-3,3-dimethylspiro[indoine-23'-pyrrolidin]-2-one

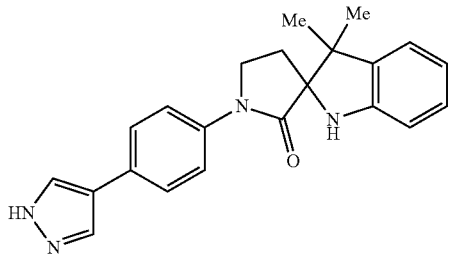 [SMILES: CC1(C)c2ccccc2NC12CCN(c1ccc(-c3cn[nH]c3)cc1)C2=O]

Example 51A. ethyl 3,3-dimethylindoline-2-carboxylate

Ethyl 3-methyl-2-oxobutanoate (6.67 g, 46.3 mmol) and phenylhydrazine (6 mL, 61.0 mmol) were mixed neat in a 40 mL vial and heated to 75° C. under a gentle stream of nitrogen to drive off water. After the deep orange solution goes from cloudy to clear with no visible water droplets, the reaction was cooled to rt. A thick solid formed. This solid mass was diluted with EtOH (40 mL) and 12 N HCl (11.57 mL, 139 mmol). Heated to 75° C. overnight. The reaction mixture was then transferred to a 1 L Erlenmeyer with 150 mL MeOH. NaBH$_4$ (4.97 g, 139 mmol) was added slowly so as to control vigorous bubbling. After addition of NaBH$_4$ the reaction was allowed to stir for 1 hour. The reaction was then quenched with water and extracted with EtOAc. The combined organic layers were concentrated and the residue was purified by flash column chromatography by eluting with a linear gradient of 0% to 40% EtOAc in hexanes. Ethyl 3,3-dimethylindoline-2-carboxylate (8.2 g, 74% yield) was thus isolated as a light yellow oil. MS(ESI) m/z: 220.1 (M+H)$^+$.

Example 51B. 1-(tert-butyl) 2-ethyl 3,3-dimethylindoline-1,2-dicarboxylate

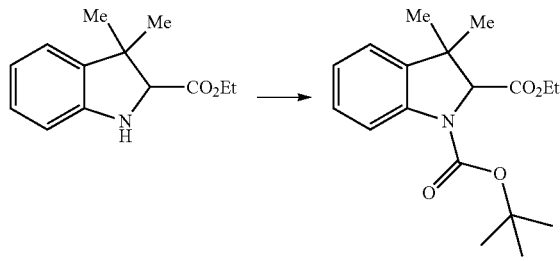 [SMILES: CCOC(=O)C1Nc2ccccc2C1(C)C ; CCOC(=O)C1N(C(=O)OC(C)(C)C)c2ccccc2C1(C)C]

Ethyl 3,3-dimethylindoline-2-carboxylate (1.75 g, 7.98 mmol) was dissolved in CH₂Cl₂, followed by addition of Boc₂O (1.85 ml, 7.98 mmol) and the reaction was stirred for 8 hours. The reaction was then concentrated and purified by flash column chromatography, eluting with a linear gradient of 0% to 25% EtOAc in hexanes. 1-tert-butyl 2-ethyl 3,3-dimethylindoline-1,2-dicarboxylate (2.4 g, 7.51 mmol, 94% yield) was isolated as an amber oil. MS(ESI) m/z: 264.0 (M-tBu+2H)⁺.

Example 51C. 1-(tert-butoxycarbonyl)-3,3-dimethylindoline-2-carboxylic Acid

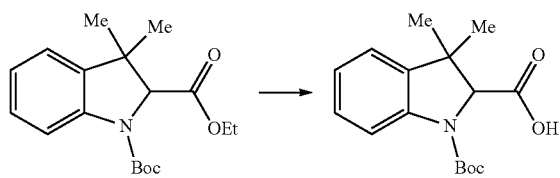 [SMILES: CCOC(=O)C1N(C(=O)OC(C)(C)C)c2ccccc2C1(C)C ; CC(C)(C)OC(=O)N1c2ccccc2C(C)(C)C1C(=O)O]

NaOH (0.5 g, 12.50 mmol) was dissolved in water (5 mL) and added to a solution of 1-tert-butyl 2-ethyl 6-methoxy-3,3-dimethylindoline-1,2-dicarboxylate (0.35 g, 1.00 mmol) in MeOH (15 mL). The reaction was heated to 80° C. for 1 hour, at which point it was concentrated to dryness. Ether (15 mL) and water (10 mL) was added and the reaction was neutralized with 1 N HCl. The layers were separated and the aqueous was further extracted with EtOAc. The organic layers were dried and concentrated and used as isolated in the next step. Isolated 1-(tert-butoxycarbonyl)-3,3-dimethylindoline-2-carboxylic acid (0.25 g, 78% yield) as a brown solid. MS(ESI) m/z: 292.2 (M+H)⁺.

Example 51D. 2-allyl 1-(tert-butyl) 3,3-dimethylindoline-1,2-dicarboxylate 1-(tert-butoxycarbonyl)-3,3-dimethylindoline-2-carboxylate

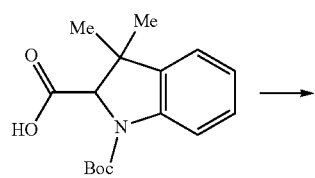

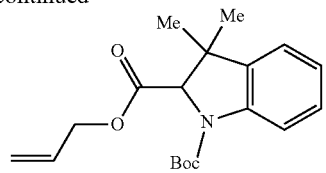

DMF (6 mL) was added to a vial containing 1-(tert-butoxycarbonyl)-3,3-dimethylindoline-2-carboxylic acid (0.9 g, 3.09 mmol) and cesium carbonate (1.00 g, 3.09 mmol). Added allyl bromide (0.267 mL, 3.09 mmol) and heated to 90° C. for 1 hour. The reaction was diluted with water and extracted with EtOAc. The combined organic layers were concentrated and the residue was purified by flash column chromatography, eluting with a linear gradient of 0% to 40% EtOAc in hexanes. Isolated 2-allyl 1-tert-butyl 3,3-dimethylindoline-1,2-dicarboxylate (0.95 g, 93% yield) as a white solid. MS(ESI) m/z: 332.1 (M+H)⁺.

Example 51E. 1-(tert-butyl) 2-methyl 2-allyl-3,3-dimethylindoline-1,2-dicarboxylate

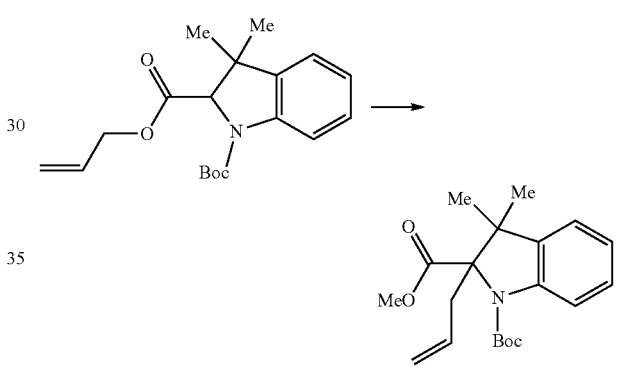

2-allyl 1-tert-butyl 3,3-dimethylindoline-1,2-dicarboxylate (0.84 g, 2.53 mmol) was dissolved in very dry THF (10 mL) and cooled to −78° C. LiHMDS (3.2 mL, 3.2 mmol) was added slowly over 3 minutes. The color changed slightly to orange. The temperature of the reaction was raised reaction to room temperature and then refluxed for 4 hours. After the reaction is complete by LCMS (observation of a more polar product with the same MW), the reaction was quenched with sat. aq. NH₄Cl and diluted with EtOAc. The aqueous layer was extracted with EtOAc. Dry organics and concentrate. Dissolved the residue in 60 mL of 4:1 DCM-MeOH and added TMS-diazomethane (2.5 mL, 5.07 mmol) dropwise. This was allowed to stir at rt for 30 minutes. The reaction was quenched with HOAc and concentrated. The product was purified by eluting with a linear gradient of 0% to 50% EtOAc in hexanes. 1-tert-butyl 2-methyl 2-allyl-3,3-dimethylindoline-1,2-dicarboxylate (0.58 g, 1.67 mmol, 65.7% yield) isolated as a clear oil. MS(ESI) m/z: 346.1 (M+H)⁺.

Example 51

1'-(4-(1H-pyrazol-4-yl)phenyl)-3,3-dimethylspiro[indoline-2,3'-pyrrolidin]-2'-one Prepared using a procedure analogous to EXAMPLE 1, by replacing 1D with 51E. MS(ESI) m/z: 359.1 (M+H)⁺.

HPLC: Method A, RT=8.58 min, 94% purity; Method B, RT=7.26 min, 94% purity. $^1$H NMR (400 MHz. METHANOL-$d_4$) δ 8.01-7.85 (m, 2H), 7.60 (d, J=10.3 Hz, 5H), 6.96 (s, 2H), 6.73-6.64 (m, 1H), 6.65-6.57 (m, 1H), 3.90-3.81 (m, 2H), 2.75-2.62 (m, 1H), 2.34-2.16 (m, 1H), 1.38 (s, 3H), 1.34-1.28 (m, 3H), 0.97-0.78 (m, 2H)

Example 52

1'-(4-(1H-pyrazol-4-yl)phenyl)-4'-(hydroxymethyl)spiro[indoline-2,3'-pyrrolidin]-2'-one

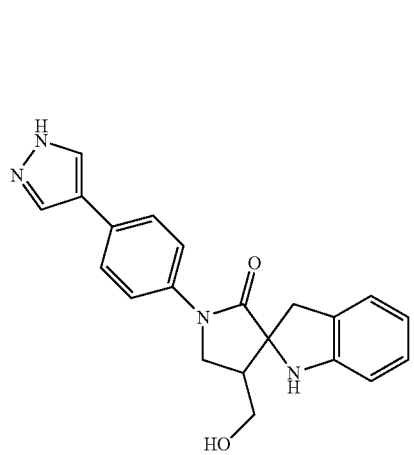

Example 52A. 1'-(4-(1H-pyrazol-4-yl)phenyl)-4'-((benzyloxy)methyl)spiro[indoline-2,3'-pyrrolidin]-2'-one

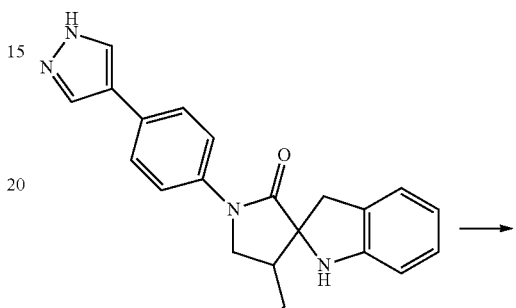

Prepared using a procedure analogous to EXAMPLE 51, by replacing 51C with 1-(tert-butoxycarbonyl)indoline-2-carboxylic acid and allyl bromide with (E)-(((4-bromobut-2-en-1-yl)oxy)methyl)benzene.

Example 52

1'-(4-(1H-pyrazol-4-yl)phenyl)-4'-((hydroxymethyl)spiro[indoline-2,3'-pyrrolidin]-2'-one

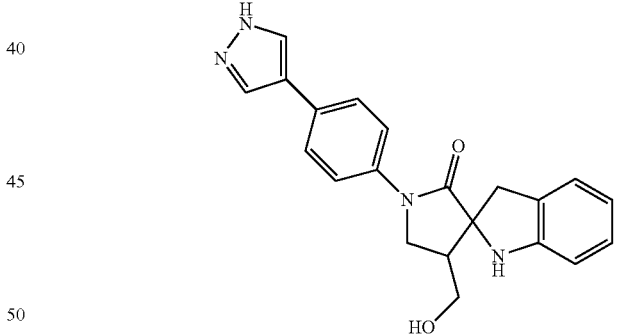

Dissolved 52A (0.5 mmol) in EtOH (15 mL) and added Pd(C) (57 mg of 10% Pd on carbon). Stirred under 55 psi of H$_2$ for 3 hours then filtered through Celite and concentrated. Purified residue by prep HPLC to afford EXAMPLE 52 (0.04 g, 20% yield) as a white solid. MS(ESI) m/z: 361.1 (M+H)$^+$. HPLC: Method A, RT=6.60 min, 94% purity; XBridge. RT=5.08 min, 94% purity. $^1$H NMR (500 MHz, DMSO-$d_6$) δ 8.22-8.11 (m, 1H), 7.96-7.87 (m, 1H), 7.74-7.69 (m, 2H), 7.66-7.62 (m, 2H), 7.01-6.96 (m, 1H), 6.96-6.90 (m, 1H), 6.58-6.50 (m, 1H), 6.50-6.46 (m, 1H), 6.33 (s, 1H), 4.82-4.75 (m, 1H), 3.99-3.92 (m, 1H), 3.71-3.61 (m, 2H), 3.61-3.52 (m, 1H), 2.96-2.90 (m, 1H), 2.49-2.44 (m, 1H)

Example 53

1'-(4-(1H-pyrazol-4-yl)phenyl)-4'-(aminomethyl)spiro[indoline-2,3'-pyrrolidin]-2'-one

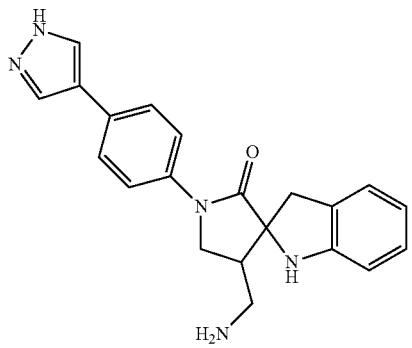 [SMILES: NCC1CN(c2ccc(-c3cn[nH]c3)cc2)C(=O)C12Cc1ccccc1N2]

Example 53A. 2-((1'-(4-(1H-pyrazol-4-yl)phenyl)-2'-oxospiro[indoline-2,3'-pyrrolidin]-4'-yl)methyl)isoindoline-1,3-dione Prepared using a procedure analogous to EXAMPLE 51, by replacing 51C with 1-(tert-butoxycarbonyl)indoline-2-carboxylic acid and by replacing allyl bromide with (E)-2-(4-bromobut-2-en-1-yl)isoindoline-1,3-dione.

Example 53

1'-(4-(H-pyrazol-4-yl)phenyl)-2'-(aminomethyl)spiro[indoline-2,3'-pyrrolidin]-2'-one Dissolved EXAMPLE 53A (0.16 mmol) in EtOH (15 hydrate (0.1 mL) and heated to 60° C. for 1 hour. Concentrated to an orange residue and purified by prep HPLC to afford Example 53. MS(ESI) m/z: 360.1 (M+H)⁺. HPLC Method A, RT=5.70 min, 99% purity; Method B, RT=3.47 min, 99% purity. $^1$H NMR (500 MHz, METHANOL-$d_4$) δ 7.98 (s, 2H), 7.72-7.63 (m, 4H), 7.05 (s, 2H), 6.70 (d, J=7.7 Hz, 2H), 4.07-3.99 (m, 1H), 3.77 (s, 1H), 3.37 (s, 1H), 3.30-3.22 (m, 2H), 3.11 (s, 1H), 3.01 (s, 1H), 2.88 (d, J=0.6 Hz, 1H), 2.81-2.72 (m, 1H)

Example 54

(2S)-1'-(4-(1H-pyrazol-4-yl)phenyl)-4'-(hydroxymethyl)spiro[indoline-2,3'-pyrrolidin]-2'-one

Example 55

(2R)-1'-(4-(1H-pyrazol-4-yl)phenyl)-4'-(hydroxymethyl)spiro[indoline-2,3'-pyrrolidin]-2'-one

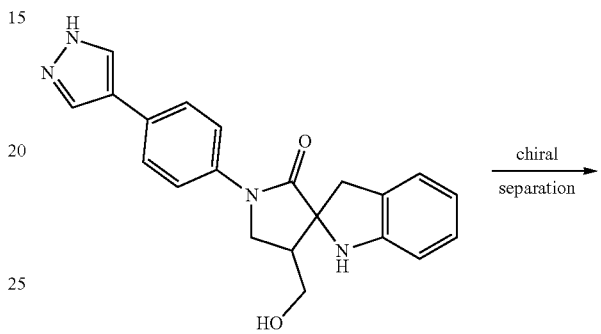

EXAMPLES 54 and 55 were acquired by chiral separation of EXAMPLE 52. Chiralpak IB, 21×250 mm, 5 micron, Mobile Phase: 40% MeOH/60% CO₂. Flow Conditions: 45 mL/min, 150 Bar, 40° C., Detector Wavelength: 275 nm.

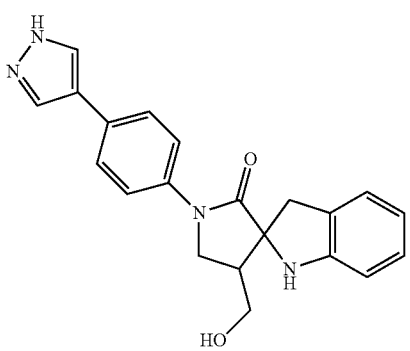

MS(ESI) m/z: 361.1 (M+H)+. HPLC: Method A, RT=5.08 min; Method B, RT=6.60 min. $^1$H NMR (500 MHz, DMSO-d$_6$) δ 8.22-8.11 (m, 1H), 7.96-7.87 (m, 2H), 7.74-7.69 (m, 2H), 7.66-7.62 (m, 2H), 7.01-6.96 (m, 1H), 6.96-6.90 (m, 1H), 6.58-6.50 (m, 1H), 6.50-6.46 (m, 1H), 6.33 (s, 1H), 4.82-4.75 (m, 1H), 3.99-3.92 (m, 1H), 3.71-3.61 (m, 2H), 3.61-3.52 (m, 1H), 2.96-2.90 (m, 1H), 2.49-2.44 (m, 1H)

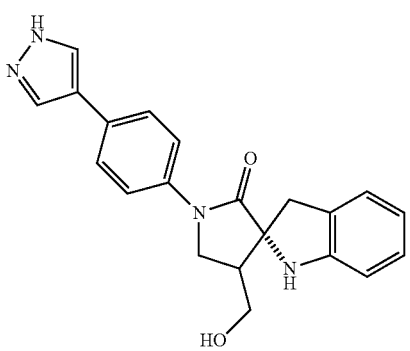 [SMILES: O=C1N(c2ccc(-c3cn[nH]c3)cc2)CC(CO)[C@]12Cc1ccccc1N2]

MS(ESI) m/z: 361.1 (M+H)+. 15 min HPLC: HPLC: Method A, RT=5.08 min; Method B, RT=6.60 min. $^1$H NMR (500 MHz, DMSO-d$_6$) δ 8.22-8.11 (m, 1H), 7.96-7.87 (m, 1H), 7.74-7.69 (m, 2H), 7.66-7.62 (m, 2H), 7.01-6.96 (m, 1H), 6.96-6.90 (m, 1H), 6.58-6.50 (m, 1H), 6.50-6.46 (m, 1H), 6.33 (s, 1H), 4.82-4.75 (m, 1H), 3.99-3.92 (m, 1H), 3.71-3.61 (m, 2H), 3.61-3.52 (m, 1H), 2.96-2.90 (m, 1H), 2.49-2.44 (m, 1H)

Example 56

1-(4-(1H-pyrazol-4-yl)phenyl)-4-(hydroxy methyl)-3',4'-dihydro-1'H-spiro[pyrrolidine-3,2'-quinolin]-2-one

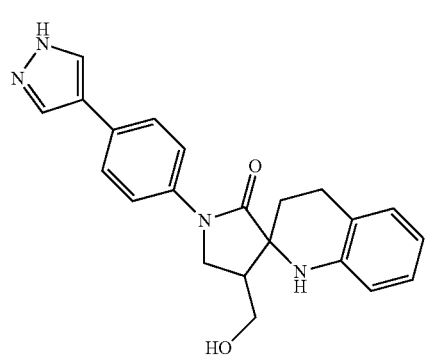 [SMILES: O=C1N(c2ccc(-c3cn[nH]c3)cc2)CC(CO)C12CCc1ccccc1N2]

Prepared using a procedure analogous to EXAMPLE 51, by replacing 51C with 1-(tert-butoxycarbonyl)-1,2,3,4-tetrahydroquinoline-2-carboxylic acid. MS(ESI) m/z: 375.2 (M+H)+. HPLC: Method C, RT 1.25 min. $^1$H NMR (500 MHz, DMSO-d$_6$) δ 8.11-7.96 (m, 1H), 7.70-7.57 (m, 4H), 6.83 (br. s., 2H), 6.55-6.41 (m, 2H), 6.14 (s, 1H), 3.93-3.85 (m, 1H), 3.69 (br. s., 1H), 3.48 (d, J=16.7 Hz, 3H), 2.89-2.75 (m, 1H), 1.97-1.86 (m, 1H), 1.71-1.58 (m, 1H), 0.90-0.80 (m, 1H)

What is claimed is:
1. A compound according to Formula (I):

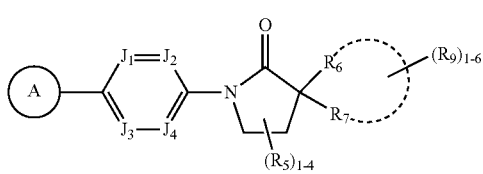

or an enantiomer, a diastereomer, a stereoisomer, a tautomer, or a pharmaceutically acceptable salt thereof, wherein Ring A is independently selected from

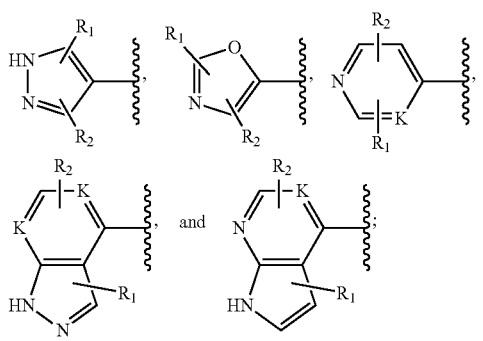

$J_1$, $J_2$, $J_3$, and $J_4$ are independently selected from N, $CR_3$, and $CR_4$; provided no more than two of $J_1$, $J_2$, $J_3$, and $J_4$ are N;

K, at each occurrence, is independently selected from N, $CR_1$, and $CR_2$;

$R_1$, at each occurrence, is independently selected from H, F, Cl, Br, OH, CN, $NR_aR_a$, —$OC_{1-4}$ alkyl substituted with 0-3 Re, and $C_{1-4}$ alkyl substituted with 0-3 Re;

$R_2$, at each occurrence, is independently selected from H, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)OR_b$, —$(CH_2)_rNR_aC(=O)NR_aR_a$, —$(CH_2)_rOC(=O)OR_b$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_3$ is independently selected from H, F, Cl, Br, CN, $C_{1-4}$ alkyl substituted with 0-3 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rCN$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, $OC-14$ alkyl substituted with 0-3 $R_e$, $NR_aR_a$, and $C_{1-4}$ alkyl substituted with 0-3 $R_e$;

$R_5$ is independently selected from H, $C_{1-4}$alkyl substituted with 0-4 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rCN$, —$(CH_2)_rC(=O)NR_aR_a$, —$(CH_2)_rNR_aC(=O)R_b$, —$(CH_2)_rNR_aC(=O)NR_aR_a$, —$(CH_2)_rNR_aC(=O)OR_b$, —$(CH_2)_rOC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, —$C(=O)$-heterocyclyl substituted with 0-3 $R_e$, and —$(CH_2)_r$-heterocyclyl substituted with 0-3 $R_e$;

$R_6$ and $R_7$ together with the carbon atom to which they are both attached form a bicyclic carbocyclyl or a bicyclic heterocyclyl comprising carbon atoms and 1-5 heteroatoms selected from $NR_8$, O, and S;

$R_8$ is independently selected from H and $C_{1-4}$ alkyl substituted with 0-4 $R_e$;

$R_9$, at each occurrence, is independently selected from H, F, Cl, Br, $C_{1-4}$alkyl, $C_{2-4}$alkenyl, $C_{2-4}$alkynyl, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)OR_b$, —$(CHR_d)_rC(=O)NR_aR_a$, —$(CHR_d)_rOC(=O)R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-heterocyclyl, —$(CH_2)_r$-aryl, —$(CH_2)_r$-heteroaryl, F, Cl, Br, CN, $NO_2$, =O, —$(CH_2)_rOR_f$, $S(O)_pR_f$, $C(=O)NR_fR_f$, $NR_fC(=O)R_d$, $S(O)_pNR_fR_f$, $NR_fS(O)_pR_d$, $NR_fC(=O)OR_d$, $OC(=O)NR_fR_f$, and —$(CH_2)_rNR_fR_f$;

$R_f$, at each occurrence, is independently selected from H, F, Cl, Br, CN, OH, $C_{1-5}$alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2;

r, at each occurrence, is independently selected from zero, 1, 2, 3, and 4.

2. The compound of claim 1, having Formula (II):

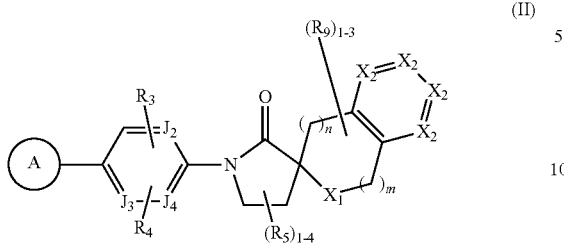

or an enantiomer, a diastereomer, a stereoisomer, a tautomer, a pharmaceutically acceptable salt thereof, wherein
Ring A is independently selected from

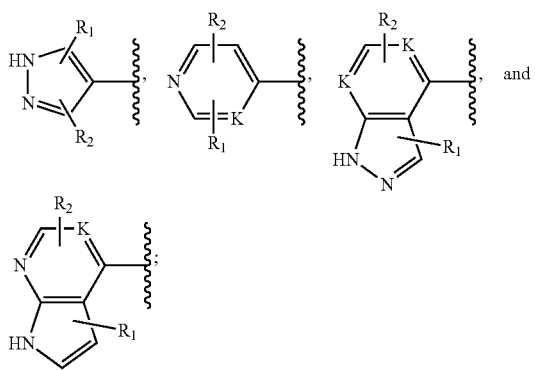

$J_2$, $J_3$, and $J_4$ are independently selected from N, $CR_3$, and $CR_4$;
K, at each occurrence, is independently selected from N, $CR_1$, and $CR_2$;
$X_1$ is independently selected from $CR_9R_9$ O, and $NR_8$;
$X_2$ is independently selected from $CR_9$ and N; provided no more than three of $X_2$ are N;
$R_1$, at each occurrence, is independently selected from H, F, Cl, Br, CN, $NR_aR_a$, and $C_{1-4}$alkyl substituted with 0-4 $R_e$;
$R_2$, at each occurrence, is independently selected from H, F, Cl, Br, OH, CN, $NR_aR_a$, and $C_{1-4}$alkyl substituted with 0-4 $R_e$;
$R_3$ is independently selected from H, F, Cl, Br, CN, $C_{1-4}$ alkyl substituted with 0-3 $R_e$, $-(CH_2)_rOR_b$, and $-C_{3-6}$ cycloalkyl;
$R_4$ is independently selected from H, F, Cl, Br, OH, CN, OC-14 alkyl substituted with 0-3 $R_e$, and $C_{1-4}$ alkyl substituted with 0-3 $R_e$;
$R_5$ is independently selected from H, =O, $C_{1-4}$alkyl substituted with 0-4 $R_e$, $-(CH_2)_rOR_b$, $C(=O)R_b$, and $-C(=O)OR_b$;
$R_8$ is independently selected from H and $C_{1-4}$ alkyl substituted with 0-4 $R_e$;
$R_9$ is independently selected from H, F, Cl, Br, $C_{1-4}$ alkyl, nitro, $-(CH_2)_rS(O)_pR_c$, $-(CH_2)_rS(O)_pNR_aR_a$, $-(CH_2)_rNR_aS(O)_pR_c$, $-(CH_2)_rOR_b$, $-(CH_2)_rCN$, $-(CH_2)_rNR_aR_a$, $-(CH_2)_rNR_aC(=O)R_b$, $-(CH_2)_rNR_aC(=O)NR_aR_a$, $-(CH_2)_rC(=O)OR_b$, $-(CH_2)_rC(=O)R_b$, $-C(=O)NR_aR_a$, $-(CH_2)_rOC(=O)R_b$, $-(CH_2)_r$-cycloalkyl, $-(CH_2)_r$-heterocyclyl, $-(CH_2)_r$-aryl, and $-(CH_2)_r$-heteroaryl, wherein said alkyl, cycloalkyl, heterocyclyl, aryl, or heteroaryl is substituted with 0-4 $R_e$;
$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$cycloalkyl substituted with 0-5 $R_e$, $-(CH_2)_r$-aryl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;
$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, $-(CH_2)_r$-heterocyclyl, $-(CH_2)_r$-aryl, F, Cl, Br, CN, $NO_2$, =O, $CO_2H$, $-(CH_2)_rOR_f$, $S(O)_pR_f$, $S(O)_pNR_fR_f$ and $-(CH_2)_rNR_fR_f$;
$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;
m is independently selected from 0 and 1;
n is independently selected from 1 and 2;
p, at each occurrence, is independently selected from zero, 1, and 2; and
r, at each occurrence, is independently selected from zero, 1, 2, 3, and 4.

3. The compound of claim 2, having Formula (III):

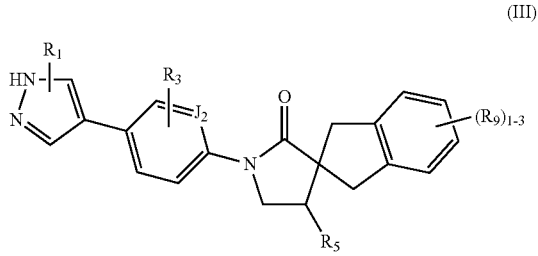

or enantiomer, a diastereomer, a stereoisomer, a tautomer, a pharmaceutically acceptable salt thereof, wherein
$J_2$ is independently selected from N and $CR_3$;
$R_1$ is independently selected from H and $CF_3$;
$R_3$ is independently selected from H, CN, $C_{1-4}$ alkyl, $-OC_{1-3}$ alkyl, and $-C_{3-6}$ cycloalkyl;
$R_5$ is independently selected from H, $C_{1-4}$alkyl substituted with 0-4 $R_e$, $-(CH_2)_rOR_b$, $(CH_2)_rS(O)_pR_c$, $-(CH_2)_rC(=O)R_b$, $-(CH_2)_rNR_aR_a$, and $-(CH_2)_rCN$;
$R_9$, at each occurrence, is independently selected from H, F, Cl, $C_{1-4}$ alkyl substituted with 0-3 $R_e$, $-OR_b$, CN, $C(=O)NR_aR_a$, and heterocyclyl substituted with 0-3 $R_e$;

R$_a$, at each occurrence, is independently selected from H, C$_{1-6}$ alkyl substituted with 0-5 R$_e$, —(CH$_2$)$_r$—C$_{3-6}$ cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_e$, at each occurrence, is independently selected from C$_{1-6}$ alkyl substituted with 0-5 R$_f$, F, Cl, Br, CN, NO$_2$, =O, CO$_2$H, OH, OC$_{1-4}$alkyl, and NR$_f$R$_f$;

R$_f$, at each occurrence, is independently selected from H, F, Cl, Br, CN, OH, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

r, at each occurrence, is independently selected from zero, 1, 2, and 3.

4. The compound of claim 3, having Formula (IV):

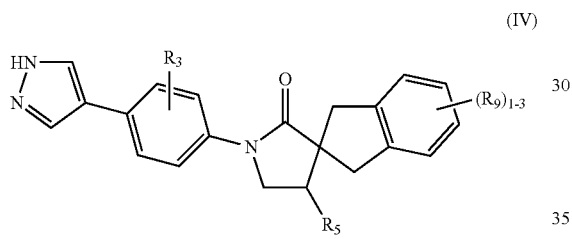

(IV)

or enantiomer, a diastereomer, a stereoisomer, a tautomer, a pharmaceutically acceptable salt thereof, wherein R$_3$ is independently selected from H, CN, C$_{1-4}$ alkyl, and —OC$_{1-3}$ alkyl;

R$_5$ is independently selected from H, C$_{1-4}$alkyl substituted with 0-4 R$_e$, —(CH$_2$)$_r$OR$_b$, —(CH$_2$)$_r$NR$_a$R$_a$, and —(CH$_2$)$_r$CN;

R$_9$, at each occurrence, is independently selected from H, F, Cl, C$_{1-4}$ alkyl substituted with 0-3 R$_e$, —OR$_b$, CN, C(=O)NR$_a$R$_a$, and heterocyclyl substituted with 0-3 R$_e$;

R$_a$, at each occurrence, is independently selected from H, C$_{1-6}$ alkyl substituted with 0-5 R$_e$, —(CH$_2$)$_r$—C$_{3-6}$ cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$;

R$_b$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_e$, at each occurrence, is independently selected from C$_{1-6}$ alkyl substituted with 0-5 R$_f$, F, Cl, Br, CN, NO$_2$, =O, CO$_2$H, OH, and OC$_{1-4}$alkyl; and r, at each occurrence, is independently selected from zero, 1, 2, and 3.

5. The compound of claim 2, having Formula (V):

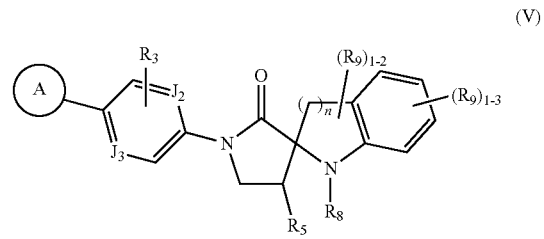

(V)

or enantiomer, a diastereomer, a stereoisomer, a tautomer, a pharmaceutically acceptable salt thereof, wherein Ring A is independently selected from

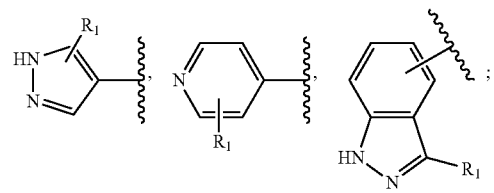

J$_2$ and J$_3$ are independently selected from N and CR$_3$;

R$_1$ is independently selected from H and CF$_3$;

R$_3$ is independently selected from H, CN, C$_{1-4}$ alkyl, —OC$_{1-3}$ alkyl, and —C$_{3-6}$ cycloalkyl;

R$_5$ is independently selected from H, C$_{1-4}$alkyl substituted with 0-4 R$_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, and —(CH$_2$)$_r$CN;

R$_8$ is independently selected from H and C$_{1-4}$ alkyl substituted with 0-4 R$_e$;

R$_9$, at each occurrence, is independently selected from H, F, Cl, C$_{1-4}$ alkyl substituted with 0-3 R$_e$, —OR$_b$, CN, C(=O)NR$_a$R$_a$, and heterocyclyl substituted with 0-3 R$_e$;

R$_a$, at each occurrence, is independently selected from H, C$_{1-6}$ alkyl substituted with 0-5 R$_e$, —(CH$_2$)$_r$—C$_{3-6}$ cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_e$, at each occurrence, is independently selected from C$_{1-6}$ alkyl substituted with 0-5 R$_f$, F, Cl, Br, CN, NO$_2$, =O, CO$_2$H, OH, OC$_{1-4}$alkyl, and NR$_f$R$_f$;

R$_f$, at each occurrence, is independently selected from H, F, Cl, Br, CN, OH, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

n is independently selected from 1 and 2;

r, at each occurrence, is independently selected from zero, 1, 2, and 3.

6. The compound of claim 5, having Formula (VI):

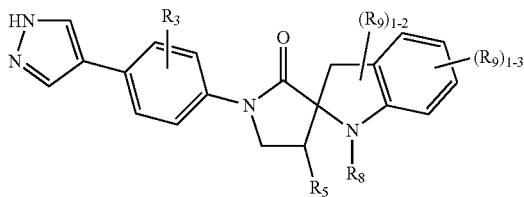

(VI)

or enantiomer, a diastereomer, a stereoisomer, a tautomer, a pharmaceutically acceptable salt thereof, wherein
$R_3$ is independently selected from H, CN, $C_{1-4}$ alkyl, and —$OC_{1-3}$ alkyl;
$R_5$ is independently selected from H, $C_{1-4}$alkyl substituted with 0-4 $R_e$, —$(CH_2)_rOR_b$, —$(CH_2)_rNR_aR_a$, and —$(CH_2)_rCN$;
$R_8$ is independently selected from H and $C_{1-4}$ alkyl substituted with 0-4 $R_e$;
$R_9$, at each occurrence, is independently selected from H, F, Cl, $C_{1-4}$ alkyl substituted with 0-3 $R_e$, —$OR_b$, CN, C(=O)$NR_aR_a$, and heterocyclyl substituted with 0-3 $R_e$;
$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;
r, at each occurrence, is independently selected from zero, 1, 2, and 3.

7. The compound of claim 5, having Formula (VII):

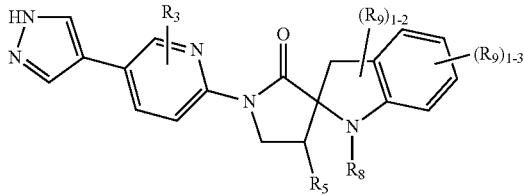

(VII)

or enantiomer, a diastereomer, a stereoisomer, a tautomer, a pharmaceutically acceptable salt thereof, wherein
$R_3$ is independently selected from H, CN, $C_{1-4}$ alkyl, and —$OC_{1-3}$ alkyl;
$R_5$ is independently selected from H, $C_{1-4}$alkyl substituted with 0-4 $R_e$, —$(CH_2)_rOR_b$, —$(CH_2)_rNR_aR_a$, and —$(CH_2)_rCN$;
$R_8$ is independently selected from H and $C_{1-4}$ alkyl substituted with 0-4 $R_e$;
$R_9$, at each occurrence, is independently selected from H, F, Cl, $C_{1-4}$ alkyl substituted with 0-3 $R_e$, —$OR_b$, CN, C(=O)$NR_aR_a$, and heterocyclyl substituted with 0-3 $R_e$;
$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;
r, at each occurrence, is independently selected from zero, 1, 2, and 3.

8. The compound of claim 5, having Formula (VIII):

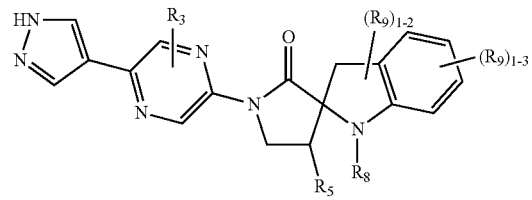

(VIII)

or enantiomer, a diastereomer, a stereoisomer, a tautomer, a pharmaceutically acceptable salt thereof, wherein
$R_3$ is independently selected from H, CN, $C_{1-4}$ alkyl, and —$OC_{1-3}$ alkyl;
$R_5$ is independently selected from H, $C_{1-4}$alkyl substituted with 0-4 $R_e$, —$(CH_2)_rOR_b$, —$(CH_2)_rNR_aR_a$, and —$(CH_2)_rCN$;
$R_8$ is independently selected from H and $C_{1-4}$ alkyl substituted with 0-4 $R_e$;
$R_9$, at each occurrence, is independently selected from H, F, Cl, $C_{1-4}$ alkyl substituted with 0-3 $R_e$, —$OR_b$, CN, C(=O)$NR_aR_a$, and heterocyclyl substituted with 0-3 $R_e$;
$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;
r, at each occurrence, is independently selected from zero, 1, 2, and 3.

9. The compound of claim 5, having Formula (IX):

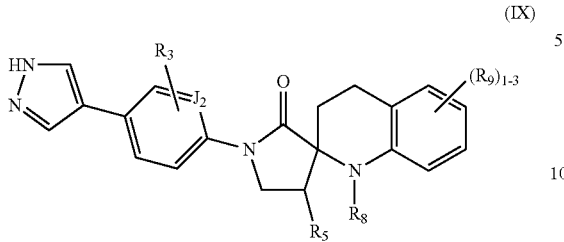

(IX)

or enantiomer, a diastereomer, a stereoisomer, a tautomer, a pharmaceutically acceptable salt thereof, wherein
$J_2$ is independently selected from N and $CR_3$;
$R_3$ is independently selected from H, CN, $C_{1-4}$ alkyl, and —$OC_{1-3}$ alkyl;
$R_5$ is independently selected from H, $C_{1-4}$alkyl substituted with 0-4 $R_e$, —$(CH_2)_rOR_b$, —$(CH_2)_rNR_aR_a$, and —$(CH_2)_rCN$;
$R_8$ is independently selected from H and $C_{1-4}$ alkyl substituted with 0-4 $R_e$;
$R_9$, at each occurrence, is independently selected from H, F, Cl, $C_{1-4}$ alkyl substituted with 0-3 $R_e$, —$OR_b$, CN, C(=O)$NR_aR_a$, and heterocyclyl substituted with 0-3 $R_e$;
$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, =O, $CO_2H$, OH, and $OC_{1-4}$alkyl;
r, at each occurrence, is independently selected from zero, 1, 2, and 3.

10. The compound of claim 2, having Formula (X):

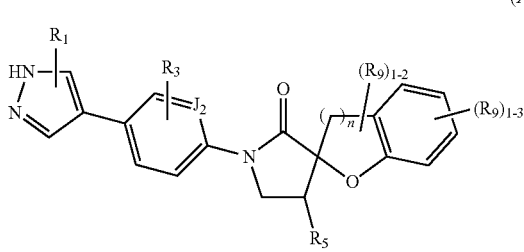

(X)

or enantiomer, a diastereomer, a stereoisomer, a tautomer, a pharmaceutically acceptable salt thereof, wherein
$J_2$ is independently selected from N and $CR_3$;
$R_1$ is independently selected from H and $CF_3$;
$R_3$ is independently selected from H, CN, $C_{1-4}$ alkyl, —$OC_{1-3}$ alkyl, and —$C_{3-6}$ cycloalkyl;
$R_5$ is independently selected from H, $C_{1-4}$alkyl substituted with 0-4 $R_e$, —$(CH_2)_rOR_b$, $(CH_2)_rS(O)_pR_c$, —$(CH_2)_rC(=O)R_b$, —$(CH_2)_rNR_aR_a$, and —$(CH_2)_rCN$;

$R_9$, at each occurrence, is independently selected from H, F, Cl, $C_{1-4}$ alkyl substituted with 0-3 $R_e$, —$OR_b$, CN, C(=O)$NR_aR_a$, and heterocyclyl substituted with 0-3 $R_e$;
$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_e$, at each occurrence, is independently selected from $C_{1-6}$ alkyl substituted with 0-5 $R_f$, F, Cl, Br, CN, $NO_2$, =O, $CO_2H$, OH, $OC_{1-4}$alkyl, and $NR_fR_f$;
$R_f$, at each occurrence, is independently selected from H, F, Cl, Br, CN, OH, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;
n is independently selected from 1 and 2;
r, at each occurrence, is independently selected from zero, 1, 2, and 3.

11. The compound of claim 10, having Formula (XI):

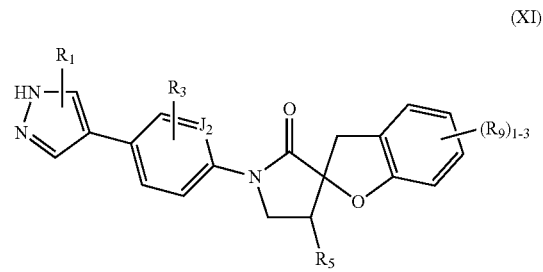

(XI)

or enantiomer, a diastereomer, a stereoisomer, a tautomer, a pharmaceutically acceptable salt thereof, wherein
$J_2$ is independently selected from N and $CR_3$;
$R_1$ is independently selected from H and $CF_3$;
$R_3$ is independently selected from H, CN, $C_{1-4}$ alkyl, —$OC_{1-3}$ alkyl, and —$C_{3-6}$ cycloalkyl;
$R_5$ is independently selected from H, $C_{1-4}$alkyl substituted with 0-4 $R_e$, —$(CH_2)_rOR_b$, $(CH_2)_rS(O)_pR_c$, —$(CH_2)_rC(=O)R_b$, —$(CH_2)_rNR_aR_a$, and —$(CH_2)_rCN$;
$R_9$, at each occurrence, is independently selected from H, F, Cl, $C_{1-4}$ alkyl substituted with 0-3 $R_e$, —$OR_b$, CN, C(=O)$NR_aR_a$, and heterocyclyl substituted with 0-3 $R_e$;
$R_a$, at each occurrence, is independently selected from H, $C_{1-6}$ alkyl substituted with 0-5 $R_e$, —$(CH_2)_r$—$C_{3-6}$ cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

R_e, at each occurrence, is independently selected from C_{1-6} alkyl substituted with 0-5 R_f, F, Cl, Br, CN, NO_2, =O, CO_2H, OH, OC_{1-4}alkyl, and NR_fR_f;

R_f, at each occurrence, is independently selected from H, F, Cl, Br, CN, OH, C_{1-5} alkyl, C_{3-6} cycloalkyl, and phenyl, or R_f and R_f together with the nitrogen atom to which they are both attached form a heterocyclic ring optionally substituted with C_{1-4}alkyl;

r, at each occurrence, is independently selected from zero, 1, 2, and 3.

12. A pharmaceutical composition comprising one or more compounds according to claim 1 and a pharmaceutically acceptable carrier or diluent.

13. The compound of claim 1 or an enantiomer, a diastereomer, a stereoisomer, a tautomer, a pharmaceutically acceptable salt thereof, which is selected from:

1'-(4-(1H-Pyrazol-4-yl)phenyl)spiro[indoline-2,3'-pyrrolidin]-2'-one;
1'-(4-(1H-Pyrazol-4-yl)phenyl)spiro[indoline-2,3'-pyrrolidin]-2'-one;
1'-(4-(1H-Pyrazol-4-yl)phenyl)-6-methoxyspiro[indoline-2,3'-pyrrolidin]-2'-one;
1'-(4-(1H-Pyrazol-4-yl)phenyl)-6-methoxyspiro[indoline-2,3'-pyrrolidin]-2'-one;
1'-(4-(1H-Pyrazol-4-yl)phenyl)-5-fluorospiro[indoline-2,3'-pyrrolidin]-2'-one, TFA;
1'-(4-(1H-Pyrazol-4-yl)phenyl)-5-fluorospiro[indoline-2,3'-pyrrolidin]-2'-one;
1'-(6-Methoxy-5-(1H-pyrazol-4-yl)pyridin-2-yl)spiro[indoline-2,3'-pyrrolidin]-2'-one TFA;
1'-(4-(1H-Pyrazol-4-yl)phenyl)-1,3-dihydrospiro[indene-2,3'-pyrrolidin]-2'-one, TFA;
1'-(4-(1H-Pyrazol-4-yl)phenyl)-5-methoxyspiro[indoline-2,3'-pyrrolidin]-2'-one;
1'-(4-(1H-Indazol-5-yl)phenyl)spiro[indoline-2,3'-pyrrolidin]-2'-one;
1'-(4-(1H-Pyrazol-4-yl)phenyl)-6-methoxy-1-methyl spiro[indoline-2,3'-pyrrolidin]-2'-one;
1'-(4-(1H-Pyrazol-4-yl)phenyl)-5-fluoro-1,3-dihydrospiro[indene-2,3'-pyrrolidin]-2'-one;
5-Fluoro-1'-(6-methoxy-5-(1H-pyrazol-4-yl)pyridin-2-yl)-1,3-dihydrospiro[indene-2,3'-pyrrolidin]-2'-one;
5-Methoxy-1'-(6-methoxy-5-(1H-pyrazol-4-yl)pyridin-2-yl)-1,3-dihydrospiro[indene-2,3'-pyrrolidin]-2'-one;
1'-(4-(1H-Pyrazol-4-yl)phenyl)-5-methoxy-1,3-dihydrospiro[indene-2,3'-pyrrolidin]-2'-one;
1'-(6-Methoxy-5-(1H-pyrazol-4-yl)pyridin-2-yl)-1,3-dihydrospiro[indene-2,3'-pyrrolidin]-2'-one;
1'-(4-(1H-Pyrazol-4-yl)phenyl)-5-methoxy-3H-spiro[benzofuran-2,3'-pyrrolidin]-2'-one;
1'-(4-(1H-Pyrazol-4-yl)phenyl)-5-methoxy-3H-spiro[benzofuran-2,3'-pyrrolidin]-2'-one;
1'-(4-(1H-Pyrazol-4-yl)phenyl)-4-methylspiro[indoline-2,3'-pyrrolidin]-2'-one;
1-(4-(1H-Pyrazol-4-yl)phenyl)-1',3'-dihydrospiro[pyrrolidine-3,2'-pyrrolo[3,2-b]pyridin]-2-one;
1'-(4-(1H-Pyrazol-4-yl)phenyl)-3H-spiro[benzofuran-2,3'-pyrrolidin]-2'-one;
1'-(4-(1H-Pyrazol-4-yl)phenyl)-3H-spiro[benzofuran-2,3'-pyrrolidin]-2'-one;
1'-(4-(1H-Pyrazol-4-yl)phenyl)-3H-spiro[benzofuran-2,3'-pyrrolidin]-2'-one;
1'-(4-(1H-Pyrazol-4-yl)phenyl)-3H-spiro[benzofuran-2,3'-pyrrolidin]-2'-one;
1'-(3-Methoxy-4-(1H-pyrazol-4-yl)phenyl)-1,3-dihydrospiro[indene-2,3'-pyrrolidin]-2'-one;
1'-(4-(1H-Pyrazol-4-yl)phenyl)-6-hydroxyspiro[indoline-2,3'-pyrrolidin]-2'-one;
1'-(4-(1H-Pyrazol-4-yl)phenyl)-6-(2-hydroxy-2-methylpropoxy)spiro[indoline-2,3'-pyrrolidin]-2'-one;
1'-(4-(1H-Pyrazol-4-yl)phenyl)-4-fluoro-6-methoxyspiro[indoline-2,3'-pyrrolidin]-2'-one;
1'-(5-(1H-Pyrazol-4-yl)pyridin-2-yl)spiro[indoline-2,3'-pyrrolidin]-2'-one;
1'-(4-(1H-Pyrazol-4-yl)phenyl)-6-(cyclopropylmethoxy)spiro[indoline-2,3'-pyrrolidin]-2'-one;
1'-(5-(1H-Pyrazol-4-yl)pyrazin-2-yl)spiro[indoline-2,3'-pyrrolidin]-2'-one;
1'-(4-(Pyridin-4-yl)phenyl)spiro[indoline-2,3'-pyrrolidin]-2'-one;
1'-(4-(Pyridin-4-yl)phenyl)-3H-spiro[benzofuran-2,3'-pyrrolidin]-2'-one;
1-(4-(1H-pyrazol-4-yl)phenyl)-3',4'-dihydro-1'H-spiro[pyrrolidine-3,2'-quinolin]-2-one;
1'-(4-(1H-pyrazol-4-yl)phenyl)-1,4-dihydro-2H-spiro[isoquinoline-3,3'-pyrrolidin]-2'-one;
1'-(4-(1H-pyrrolo[2,3-b]pyridin-4-yl)phenyl)-1,4-dihydro-2H-spiro[isoquinoline-3,3'-pyrrolidin]-2'-one;
1'-(4-(1H-Pyrazol-4-yl)phenyl)spiro[chromane-2,3'-pyrrolidin]-2'-one;
1'-(4-(1H-Pyrazol-4-yl)phenyl)-3,3-dimethylspiro[indoline-2,3'-pyrrolidin]-2'-one;
1'-(4-(1H-Pyrazol-4-yl)phenyl)-4'-(hydroxymethyl)spiro[indoline-2,3'-pyrrolidin]-2'-one;
1'-(4-(1H-Pyrazol-4-yl)phenyl)-4'-(aminomethyl)spiro[indoline-2,3'-pyrrolidin]-2'-one;
(2S)-1'-(4-(1H-pyrazol-4-yl)phenyl)-4'-(hydroxymethyl)spiro[indoline-2,3'-pyrrolidin]-2'-one;
(2R)-1'-(4-(1H-pyrazol-4-yl)phenyl)-4'-(hydroxymethyl)spiro[indoline-2,3'-pyrrolidin]-2'-one; and
1-(4-(1H-pyrazol-4-yl)phenyl)-4-(hydroxymethyl)-3',4'-dihydro-1'H-spiro[pyrrolidine-3,2'-quinolin]-2-one.

* * * * *